(12) United States Patent
Laudanna et al.

(10) Patent No.: US 10,898,548 B2
(45) Date of Patent: Jan. 26, 2021

(54) MODULATORS OF PROTEIN TYROSINE PHOSPHATASE AND USES THEREOF

(71) Applicant: LEUVAS THERAPEUTICS, Mountain View, CA (US)

(72) Inventors: Carlo Laudanna, Verona (IT); Lucia De Franceschi, Verona (IT)

(73) Assignee: LEUVAS THERAPEUTICS, Mountain View, CA (US)

( * ) Notice: Subject to any disclaimer, the term of this patent is extended or adjusted under 35 U.S.C. 154(b) by 0 days.

(21) Appl. No.: 15/547,436

(22) PCT Filed: Jan. 28, 2016

(86) PCT No.: PCT/US2016/015428
§ 371 (c)(1),
(2) Date: Jul. 28, 2017

(87) PCT Pub. No.: WO2016/123380
PCT Pub. Date: Aug. 4, 2016

(65) Prior Publication Data
US 2018/0256687 A1    Sep. 13, 2018

Related U.S. Application Data

(60) Provisional application No. 62/109,555, filed on Jan. 29, 2015.

(51) Int. Cl.
*A61K 38/46* (2006.01)
*C12Q 1/42* (2006.01)
*G01N 33/68* (2006.01)

(52) U.S. Cl.
CPC .............. *A61K 38/465* (2013.01); *C12Q 1/42* (2013.01); *C12Y 301/03048* (2013.01); *G01N 33/6842* (2013.01); *G01N 2333/916* (2013.01); *G01N 2440/14* (2013.01)

(58) Field of Classification Search
CPC .................... A61K 38/465; C12Q 1/42; C12Y 301/03048; G01N 33/6842; G01N 2333/916; G01N 2440/14
USPC ........................................................ 424/94.6
See application file for complete search history.

(56) References Cited

U.S. PATENT DOCUMENTS 5,532,123 A   7/1996   Schlessinger
7,026,167 B2  4/2006   Hunt et al.

FOREIGN PATENT DOCUMENTS

WO    2007085958 A2    8/2007

OTHER PUBLICATIONS

Cheung et al., Functional Analysis of a Cell Cycle-Associated, Tumor-Suppressive Gene, Protein Tyrosine Phosphatase Receptor Type G, in Nasopharyngeal Carcinoma, Cancer Research, vol. 68, No. 19, (2008), p. 8137-8145.*
Melchiori et al., β-Thalassemia: HiJAKing Ineffective Erythropoiesis and Iron Overload, Advances in Hematology, vol. 2010, (2010), Article ID 938640, p. 1-7.*
Lang et al., "Mechanisms and pathophysiological significance of eryptosis, the suicidal erythrocyte death", Semin. Cell Develop. Biol., Mar. 2015, pp. 35-42, vol. 39, Elsevier, New York City, NY.
Peruta et al., "Protein tyrosine phosphatase receptor type γ is a functional tumor suppressor gene specifically downregulated in chronic myeloid leukemia", Cancer Res., Nov. 2010, pp. 8896-8906, vol. 70, Issue 21, American Association for Cancer Research, Philadelphia, PA.
Jiang et al., "Dimenzation inhibits the activity of receptor-like protein-tyrosine phosphatase-α", Nature, 1999, 401 (6753): 606-610.
Majeti et al., "An Inactivating Point Mutation in the Inhibitory Wedge of CD45 Causes Lymphoproliferation and Autoimmunity", Cell, 2000, 103(7): 1059-1070.
Mirenda et al., "Protein Tyrosine Phosphatase Receptor Type Y Is a JAK Phosphatase and Negatively Regulates Leukocyte Integrin Activation", J. Immunol., 2015, 194(5): 2168-2179.
Xie et al., "Protein-tyrosine Phosphatase (PTP) Wedge Domain Peptides: A Novel Approach for Inhibition of PTP Function and Augmentation of Protein-Tyrosine Kinase Function", The Journal of Biological Chemistry, 2006, 281(24): 16482-16492.

* cited by examiner

*Primary Examiner* — Jennifer M. H. Tichy
(74) *Attorney, Agent, or Firm* — Pamela J. Sherwood; Bozicevic, Field & Francis LLP

(57) ABSTRACT

Composition and methods are provided for the specific manipulation of protein tyrosine phosphatase (PTP) activity, including without limitation manipulation of protein tyrosine phosphatase receptor type gamma (PTPRG). The modulation of PTP activity can be performed in vitro or in vivo, and is useful for therapeutic and research purposes. In some embodiments, an effective dose of a PTP modulator is provided to an individual for preventing or treating disease involving dysregulated tyrosine kinase activity and/or signaling mechanisms involving tyrosine phosphorylation and/ or tyrosine kinase activity. In other embodiments, a PTP modulator is utilized in the analysis and screening of phosphatase pathways in a cell.

7 Claims, No Drawings
Specification includes a Sequence Listing.

MODULATORS OF PROTEIN TYROSINE PHOSPHATASE AND USES THEREOF

CROSS-REFERENCE

This application claims the benefit of U.S. Provisional Patent Application Ser. No. 62/109,555, filed Jan. 29, 2015, which application is incorporated by reference herein in its entirety.

FIELD OF THE INVENTION

The present invention relates to compositions that modulate the activity of protein tyrosine phosphatases, particularly protein tyrosine phosphatase receptor type gamma (PTPRG), and uses thereof.

BACKGROUND OF THE INVENTION

The protein tyrosine phosphatase (PTP) superfamily of enzymes acts in a coordinated manner with protein tyrosine kinases to control signaling pathways that regulate a broad spectrum of fundamental physiological and pathological processes including differentiation, proliferation, apoptosis, survival, migration, activation, adhesion and invasion of many cell types, which are relevant to many human diseases including, without limitation, cancer, inflammation, immunity, autoimmunity, and hematopoiesis. PTPs play a critical role in regulating cellular function by selectively dephosphorylating their substrates, thus influencing the phosphoproteome. The importance of phosphorylation and the regulatory role of protein kinases in general and tyrosine protein kinases in particular, is well established; however, more recently the role of protein phosphatases is emerging as a key regulator of signal transduction.

The protein tyrosine phosphatases (PTP) superfamily includes receptor-like (RPTP) and non-transmembrane (NTs) proteins for a total of 38 coding genes (reviewed in Tonks N K, 2006, Nat Rev Mol Cell Biol 7: 833-846). Particularly, RPTPs display a modular structure including a variable extracellular region, consisting of different domains possibly implicated in cell-cell and cell-matrix adhesive contacts, and an intracellular region commonly shared with other components of the superfamily. The intracellular region is typically composed of two domains named D1 and D2. The catalytic activity resides in the D1 domain, while the D2 is possibly involved in substrate specificity, stability and protein-protein interaction of RPTPs. The activity of RPTPs is controlled by a variety of mechanisms (Tonks N K, 2013, FEBS J 280: 346-378). Although not established for all RPTPs, the main regulatory mechanism of RPTPs activity consists in the reversible transition from a homodimeric inactive form to a monomeric active form (Majeti R et al, 1998, Science 279: 88-91; Jiang G, 1999, Nature 401: 606-610). Oxidative stress is also an important regulatory mechanism of RPTPs, leading to homodimer stabilization, hence to the inactivation of the enzyme itself (Tonks N K, 2006, Nat Rev Mol Cell Biol 7: 833-846).

Protein tyrosine phosphatase receptor-type gamma (PTPRG) is a member of the receptor-like PTPs. PTPRG is a transmembrane protein, the extracellular region contains a carbonic anhydrase-homologous and a fibronectin type III domain and the intracellular domain contains of two intracellular protein tyrosine kinase phosphatase catalytic domains. PTPRG is located at chromosomal arm 3p14.2 and since this region is often deleted in several cancers it was described as a candidate tumor suppressor gene. PTPRG is broadly expressed in many normal tissues, including without limitation, leukocytes, hematopoietic cells, myeloid and plasmacytoid dendritic cells, mast cells, epithelial and endothelial cells, and expressed and dysregulated in a large number of neoplastic tissues (Vezzalini M. et al 2007 50(5):615-28; Lissandrini D et al 2006 Blood 108(13)4223-4231). Tight regulation of the tyrosine kinase and tyrosine phosphatase balance and the resulting phosphoproteome is essential for cell homeostasis and dysregulation of this network may lead to disturbances in a variety of vital cellular pathways, such as cell proliferation and differentiation, and thus to complex diseases including cancer and dysregulated hematopoiesis. In fact, PTPRG has been reported to be a tumor suppressor (reviewed in Laczmanska and Sasiadek, 2011 Acta Biothim Pol 58(4):467-70). Downregulation and/or inactivated of PTPRG has been observed in sporadic and Lynch syndrome colorectal cancer (van Roon E H et al. 2011 Eur J Hum Genet.; 19:307-312), ovarian, breast, and lung cancers (Vezzalini M. et al 2007 50(5):615-28), van Niekerk and Poels 1999 Cancer Letters.; 137:61-73), gastric cancer (Wang J F and Dai D Q. 2007 World J Gastroenterol.; 13:5692-5698), chronic myeloid leukemia (Peruta M et al 2010, Cancer Research; 70:8896-8906), T-cell lymphoma (van Doom R, et al 2005 J Clin Oncol; 23:3886-3896), head and neck cancer and nasoharyngeal cancer (Cheung 2015 Oncotarget. 2015 May 30; 6(15):13434-47).

PTPRG has been shown to be dysregulated and/or mutated in a number of additional disease settings, including schizophrenia (Kranz et al 2015 Schizophr. Res 166(1-3): 119-24) and variants of PTPRG are suggested to act as modifiers of schizophrenia (Docherty 2015 Schizophr Res 164(1-3):181-6). PTPRG has been identified as genetic risk factors in genome-wide association studies (GWAS) in a number of diseases including stroke (Carthy et al 2015 Stroke 46(8):2063-8).

PTPRG has been shown to play a role in hematopoiesis and in humans it is highly expressed in primary and secondary lymphoid tissues and is expressed in peripheral blood monocytes, myeloid and plasmacytoid dendritic cells, including CD34+ precursors, and can affect hematopoietic differentiation (Lissandrini D et al 2006 Blood 108(13)4223-4231).

Leukocyte interaction with the vascular endothelium and recruitment from the circulation to sites of immune responses and inflammation involves a multi-step cascade involving capture, rolling, integrin activation, adhesion, spreading, and transmigration into the tissue. Leukocyte adhesion, or arrest is triggered by chemokines or other chemoattractants and can be mediated by binding of leukocyte integrins to immunoglobulin superfamily members, such as ICAM1 and VCAM1, expressed by endothelial cells. Integrin activation and adhesion are critical steps in leukocyte recruitment (Ley, K, 2007, Nat Rev Immunol 7: 678-689) and pharmacological blockade of leukocyte activation and adhesion can modulate immune responses and reduce inflammation. A number of protein and lipid kinases have been shown to regulate the pro-adhesive signaling network triggered by chemoattractants (Montresor A., et al, 2012, Front Immunol 3: 127). In this context, it was recently shown that protein tyrosine kinases (PTKs) of the JAK family are upstream transducers linking the chemokine receptor CXCR4 to the hierarchical activation of Rho and Rap small GTPases, thus controlling integrin affinity upregulation and homing to secondary lymphoid organs of T-lymphocytes (Montresor, A, et al, 2012, Front Immunol 3: 127). It is clear that leukocyte trafficking is under tight control of phosphorylating events. Notably, leukocyte adhesion is a transient phenomenon showing oscillating dynamics, cycling between adhesion and de-adhesion states propaedeutic to cell crawling, diapedesis and chemotaxis. However, although negative regulators of integrin activation have been described, the mechanisms regulating the on-off dynamics of kinase activity controlling integrin triggering by chemoattractants are unknown.

Methods of manipulating leukocyte activation and recruitment, including monocyte, T cell and neutrophil activation and recruitment, are of interest for clinical and research methods. Macrophages and their precursors, monocytes, are key players of the immune system and reside in every tissue of the body. Upon tissue damage or infection, monocytes are rapidly recruited to tissue where they differentiate into tissue macrophages, including cells such as dendritic cells, microglia, Kupffer cells and osteoclasts. Macrophages are remarkably plastic and can change their functional phenotype depending on their environment and have the ability to clear pathogens, instruct other immune cells, protect the host, regulate homeostasis, but also contribute to the pathogenesis of inflammatory and degenerative disease. Monocytes and macrophages have been demonstrated to be involved in a large number of immune, inflammatory and degenerative clinical settings.

Neutrophils are major effectors in acute inflammation and also are more recently appreciated as key contributors to chronic inflammatory conditions and adaptive immune responses (reviewed in Kolaczkowska and Kubes, 2013, Nature Reviews Immunology 13, 159-175). It is commonly appreciated that neutrophils contribute to the pathogenesis of a number of human inflammatory diseases including, without limitation, chronic obstructive pulmonary disease, inflammatory arthritis and others, and more recently a role in neurological pathology, including Alzheimer's disease (Zenaro E et al 2015 Nature Medicine 21, 880-886) and epilepsy (Fabene P F et al 2008 Nature Medicine 14(12): 1377-1383), and meningitis (Kim J V et al 2009 Nature 457(7226):191-195) have been described.

PTPRG highly expressed in mast cells, a cell type of interest in this invention. Mast cells are a type of granulocyte in the myeloid lineage. Mast cells regulate normal physiological functions, including vasodilation, vascular homeostasis, innate and adaptive immune responses and angiogenesis, and also are implicated in the pathophysiology of many diseases, including asthma, allergy, gastrointestinal disorders, anaphylaxis, many types of malignancies, and cardiovascular disease. Mast cells contain many granules rich in histamine and heparin and are well known for their role in allergy and anaphylaxis. They also play a role in would healing, angiogenesis, immune tolerance, and blood-brain-barrier function. Unlike other hematopoietic cells, mast cells naturally occur in the brain and interact with the neuroimmune system, and may play a role in brain inflammation, neurodevelopmental problems and autism spectrum disorder. Children with autism spectrum disorder often present with allergic-like symptoms in the eabsence of the usual markers of allergy, suggesting a non-allergic mast cell activation, possibly contributing to brain inflammation and neurodevelopmental problems. Mast cells express high levels of PTPRG.

Canonical signaling pathways triggered by many cytokines and growth factors induce autophosphorylation of JAK PTKs on tyrosine (tyr) residues leading to conformational changes and kinase activity up modulation, in turn enabling phosphorylation and activation of transcription factors called STATs (signal transducer of activation of transcription) resulting in gene expression activation via the "JAK-STAT pathway". Moreover, It is now well established that JAK PTKs can be also activated by autophosphorylation by chemokine receptors, such as CXCR4 (receptor for CXCL12, SDF-1 chemokine). SDF-1 (CXCL-12) is expressed in the immune and nervous system and is known to be important in normal hemostasysis and physiology, including in normal neuromodulation, the immune response and nervous system development, as well as in pathology, including multiple sclerosis, Alzheimer's disease, Parkinson disease, AIDS dementia, neuropathic pain, anorexia, depression, and a number of other pathological situations (reviewed in Guyon, A., 2014 Frontiers in Cellular Neuroscience 8:65, 1-10).

In this context, JAK PTKs have been shown to control rho- and rap-dependent signaling modules leading to integrin activation and leukocyte recruitment (Montresor A. et al, 2013 JCB 203(6):1003-19). Several JAK inhibitors are on the market and/or in developed for treatment of a variety of indications, including but not limited to psoriasis, rheumatoid arthritis (RA), ulcerative colitis, myelofibrosis, alopecia areata (Xing L 2014 Nature Med 20, 1043-1049), and hair loss (Harl S. et al, 2015 Sciences Advances: 1(9). Examples include: ruxolitinib (a selective inhibitor of JAK1 and JAK2) for the treatment of myelofibrosis; tofacitinib, (an inhibitor of JAK1 and JAK3; trade name Zeljanz) which is currently approved for treatment of rheumatoid arthritis and is in late-stage clinical trials for psoriasis; and filgotinib, a selective inhibitor of JAK1, which is being developed for RA and Crohn's disease.

Gliomas are a collection of tumors arising from glia or their precursors within the central nervous system. Clinically, gliomas are divided into four grades. Grade IV, glioblastoma multiforme (GBM), is the most common and aggressive primary brain malignancy in adults and one of the most lethal human cancers, representing 30% of all intracranial cancers and 50% of all astrocytomas. Among all astrocytic neoplasms, glioblastomas are characterized by the highest number of genetic alterations (1183 identified genetic anomalies), which, in most cases, result from the accumulation of multiple mutations. In this catastrophic mutational context 158 altered genes encode for protein and lipid kinases and phosphatases, including 52 protein tyrosine kinases, thus potentially leading to dysregulation of several signal transduction pathways. The high degree of intratumoral heterogeneity of GBM is a manifestation of accelerated neoplastic progression in turn leading to unstoppable accumulation of genetic anomalies and emergence of novel phenotypic properties, which facilitate therapy evasion by the neoplasia. This makes GBM an incurable disease with very poor prognosis at this time.

Many advanced solid tumors are genetically complex and many have more than one abnormally activated kinase or signaling pathway. There is also a considerable level of compensatory "cross-talk" between receptors within one signaling pathway as well as between signaling pathways regulating cell proliferation, trafficking, and survival. Despite early successes with tyrosine kinase inhibitors, the majority of responding patients eventually develop resistance to the drugs. In a high fraction of cases, resistance can be traced to selection of cancer cells with secondary mutations in the targeted kinases. The field is currently focused on developing multi-targeted tyrosine kinase inhibitors that can be administered sequentially or as combination therapy to address both the pathogenic heterogeneity, genetic alterations, ongoing process of mutation, acquisition of resistance and selection of cell populations resistant to therapies targeting single or small sets of tyrosine kinase targets.

Thalassemias are a group of congenital anemias characterized by reduced synthesis of one or more of the globins that form hemoglobin; global annual incidence is estimated at 1 in 100,000. They are the most common genetic disorder worldwide. β-thalassemia major is the most clinically relevant form caused by mutations in the HBB gene, inherited in an autosomal recessive fashion. β-thalassemia dyseythropoiesis is characterized by four steps: expansion of erythroid progenitors, accelerated erythroid differentiation until the late, polychromatophilic stage, maturation arrest, and apoptosis at the polychromatophilic stage. Excess alpha-globin chains are present. Decreased or absent β-globin synthesis and the excess of unpaired α-globin chains causes ineffective erythropoiesis and peripheral hemolysis, leading to anemia, bone marrow expansion, hepatosplenomegaly, skeletal deformity and increased gastrointestinal absorption. Standard of care includes routine blood transfusion and intensive iron chelation. In β-thalassemia, ineffective erythropoiesis has been attributed to increased expansion of late erythroid progenitor cells in combination with a limited cell differentiation and accelerated apoptosis. This leads to a net increase in the number of erythroid precursors despite the higher rates of apoptosis due to the formation of toxic hemichromes.

The cytoplasmic domain of the erythropoietin receptor (EpoR) contains a number of phosphotyrosines that are phosphorylated by Jak2 and The JAK2/STAT-5 signal transduction pathway has been reported to play a major role in promoting proliferation and inhibiting differentiation of erythroid progenitor cells (Wojchowski, Sathyanarayana and Dev, 2010 Curr Opin Hematol. 17(3); 169-76). JAK2 is activated by EPO-EPOR interaction and it activates STAT5 through auto and cross-phosphorylation events. STAT5 migrates to the nucleus, activating genes necessary for proliferation, differentiation and survival of erythroid progenitors. Recent data suggest that JAK2 may also have both direct and indirect effects on iron metabolism and that suppressing Jak2 activity could decrease iron uptake by erythrocytes, thereby limiting oxidative damage and reducing hemolysis (Rivella 2012 Blood Rev. 2012 April; 26 Suppl 1:S12-5.) A JAK2 inhibitor, TG101209, administered to healthy and thalassemia mice dramatically decreased the spleen size and ameliorated anemia. (Libani et al 2008 Blood 112(3):875-85) indicating that inhibition of the JAK pathway as a potential approach to treating β-thalassemia.

Dysregulation of the JAK/STAT pathway has been implicated in a number of additional conditions, for example: pulmonary fibrosis, a chronic disease with limited therapeutic options in which a role for JAK/STAT3 pathway has been identified (Prele C M et al. Proc Am Thorac Soc 9: 117, 2012); ischemic myocardial injury, where studies in animal models have shown that modulation of JAK/STAT3 may be protective, reducing cell cardiomyocyte death induced by myocardial infarction and reperfusion injury (Prele C M et al. Proc Am Thorac Soc 9: 117, 2012); prevention of ventilation induced diaphragm mechanical dysfunction, in which the JAK/STAT3 pathway plays a key role in development of diaphragm atrophy and modulators of the JAK/STAT3 pathway have shown beneficial impact (Smith I J et al. FASEB J 28: 2790, 2014; Tang H et al. Mol Med 20: 579-89, 2015); prevention of pulmonary ischemic-reperfusion damages, where general inhibitors of tyrosine kinases affecting the STAT3 pathway have been shown to significantly reduce ischemic-reperfusion induced lung injury, suggesting that tyrosine kinase inhibition/modulation as a possible prophylactic treatment to prevent pulmonary ischemic-reperfusion damage Hierholzer C et al. Arch Orthop Trauma Surg 117: 372, 1998; Oyaizu T et al. Intensive Care Med 38: 894, 2012).

There are currently no specific drugs, reagents, or techniques allowing specific up-modulation of protein tyrosine phosphatase activity in primary cells or tissues or animals, which has significantly hampered investigating the regulatory implications of tyrosine phosphorylation-de-phosphorylation turnover under physiological and/or pathological conditions.

BRIEF SUMMARY OF THE INVENTION

Composition and methods are provided for the specific manipulation of protein tyrosine phosphatase (PTP) activity, including without limitation manipulation of protein tyrosine phosphatase receptor type gamma (PTPRG). The modulation of PTP activity can be performed in vitro or in vivo, and is useful for therapeutic and research purposes. In some embodiments, an effective dose of a PTP modulator is provided to an individual for preventing or treating disease involving dysregulated tyrosine kinase activity, dysregulated tyrosine phosphatase activity, dysregulated phosphoproteome, and/or signaling mechanisms involving tyrosine phosphorylation and/or tyrosine kinase activity. In other embodiments, a PTP modulator is utilized in the analysis and screening of phosphatase pathways in a cell.

Composition and methods are provided for the blockade of leukocyte activation, leukocyte-endothelial interactions (LVI) or trafficking using PTP activating compounds. The compounds of the invention find use for the prevention or treatment of conditions where blockade of leukocyte LVI or or recruitment is beneficial, for example without limitation in inflammatory disease, autoimmune disease and neurodegenerative disease, including without limitation RA, MS, allergy, Alzheimer's disease, IBD, psoriasis, alopecia, epilepsy, reperfusion injury and similar. Composition and methods are provided for the blockade of proliferation and survival and increase in apoptosis of cancer cells and treatment of cancer including, without limitation, glioblastoma multiforme, CML, ALL, T cell lymphoma, ovarian, breast, lung, colorectal, head and neck and nasopharyngeal cancer. Composition and methods are provided for the normalization of hematopoietic differentiation and treatment of hematopoietic disorders including, without limitation, ineffective erythropoiesis, for example beta-thalassemia, myeloproliferative and lymphoproliferative disorders.

In some aspects of the invention, a compound is provided, herein referred to as a PTP activating compound, or PTP activator, which may be a PTP activating polypeptide that specifically increases protein tyrosine phosphatase activity, including without limitation PTPRG activity. Activity can be increased by activation of a PTP, e.g. PTPRG present in a targeted cell. Alternatively activity can be increased by providing an activating polypeptide with phosphatase activity, e.g. that can act directly on PTPRG substrates in the absence of endogenous PTPRG.

In some embodiments, PTP activating polypeptides comprise a "wedge" domain (also referred to as WD), as defined herein. In some embodiments PTP activating polypeptides comprise an intracellular phosphatase domain (IPD). In some embodiments PTP activating polypeptides comprise an intracellular domain (ICD). In some embodiments a wedge, IPD or ICD domain is operably linked to a "transport" or "permeant" domain that allows transport of the polypeptide across the cell membrane. Such polypeptides may be referenced herein as a "permeant wedge domain", "permeant IPD domain" or "permeant ICD domain". The operable linkage may be a chemical linkage, direct fusion of the polypeptides, fusion of the polypeptides through a polypeptide linker, and the like.

In some embodiments, a wedge domain comprises or consists essentially of a sequence corresponding to amino acid residues 831-856 of human PTPRG, which is also provided herein as SEQ ID NO:1. In some embodiments an ICD domain comprises or consists essentially of amino acid residues 797-1445 of human PTPRG, which is also provided herein as SEQ ID NO:6. In some embodiments an IPD domain comprises or consists essentially of amino acid residues 846-1445 of human PTPRG, which is also provided herein as SEQ ID No 7. The ICD domain, which comprises the IPD domain, is shown herein to have direct phosphatase activity on PTPRG substrates.

In some embodiments the PTP activating polypeptide comprises a soluble extracellular domain of a protein tyrosine phosphatase, referred to herein as "PTPx". In some embodiments a PTPx polypeptide comprises or consists essentially of a sequence corresponding to amino acid residues 20-736 of human PTPRG, which is also provided herein as SEQ ID NO:8. Analog and derivatives of such a construct also find use in the methods of the invention.

In other embodiments a PTP activating compound is a small molecule that mimics the activity of a wedge, ICD, IPD or PTPx domain. In other embodiments the phosphatase activating mimetic is a monoclonal antibody directed at, without limitation, the PTPx domain. Such mimetic compounds are identified by screening methods as described herein.

In some embodiments, the PTP activator, e.g. ICD, permeant ICD, PTPx, permeant PTPx, wedge domain, permeant wedge domain, IPD, permeant IPD, analog, derivative or mimetic thereof, is provided as a pharmaceutical composition, e.g. in a pharmaceutically acceptable excipient. The pharmaceutical formulation is optionally provided in a unit dose formulation, where a dose is effective in the desired activation or increase in activity of PTPRG. The present invention is based, in part, on the discovery that activation of PTPRG acts as a negative regulator of signaling mechanisms controlling, for example, integrin activation and leukocyte adhesion. In some embodiments the integrin activation is chemoattractant-induced LFA-1 affinity triggering. The present invention is based, in part, on the demonstration that contact of leukocytes, including T cells, monocytes and neutrophils, with an effective dose of agents of the invention, can block chemoattractant-induced activation and/or adhesion of these cells.

The compounds of the invention find use as anti-inflammatory agents, e.g. in the inhibition of leukocyte adhesion, leukocyte-vascular interactions, or recruitment, and specifically monocyte, T cell, neutrophil, dendritic cell, eosinophil and mast cell adhesion. The compounds may be used in the treatment of conditions where blockade of leukocyte-vascular interactions, leukocyte trafficking or recruitment is beneficial, e.g. in conditions characterized by undesirable leukocyte trafficking activity, e.g. inflammatory disease, autoimmune disease, and neurodegenerative disease, including without limitation, RA, psoriasis, MS, IBD, graft v host disease, allergy and IBD. In some embodiments leukocyte trafficking or leukocyte-vascular interactions are used to prevent or treat neuroinflammatory diseases, including without limitation Alzheimer's disease, epilepsy and other conditions associated with seizure, and the like.

Methods of the invention include, without limitation, contacting a population of cells, e.g. a population of leukocytes comprising lymphoid or myeloid cells, including without limitation monocytes, lymphocytes, granulocytes, e.g. neutrophils, eosinophils and basophils, dendritic cells, and/or mast cells, with an effective dose of a PTP activator of the invention, wherein the effective dose is sufficient to block, without limitation, leukocyte adhesion, recruitment, activation, or triggering of integrins such as LFA-1 to a high affinity state.

Some embodiments include prevention or treatment of autoimmune disease, including without limitation, IBD, psoriatic arthritis, psoriasis, RA, autoimmune arthritis, MS, retinopathy, myocarditis, endocarditis, lupus, alopecia areata, angioedema, uticaria, scleroderma, and vasculitis. Other embodiments include prevention or treatment of inflammatory conditions or diseases including, without limitation, atopic allergy, asthma, celiac disease, IBD, pelvic inflammatory disease, reperfusion injury, transplant rejection, vasculitis, alopecia, cystitis, acne, atherosclerosis, and atopic dermatitis.

The therapeutically effective dose for the prevention or treatment of inflammatory and autoimmune diseases may be monitored by assessing, without limitation, the number, morphology, degranulation, apoptosis, adhesive status, aggregation, integrin affinity status, activation status, phosphotyrosine phosphatase activity, phosphotyrosine kinase activity, or PTPRG activity in the target cell populations in the blood or relevant tissue. The PTPRG activity can be monitored directly or indirectly by monitoring the phosphorylation status of PTPRG targets, for example without limitation JAK2, or the phosphoproteome signature. Further, an effective dose can be monitored by assessing biomarkers of inflammation, including without limitation, markers of inflammation, vascular injury, endothelial activation, leukocyte-vascular interaction, leukocyte activation, or tissue damage, for example without limitation, soluble/shed adhesion receptors or ligands, C-reactive protein, cytokines, chemokines, lipoxins, reactive oxygen species and leukotrienes. In addition, an effective dose can be monitored by assessing pain, swelling, fever, and clinical assessment of typical symptoms of the condition or disease.

Some embodiments include contact of a target population of cells with an effective dose of an agent of the invention for the prevention or treatment of neurological or neuroinflammatory disease including, without limitation, Alzheimer's disease, dementia, epilepsy, refractory epilepsy, status epilepticus, traumatic brain injury, schizophrenia, autism spectrum disorders and behavior disorders. In such embodiments, an effective dose of an agent of the invention can be monitored as described for the target population or blood levels of inflammatory biomarkers as described for treatment of inflammatory and autoimmune diseases. Further, an effective dose of an agent of the invention in neurological conditions may be monitored by assessing biomarkers of brain injury, blood brain barrier integrity, synaptic degeneration, glial cell activation and neurodegeneration in blood, brain or cerebrospinal fluid for example, without limitation S100Beta, neuro-specific enolase, glial fibrillary acidic protein, E- and P-Selectin, synaptotagamin, ABeta, neutrophil/T cell ratio, and phosphorylated tau. In some embodiments efficacy can be monitored by assessing, for example without limitation, seizure activity, behavior and cognition, and related specific clinical assessments, known for each condition or disease.

The present invention is based, in part, on the discovery that treatment of glioblastoma cells with PTPRG WD or ICD results in a time- and dose-dependent blockade of cell survival and cell proliferation; and a triggering of cancer cell apoptosis. Methods of the invention include, without limitation, contact of a target cell population with an effective dose and regimen of an agent of the invention to treat cancer, including without limitation carcinoma, sarcoma or gliomas. In some indications the carcinomas to be treated including without limitation glioblastoma multiforme, head and neck cancer, nasopharyngeal carcinoma, ovarian, breast, lung, colorectal, prostate, and gastric cancer. A therapeutically effective dose may be monitored by for example, without limitation, assessing the survival, apoptotis, proliferation, phosphotyrosine phosphatase activity, phosphotyrosines kinase activity, or PTPRG activity, measured directly or indirectly, or the phosphoproteome signature and additional biomarkers of the cancer cells in vitro or in vivo. In some of these embodiments the effective dose is be monitored using standard clinical assessments for a given cancer, including without limitation, assessing the size, growth or metabolic status of the tumor, standard medical diagnostic imaging, tumor biomarkers in blood, urine, ascites, sputum, ductal secretions, cerebrospinal fluid or other tissues.

In some embodiments the target population of cells are hematopoietic cancer cells in a patient suffering from a hematological neoplasms, also called tumors of the hematopoietic and lymphoid tissue, which affect the blood, bone marrow, lymph and lymphatic system. Hematological neoplasms can be lymphoproliferative or myeloproliferative disorders. Lymphoproliferative disorders, including without limitation: multiple myeloma; leukemia, include acute lymphoblastic leukemia (ALL), acute myelogenous leukemia (AML), chronic lymphocytic leukemia (CLL), chronic myelogenous leukemia (CML), acute monocytic leukemia (AML) and others; and lymphomas, including Hodgkin's and non-Hodgkin's lymphoma. Myeloproliferative neoplasms include, without limitation: chronic myelogenous leukemia, polycythemia vera, myelofibrosis, essential thrombocytosis and eosinophilic leukemia. A therapeutically effective dose of an agent of the invention may be monitored by, for example without limitation, assessing reduction of the number of tumor cells remaining in the blood, bone marrow, lymph nodes, CSF or other tissues or exudates. A therapeutically effective dose may also be monitored by for example, without limitation, assessing the survival, apoptotis, proliferation, phosphotyrosine phosphatase activity, phosphotyrosines kinase activity, or PTPRG activity, measured directly or indirectly, or the phosphoproteome signature and additional biomarkers of the cancer cells in vitro or in vivo. In addition, an effective dose can be monitored using standard clinical assessments for a given cancer, including without limitation, assessing the size, growth or metabolic status of the tumor, standard medical diagnostic imaging, tumor biomarkers in blood, urine, ascites, sputum, ductal secretions, cerebrospinal fluid or other tissues.

In some embodiments, an effective dose of an agent of the invention may be used alone or in combination with other therapeutic drugs or treatments.

In some embodiments, monitoring may be performed prior to treatment and may be performed at intervals during the course of the treatment. Methods recited herein may be carried out in any order of the recited events.

In some embodiments, the PTP activator, e.g. wedge domain, permeant wedge domain, analog, derivative or mimic thereof, or the ICD, permeant ICD, analog, derivative or mimic thereof, or the PTPx, analog, derivative or mimic thereof, is provided as a pharmaceutical composition for the treatment of glioblastoma multiforme or other cancers in which PTPRG or its targets are dysregulated, including specifically and without limitation: breast cancer; chronic myeloid leukemia (CML); childhood acute lymphoblastic leukemia (ALL); nasopharyngeal carcinoma. PTP activators can also be provided as a pharmaceutical composition for the treatment of neoplastic diseases or other PTPRG target-related disease, that do not express PTPRG but that show multiple kinase mutations leading to a dysregulated kinome, which diseases benefit from the methods of the invention where phosphatase activity is increased, therein countering undesirable kinase activity.

The present invention is also based, in part, on the discovery that in vivo treatment of a mouse model of beta-thalassemia with PTPRG ICD ameliorates beta-thalassemic anemia, including but not limited to normalization of key hematological parameters and red cell indices, reduction of abnormal circulating erythroblasts, reduction of abnormal levels of reactive oxygen species, and normalization of differentiation in bone marrow.

Methods of the invention are provided to contact erythroid progenitor cells with an effective dose of an agent of the invention in an individual suffering from ineffective erythropoiesis, wherein the effective dose is sufficient to normalize the production of erythrocytes and related hematological markers in the bone marrow and blood. Some embodiments include treatment of conditions of ineffective erythropoiesis including without limitation thalassemia, beta-thalassemia or Diamond-Blackfan anemia and the like. The therapeutically effective dose may be monitored by assessing hematological markers, e.g. hematocrit, reticulocyte count, circulating erythroblasts, spleen size, levels of hemoglobin, beta globin chains, hemoglobin tetramer, alpha globin chains and the ratio of alpha to beta globin chains in blood cells, number and maturation status of erythroid progenitor subpopulations in the bone marrow, and reduced requirement for blood transfusion and iron chelation for the patient. In these embodiments the agents of the invention may be used alone or in combination with other therapeutic interventions.

Myelodysplastic syndromes are additional hematological disorders of the hematopoietic stem cells in the bone marrow related to the myeloid lineage with ineffective production or dysplasia of all myeloid blood cells. Myelodysplastic syndromes include, without limitation, refractory cytopenia, refractory anemia with ring sideroblasts, refractory cytopenia with multilineage dysplasia, refractory anemia with excess blasts, refractory anemia with excess blasts in transformation, and chronic myelomonocytic leukemia. Methods of the invention are provided to contact hematopoietic stem cells and myeloid progenitor cells with an effective dose of an agent of the invention in patients suffering from myelodysplastic syndromes, wherein the effective dose is sufficient to normalize production of myeloid cells or percent of myeloblasts in bone marrow.

In other embodiments the polypeptide activators of the invention are used in rational drug design and/or screening assays to identify candidate compounds with phosphatase activation or phosphatase activity.

In other embodiments, the PTP activators of the invention are used in developing a map of the phospho-proteome signature of a cell for use in research and screening. Such embodiments may include contacting a population of cells, e.g. tumor cells, hematopoietic cells, leukocytes, etc., for example primary human monocytes, with an effective dose of a PTP activator of the invention. The phosphorylation or activity of targeted proteins is measured before and after the contacting. Such measurement can be performed by any convenient assay, e.g. flow cytometry, mass cytometry, Western blot, enzyme activity, phospho-cite chip analysis etc., in which specific phosphorylation states are determined. The contacting may be performed in combination with a second agent, e.g. a chemoattractant, drug, environmental change, etc., to determine the effect on the resulting phospho-proteome. Such a signature pattern is useful, for example, in the identification of targets of PTPs, identification of mimetic drugs, as well as determining the effect of drugs, chemokines, hormones, environmental changes and the like.

DETAILED DESCRIPTION OF THE EMBODIMENTS

The present invention is based, in part, on the discovery that increasing activity of PTPRG acts as a negative regulator of signaling mechanisms controlling integrin activation, such as chemoattractant-induced LFA-1 affinity triggering and integrin mediated adhesion in human cells, including human primary monocytes, lymphocytes and neutrophils. In some embodiments a PTPRG modulating agent, e.g. an activator agent or catalytic agent, is contacted with a population of cells in vitro or in vivo for the purpose of altering LFA-1 affinity triggering and/or altering leukocyte adhesion, leukocyte-endothelial interaction and trafficking.

The present invention is also based, in part, on the discovery of a PTPRG-specific polypeptide sequences, e.g. a wedge domain, IPD or ICD domain, which, when delivered to a cell using a permeant domain, or the external domain (PTPx) delivered to a cell as a soluble agent, specifically activates PTPRG and blocks adhesion triggered by chemoattractants in human monocytes and T-lymphocytes in flow based and static adhesion settings. The present invention is also based, in part, on the discovery that a PTPRG-specific sequence with intrinsic PTPRG activity, e.g. an ICD domain, when delivered to a cell using a permeant domain, can block adhesion triggered by chemoattractants in human neutrophils. Also included in the invention are mimetics and variants of such sequences.

Composition and methods are provided to increase PTPRG enzymatic activity, e.g. to activate PTPRG in screening and mapping assays. Such mapping of the phosphor-proteome allows for the screening, identification, and characterization of agents for therapeutic use. The 'signature' can be used to identify specific targets or groups of targets for therapeutic intervention. For example, activation of PTPRG in human monocytes results in a specific, complex alteration in the phospho-proteome that allowed for the identification of Src as the most connected and central signaling protein in the network, followed by KIT, PTK2, ITGB1, STAT1, EGFR, PDGFRB, ABL1 and TBK, demonstrating that Src family kinases are a main functional target of PTPRG activity, and thus that PTPRG activation is useful to treat disorders involving dysregulation of Src family kinases.

It is also demonstrated herein that JAK2 is a PTPRG target. It was previously known that JAK2 mediates LFA-1 affinity triggering and adhesion by chemoattractants in human primary monocytes and that JAK2 inhibitors, are useful agents to reduce monocyte trafficking. Herein we show that PTPRG WD, ICD and PTPx can block monocyte LFA-1 affinity triggering and adhesion and are thus useful therapeutics to treat indications where reduction of leukocyte adhesion and vascular interaction is needed.

The extracellular region (ER) of PTPRG (PTPx) can be exploited to trigger PTPRG monomerization and enzymatic activation. PTPx, encompassing the entire PTPRG ER, including the alpha-carbonic anhydrase domain (CA) and the fibronectin type III domain (FBN) domains, was generated by in vitro translation and used to characterize its role in leukocyte adhesion regulation. PTPx treatment of human monocytes inhibited integrin activation and dependent adhesion by chemoattractants in similar way to P1-WD and TAT-ICD. PTPRG ER can work as an outside wedge tool leading to PTPRG momomerization. PTPx or derivatives thereof are used for screening and discovery and therapeutics to prevent or treat disease involving an altered phosphoproteome, dysregulated tyrosine kinase activity, tyrosine phosphatase activity and/or signaling mechanisms involving tyrosine phosphorylation, including β-thalassemia.

Definitions

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are herein described.

A "vector," as used herein, refers to a recombinant plasmid or virus that comprises a nucleic acid to be delivered into a host cell, either in vitro or in vivo.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—$NH_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

"Percent (%) sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software programs, for example, those described in Current Protocols in Molecular Biology (Ausubel et al., eds., 1987), Supp. 30, section 7.7.18, Table 7.7.1, and including BLAST, BLAST-2, ALIGN or Megalign (DNASTAR) software. A preferred alignment program is ALIGN Plus (Scientific and Educational Software, Pennsylvania). Those skilled in the art can determine appropriate parameters for measuring alignment, including any algorithms needed to achieve maximal alignment over the full length of the sequences being compared. For purposes herein, the amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows: 100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

An "isolated" molecule (e.g., nucleic acid or protein) or cell means it has been identified and separated and/or recovered from a component of its natural environment. In some embodiments a polypeptide used in the methods of the invention is utilized as an isolated fragment, i.e. a sequence isolated or separated from the naturally occurring protein from which it is derived. Such a fragment can be synthesized by recombinant methods or by in vitro synthesis, and the term "isolated" is such embodiments refers to a peptide that is free of sequences with which it would be associated in the native protein. The term does not require an actual separation step from components of the native protein. Such an "isolated fragment" can be fused to a permeant domain, an Fc region, PEG, etc.

An "effective amount" is an amount sufficient to effect beneficial or desired results, including clinical results. An effective amount can be administered in one or more administrations. In terms of a disease state, an effective amount is an amount sufficient to ameliorate, stabilize, or delay development of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Leukocyte recruitment" is also known as leukocyte trafficking is a multistep process involving rolling, activation, sticking, spreading, adhesion and diapedesis of a leukocyte into a tissue resulting in a temporary increased localization of leukocytes in a tissue "Leukocyte-vascular interaction" or LVI is defined herein as the interaction of circulating leukocytes with the endothelium. Blood leukocytes roll and interact on the vascular endothelium and interactions are rapidly enhanced by even modest local tissue damage or systemic inflammatory events. These interactions, even without extravasation of the leukocytes, can signal the endothelium and can trigger endothelial activation, cytokine production or alter junctional interactions facilitating, for example, leakage of plasma proteins and ion, which may play a key role in seizure susceptibility and to epileptogenesis.

PTPRG. Receptor-type tyrosine-protein phosphatase gamma is a member of the protein tyrosine phosphatase (PTP) family. PTPs are known to be signaling molecules that regulate a variety of cellular processes including cell growth, differentiation, mitotic cycle, and oncogenic transformation. This PTP possesses an extracellular region, a single transmembrane region, and two tandem intracytoplasmic catalytic domains. The extracellular region of this PTP contains a carbonic anhydrase-like (CAH) domain, which is also found in the extracellular region of PTPRBETA/ZETA. See Genbank accession number NP_002832 for the human reference sequence.

A PTPRG wedge domain is a polypeptide corresponding to the amino acid residues 831-856 of human PTPRG, which is also provided herein as SEQ ID NO:1. An ICD domain comprises or consists essentially of amino acid residues 797-1445 of human PTPRG, which is also provided herein as SEQ ID NO:6 The IPD domain is a polypeptide corresponding to the amino residues 846-1445 of human PTPRG, which is also provided herein as SEQ ID No 7. The PTPRG extracellular domain (PTPx) is a polypeptide corresponding to the amino acid residues 20-736 of human PTPRG, which is also provided herein as SEQ ID No. 8. The ICD, IPD, wedge, and PTPx sequences may be collectively referred to PTPRG activating polypeptides or PTPRG activators.

The PTPRG ICD contains constitutive PTP activity and can both activate endogenously expressed PTPRG in cells and tissues, can also act on specific PTPRG substrates in cells and tissues that do not express PTPRG.

For use in the methods of the invention, either of the ICD, IPD, wedge, or PTPx domains, fusion proteins thereof, modifications thereof, or a combination of forms may be used, as well as chemical mimetics agonists and antagonists thereof. Peptides of interest include fragments of at least about 12 contiguous amino acids, at least about 20 contiguous amino acids, at least about 30 contiguous amino acids, at least about 50 contiguous amino acids, at least about 75 contiguous amino acids, at least about 100 contiguous amino acids, at least about 200 contiguous amino acids, at least about 300 contiguous amino acids, at least about 400 contiguous amino acids, at least about 500 contiguous amino acids, at least about 600 contiguous amino acids, at least about 700 contiguous amino acids, up to the provided polypeptide, and may extend further to comprise other sequences present in the precursor protein.

Amino acid sequence variants of PTP activator proteins provided herein are also contemplated. For example, binding affinity and/or other biological properties can be improved by altering the amino acid sequence encoding the protein. Amino acids sequence variants can be prepared by introducing appropriate modifications into the nucleic acid sequence encoding the protein or by introducing the modification by peptide synthesis. Such modifications include, for example, deletions from, insertions into, and/or substitutions within the amino acid sequence. Any combination of deletion, insertion, and substitution can be made to arrive at the final amino acid construct, provided that the final construct possesses the desired characteristics. Accordingly, provided herein are variants of a PTP activator protein. In some embodiments, variants comprise an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of any one of the provided PTP activator polypeptides, where, for example, the variant may include 1, 2, 3, 4, 5, 6, 7, 8, 9, 10 amino acid substitutions or changes relative to the provided sequence.

Modifications and changes can be made in the structure of the polypeptides and proteins of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's or protein's biological functional activity, certain amino acid sequence substitutions can be made in a polypeptide or protein sequence and nevertheless obtain a polypeptide or protein with like properties.

Amino acid substitutions are generally based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include, but are not limited to (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure, therefore, consider functional or biological equivalents of a polypeptide or protein as set forth above. In particular, embodiments of the polypeptides and proteins can include variants having about 50%, 60%, 70%, 80%, 90%, and 95% sequence identity to the polypeptide and protein of interest.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) *J. Biol. Chem.* 275:23783-23789). Analogs of such polypeptides include those containing residues other than naturally occurring L-amino acids, e.g. D-amino acids or non-naturally occurring synthetic amino acids.

As an option to recombinant methods, polypeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of polypeptides of the invention protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993). Proteins or peptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) J. Med. Chem. 41: 2481-91; Xie and Schultz (2005) Curr. Opin. Chem. Biol. 9: 548-554; Hodgson and Sanderson (2004) Chem. Soc. Rev. 33: 422-430.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Transport or permeant domains. A number of transport domains are known in the art and may be used in the present invention, including peptides peptidomimetics, and non-peptide carriers. In one embodiment the transporter peptide is derived from the third alpha helix of *Drosphila melanogaster* transcription factor Antennapaedia, refered to as penetratin, which comprises the AA sequence RQIKIWFQNRRMKWKK (SEQ ID NO: 4).

In another embodiment, the transport peptide comprises the HIV-1 tat basic region AA sequence, which may include, for example, AAs 49-57 of naturally-occurring tat protein. Other transport domains include poly-arginine motifs, for example, the region of AAs 34-56 of HIV-1 rev protein (See for example Futaki et al. (2003) Curr Protein Pept Sci. 2003 April; 4(2): 87-96; and Wender et al. (2000) Proc. Natl. Acad. Sci. U.S.A 2000 Nov. 21; 97(24): 13003-8; published U.S. Patent applications 20030220334; 20030083256; 20030032593; and 20030022831, herein specifically incorporated by reference for the teachings of translocation peptides and peptoids). (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The attachment of the PTPRG activation domain to the transport domain may utilize any means that produces a link between the constituents that is sufficiently stable to withstand the conditions used, and that does not alter the function of either constituents. The PTP activator and permeant domains may be linked by a linking moiety such as a peptide linker, or the two domains may be directly fused. In some embodiments, the peptide linker comprises 1 to 100 amino acids. In some embodiments, the peptide linker comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 but no greater than 100 amino acids. In some embodiments, the peptide linker is between 5 to 75, 5 to 50, 5 to 25, 5 to 20, 5 to 15, 5 to 10 or 5 to 9 amino acids in length. Exemplary linkers include linear peptides having at least two amino acid residues such as Gly-Gly, Gly-Ala-Gly, Gly-Pro-Ala, Gly-Gly-Gly-Gly-Ser. Suitable linear peptides include poly glycine, polyserine, polyproline, polyalanine and oligopeptides consisting of alanyl and/or serinyl and/or prolinyl and/or glycyl amino acid residues.

In one embodiment a linker comprises the amino acid sequence (GGGGS)n, where n is 1, 2, 3, 4, 5, etc.; however many such linkers are known and used in the art and may serve this purpose.

Alternatively, a suitable chemical linker group may be used. A linker group can function as a spacer to distance two polypeptide domains in order to avoid interference with binding capabilities. A linker group can also serve to increase the chemical reactivity of a substituent on a moiety or a polypeptide, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the polypeptide moiety) and succinimidyl linkers (which react with a primary amine on the polypeptide moiety). Several primary amine and sulfhydryl groups are present on a polypeptide, and additional groups may be designed into recombinant molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, the polypeptides may be coupled through an oxidized carbohydrate group at a glycosylation site, as described in U.S. Pat. Nos. 5,057,313 and 5,156,840. Yet another alternative method of coupling polypeptides is by the use of a non-covalent binding pair, such as streptavidin/biotin, or avidin/biotin. In these embodiments, one member of the pair is covalently coupled to a polypeptide and the other member of the binding pair is covalently coupled to the cytotoxic or imaging moiety.

The polypeptide may be labeled, either directly or indirectly. Any of a variety of suitable labeling systems may be used, including but not limited to, radioisotopes such as $^{125}$I; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library. Other polypeptide tags of interest include birA, sortase, etc. as known in the art.

Alternatively the compounds of the invention may be formulated in a nanocarrier. As used herein, the term "nanocarrier" refers to particles of varied size, shape, type and use, which are further described herein. As will be appreciated by one of ordinary skill in the art, the characteristics of the nanocarriers, e.g., size, can depend on the type and/or use of the nanocarrier as well as other factors generally well known in the art. In general, nanocarriers can range in size from about 1 nm to about 1000 nm. In other embodiments, nanocarriers can range in size from about 10 nm to about 200 nm. In yet other embodiments, nanocarriers can range in size from about 50 nm to about 150 nm. In certain embodiments, the nanocarriers are greater in size than the renal excretion limit, e.g., greater than about 6 nm in diameter. In other embodiments, the nanocarriers are small enough to avoid clearance from the bloodstream by the liver, e.g., smaller than 1000 nm in diameter. Nanocarriers can include spheres, cones, spheroids and other shapes generally known in the art. Nanocarriers can be hollow (e.g., solid outer core with a hollow inner core) or solid or be multi layered with hollow and solid layers or a variety of solid layers. For example, a nanocarrier can include a solid core region and a solid outer encapsulating region, both of which can be cross-linked. Nanocarriers can be composed of one substance or any combination of a variety of substances, including lipids, polymers, silica, magnetic materials, or metallic materials, such as gold, iron oxide, and the like. Lipids can include fats, waxes, sterols, cholesterol, fat-soluble vitamins, monoglycerides, diglycerides, phospholipids, spingolipids, glycolipids, cationic or anionic lipids, derivatized lipids, cardiolipin and the like. Polymers can include block copolymers generally, poly(laciic acid), poly(lactic-co-glycolic acid), polyethylene glycol, acrylic polymers, cationic polymers, as well as other polymers known in the art for use in making nanocarriers. In some embodiments, the polymers can be biodegradable and/or biocompatible. Nanocarriers can include a liposome, a micelle, a lipoprotein, a lipid—coated bubble, a block copolymer micelle, a polymersome, a niosome, a quantum dot, an iron oxide particle, a gold particle, a dendrimer, or a silica particle. Irs certain embodiments, a lipid monolayer or bilayer can fully or partially coat a nanocarrier composed of a material capable of being coated by lipids, e.g., polymer nanocarriers. In some embodiments, liposomes can include multilamellar vesicles (MLV), large unilamellar vesicles (LUV), and small unilamellar vesicles (SUV).

Leukocyte Trafficking.

Most mature leukocytes continuously circulate between the blood and lymphatic organs. Leukocytes leave the blood by recognizing and binding to the vascular endothelial cells. Thereafter, they migrate between the endothelial cells into the surrounding tissues. Leukocyte trafficking allows the full repertoire of immunological specificities to be available for immune reactions throughout the body, and it also facilitates the cell-cell interactions required for the generation and control of immune responses. Trafficking also controls the location of leukocytes during development and differentiation, for example in the movement of lymphocytes from the bone marrow to the thymus, the bone marrow homing of stem cells, etc.

Leukocyte adherence to endothelial cells is dependent on interactions between complementary adhesion molecules expressed on both cell types. Normally, this binding is to specialized postcapillary venules called high endothelial venules (HEV). Functionally distinct leukocyte-HEV recognition systems mediating migration to peripheral lymph nodes, mucosal lymphoid organs, synovium, skin and lung-associated lymphoid tissues in an organ-specific manner have been described.

The process of trafficking, (or homing) is believed to consist of a number of discrete steps, including migration of cells to a targeted tissue, e.g. by chemotaxis. The leukocytes roll along the endothelium, until delivery of a triggering signal that activates leukocyte integrins. The integrin activation step results in establishment of strong adhesion to the endothelium. Shortly after adhesion, the leukocytes enter the extra-vascular space though endothelial cell-cell junctions.

The ability of leukocytes, e.g. monocytes, neutrophils, lymphocytes, etc. to leave the circulation depends on their activation state. Activation occurs during rolling, when leukocytes encounter chemoattractants, e.g. C5a, platelet activating factor, leukotriene $B_4$, formyl peptides, and chemoattractant cytokines, e.g. chemokines. Chemokines bind to specific leukocyte receptors that trigger heterotrimeric G-protein-dependent leukocyte signaling. Such signals lead to clustering, and greater affinity/avidity of the integrins, including LFA-1, Mac-1, and VLA-4 for their cognate Ig-superfamily EC-CAMs. Other intracellular events signaling activation are induced in leukocytes during E-selectin tethering, VLA-4 cross-linking, or LFA-1 binding to ICAM-1.

Cells of interest for the present methods include, without limitation, myeloid leukocytes, including neutrophils, basophils, eosinophils, mast cells, monocytes and myeloid dendritic cells, and lymphoid leukocytes, including T and B cells, NK cells and lymphoid dendritic cells. The administration of agents that increase PTPRG activity decreases the activation, adhesion, leukocyte-vascular interactions and trafficking of leukocytes to sites of inflammation.

The mononuclear phagocyte system is comprised of both circulating and fixed populations of cells. The circulating component is the monocyte. Upon migration into tissues these are referred to as histiocytes or tissue macrophages. The major fixed macrophages include: Sinusoidal lining cells of the spleen, lymph nodes, liver, and bone marrow; connective tissue histiocytes; mobile macrophages on serosal surfaces; alveolar macrophages within the lung; microglia in the nervous system; and mesangial macrophages within renal glomeruli. Macrophages produce a variety of substances that are involved in inflammation.

The protein tyrosine phosphatase (PTP) superfamily of enzymes acts in a coordinated manner with protein tyrosine kinases to control signaling pathways that regulate a broad spectrum of fundamental physiological and pathological processes including differentiation, proliferation, apoptosis, survival, migration, activation, adhesion and invasion of many cell types, which are relevant to many human diseases including, without limitation, inflammation, hematopoiesis, neuroinflammation, erythropoiesis, and cancer, In some embodiments of this invention an effective dose of a PTP activating agent is used to treat an individual with cancer. Cancers of interest for the methods of this invention include cancers classified as carcinomas, sarcomas, lymphomas and hematopoietic/leukemias, and gliomas.

Carcinomas of interest for this invention include, without limitation, breast, ovarian, lung, gastric, pancreatic, and colorectal cancers, basal and squamous cell carcinoma, ductal carcinoma in situ, head and neck cancer, and adenocarcinoma. Sarcomas of interest include, without limitation, myeloid sarcoma, osteosarcoma, and histiocytic sarcoma. Gliomas include, without limitation, astrocytomas and Glioblastoma multiforme.

Glioblastoma multiforme (GBM), also known as glioblastoma and grade IV astrocytoma, is the most common and aggressive malignant primary brain tumor. Approximately 50% of patients diagnosed with GBM die within one year and 90% within three years. The median survival with standard-of-care radiation and chemotherapy is 15 months. This extremely poor prognosis is mainly dependent of a number of factors: GBM cells are very resistant to conventional therapies; the brain is susceptible to damage due to conventional therapy; the brain has a very limited capacity to repair itself; and finally, many drugs cannot cross the blood-brain barrier to act on the tumor. Furthermore, GBM is characterized by a very high mutational rate, with at least 1183 identified genetic anomalies to date. The high degree of intratumoral heterogeneity of GBM is a manifestation of accelerated neoplastic progression in turn leading to unstoppable accumulation of genetic anomalies and emergence of novel phenotypic properties, which facilitate therapy evasion by the neoplasia, thus greatly worsening the prognosis.

Signaling networks are characterized by a high degree of concurrency. Concurrency implies that many signaling molecules participate together to the regulation of specific cell functionality, each one contributing to reach a defined threshold of signal necessary to generate the final output. This makes the molecular circuitry more important than individual proteins. Here, redundancy may also emerge as a property of signaling networks, with the role of individual signaling proteins partially or fully compensated by other molecules. Neoplastic transformation is, essentially, signal transduction pathology. In this context, multiple gene mutations affecting several signaling proteins at once may generate consistent level of redundancy. Although drugs targeting individual oncogenes have been proven useful in some type of cancers, such as in leukemia, the complexity of signaling network dysregulated in solid tumors generates high level of redundancy, greatly facilitating the emergence of compensatory events in signaling networks, thus leading to cell adaption and therapy evasion during cancer progression. This makes monotargeted therapies prone to failure and disease relapse. Targeting an upstream regulator of multiple targets capable of modulating the signaling network, such as a tyrosine phosphatase, including PTPRG, can offer significant advantages over traditional single/small number of targets.

In some embodiments of this invention the target cells are contacted with a PTP activating agent to increase PTP activity in an individual suffering from a condition known in the art or shown in the literature to be associated with a defect in the expression or function of PTPRG or any of its key downstream targets, for example with out limitation, JAK2. In these embodiments a very small increases in enzyme activity may be sufficient to cause meaningful biological alterations and clinical responses for several key reasons. First, PTPRG and as many of its targets are catalytic enzymes, signaling proteins, receptors and transcription factors that serve in regulatory roles in sensitive, amplifying signaling pathways that regulate the cellular functions of interest. Second, the functions of target proteins are exquisitely regulated by tyrosine phosphorylation. In these embodiments PTPRG activity can be monitored directly or indirectly. In some embodiments PTPRG activity is measured directly using specific enzyme assays known in the art and an effective dose is defined as an increase of at least about 1%, at least about 5%, at least about 10%, or more.

In other embodiments PTPRG activity is measured indirectly by measuring the difference in tyrosine phosphorylation of selected PTPRG target proteins in the treated tissue or cell compared to untreated tissues or cells or normal tissues or cells using standard methods in the art. In some embodiments PTPRG activity can be monitored by comparing the phosphoproteome signature of the treated cells, or tissue with untreated or normal cells or tissues. In these embodiments, an effective dose is as one that alters the tyrosine phosphorylation of one or more target proteins by at least about 5%, or at least about 10% or at least about 20% or at least about 50%, or more.

In some embodiments the PTPRG activity is measured indirectly using functional assays including but not limited to: activation, measured by secretion of enzymes, cytokines, ROS, chemokines, growth factors, histamine; signaling, measured using calcium flux and the like; morphology; degranulation; upregulation of cell surface markers of activation; adhesiveness, measured by integrin affinity state, aggregation, binding to solid phase, soluble, or transfectant-espressed adhesion molecules in flow or static assays, binding to cells, including without limitation, platelets, or endothelial cells, antigen-presenting cells and the like; proliferation; or apoptosis. In some embodiments an effective dose is measured by assessing leukocyte recruitment into a tissue of interest. In chronic inflammatory conditions, such as MS, IBD, RA and the like, or in acute inflammation, such as reperfusion injury or flare of MS, IBD or RA an effective dose decreases leukocyte recruitment is decreased by at least about 50%, at least about 65% at least about 80% or more, where recruitment may optimally be measured, for example, by quantitation of leukocytes in an affected tissue, such as CSF, with a lesion, synovial fluid, skin, sputum, ascites and the like. In indolent, slow, progressive conditions conditions and some neuroinflammatory conditions, such as without limitation Alzheimer's disease and epilepsy, an effective dose is one that decreases leukocyte recruitment and leukocyte-vascular interactions by at least about 10%, at least about 25 at least about 50%, or more.

In some embodiments cells or tissues to be assayed can be collected from, for example without limitation, blood, CSF, sputum, ascites, aspirates, synovial tissue or biopsies of any tissue or tumor, bone marrow, or lymphoid tissue.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events that is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

METHODS OF THE INVENTION

Methods are provided for treating or reducing undesirable effects of dysregulated protein tyrosine phosphorylation in physiological conditions that include leukocyte trafficking; treatment of thalassemias, and cancer, including without limitation glioblastoma. In the methods of the invention a targeted cell population is contacted with an effective dose of a PTPRG activating agent as defined herein, which agent may comprise one or more of a wedge domain, an ICD, an IPD, and a soluble external domain (PTPx); any of which agents may be conjugated to a permeant domain. Such methods include administering to a subject in need of treatment a therapeutically effective amount or an effective dose of the agents of the invention, including without limitation combinations of the agent with a chemotherapeutic drug, radiation therapy, or an erythropoietin stimulating agent (ESA).

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

A PTPRG activator of the invention prevents triggering of integrin mediated adhesion, e.g. LFA-1 mediated adhesion, and is useful in the inhibition of undesirable immune responses by preventing the accumulation of effector cells at the site of inflammation. Such effector cells may include monocytes and other antigen presenting cells, PMN, etc. For example, the methods can prevent intra-islet infiltration by effector cells to inhibit development of insulin-dependent diabetes mellitus; blocking infiltration of effector cells into the central nervous system to treat multiple sclerosis and other demyelinating diseases; blocking the accumulation of effector cells in the synovial joints of patients suffering from rheumatoid arthritis; accumulation of effector cells to influence immune responsiveness, and the like.

Further, JAK2, demonstrated herein to be a direct target of PTPRG, has been identified as a target in a broad range of indications including RA, psoriasis, myelofibrosis, autoimmune disorders, solid tumors, hematological cancers, myeloproliferative disorders, pancreatic cancer, kidney transplant rejection, acute myelogenous leukemia, advanced myeloid malignancies, ulcerative colitis, dry eye disease, alopecia universalis, polycythemia vera, hair loss, and Crohn's disease. Conditions in which inhibition of JAK2 is desirable can be treated by administering a PTPRG activator of the invention.

The effect of a treatment can be monitored by determining the localization of different leukocyte subsets. Leukocyte subsets, e.g. T cells including Th1, Th2, Th3, regulatory T cells and cytotoxic T cells; polymorphonuclear cells (PMN); monocytes and macrophages; dendritic cells; B cells; and the like, are characterized according to the cell surface expression of certain known antigens. Verification of the identity of the cells of interest may be performed by any convenient method, including antibody staining and analysis by fluorescence detection, ELISA, etc., reverse transcriptase PCR, transcriptional amplification and hybridization to nucleic acid microarrays, etc. The effect of treatment can also be monitored by determining the adhesiveness of leukocytes, for example by assessing the affinity state of integrins, for example LFA-1, and/or the adhesive capability of the leukocytes using adhesion, ligand binding or similar assays.

Conditions of inflammation-associated or allergic reaction patterns of the skin include atopic dermatitis or infantile eczema; contact dermatitis, psoriasis, lichen planus; hypersensitivity or destructive responses to infectious agents, etc. Such diseases benefit from the administration of PTPRG activators. The treatment decreases the number of effector immune cells at the sites of inflammation.

Rheumatoid arthritis (RA) is a chronic autoimmune inflammatory synovitis affecting 0.8% of the world population. Current therapy for RA utilizes therapeutic agents that non-specifically suppress or modulate immune function. Such therapeutics, including the recently developed TNFα antagonists, are not fundamentally curative, and disease activity rapidly returns following discontinuation of therapy. The ability of the compounds of this invention to treat arthritis can be demonstrated in a murine collagen-induced arthritis model according to the method of Kakimoto, et al., Cell Immunol 142: 326-337, 1992, in a rat collagen-induced arthritis model according to the method of Knoerzer, et al., Toxicol Pathol 25:13-19, 1997, in a rat adjuvant arthritis model according to the method of Halloran, et al., Arthitis Rheum 39: 810-819, 1996, in a rat streptococcal cell wall-induced arthritis model according to the method of Schimmer, et al., J. Immunol 160: 1466-1477, 1998, or in a SCID-mouse human rheumatoid arthritis model according to the method of Oppenheimer-Marks et al., J Clin Invest 101: 1261-1272, 1998.

Degenerative joint diseases may be inflammatory, as with seronegative spondylarthropathies, e.g. ankylosing spondylitis and reactive arthritis; rheumatoid arthritis; gout; and systemic lupus erythematosus. There is significant immunological activity within the synovium during the course of inflammatory arthritis. While treatment during early stages is desirable, the adverse symptoms of the disease may be at least partially alleviated by treatment during later stages. The ability of the compounds of this invention to treat Lyme arthritis can be demonstrated according to the method of Gross et al., Science 281, 703-706, 1998.

A quantitative increase in myelin-autoreactive T cells with the capacity to secrete IFN-gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination.

Human IDDM is a cell-mediated autoimmune disorder leading to destruction of insulin-secreting beta cells and overt hyperglycemia. T lymphocytes invade the islets of Langerhans, and specifically destroy insulin-producing β-cells. The depletion of β cells results in an inability to regulate levels of glucose in the blood. An increase in the number of T lymphocytes in the pancreas, islet cell antibodies and blood glucose is indicative of the disease. After the onset of overt diabetes, patients with residual beta cell function, evidenced by the plasma persistence of insulin C-peptide, may benefit from the subject treatment, to prevent further loss of function. The ability of compounds of this invention to treat autoimmune diabetes can be demonstrated in an NOD mouse model according to the method of Hasagawa et al., Int Immunol 6:831-838, 1994, or in a murine streptozotocin-induced diabetes model according to the method of Herrold et al., Cell Immunol 157:489-500, 1994.

Other inflammatory conditions of interest include inflammatory bowel disease, lung disease, etc. The ability of compounds of this invention to treat inflammatory lung injury can be demonstrated in a murine oxygen-induced lung injury model according to the method of Wegner et al., Lung 170:267-279, 1992, in a murine immune complex-induced lung injury model according to the method of Mulligan et al., J Immunol 154:1350-1363, 1995, or in a murine acid-induced lung injury model according to the method of Nagase et al., Am J Respir Crit Care Med 154:504-510, 1996. The ability of compounds of this invention to treat inflammatory bowel disease can be demonstrated in a rabbit chemical-induced colitis model according to the method of Bennet et al., J Pharmacol Exp Ther 280:988-1000, 1997.

Allergy, or atopy is an increased tendency to IgE-based sensitivity resulting in production of specific IgE antibody to an immunogen, particularly to common environmental allergens such as insect venom, house dust mite, pollens, molds or animal danders. Allergic responses are antigen specific. The immune response to the antigen is further characterized by the over-production of Th2-type cytokines, e.g. IL-4, IL-5 and IL-10, by the responding T cells. The sensitization occurs in genetically predisposed people after exposure to low concentrations of allergen; cigarette smoke and viral infections may assist in the sensitization process.

Included in the group of patients suffering from atopy are those with asthma associated allergies. About 40% of the population is atopic, and about half of this group develop clinical disease ranging from trivial rhinitis to life-threatening asthma. After sensitization, continuing exposure to allergens leads to a significant increase in the prevalence of asthma. Ninety percent of children and 80% of adults with asthma are atopic. Once sensitization has occurred, re-exposure to allergen is a risk factor for exacerbations of asthma. Effective management of allergic asthma includes pharmacological therapy and allergen avoidance. The specific physiological effects of asthma associated allergies include airway inflammation, eosinophilia and mucus production, and antigen-specific IgE and IL-4 production. Modulation of Th1 and Th2 subsets, as well as antigen presenting cells, is useful in the treatment of allergic responses. The ability of compounds of this invention to treat asthma can be demonstrated in a murine allergic asthma model according to the method of Wegner et al., Science 247:456-459, 1990, or in a murine non-allergic asthma model according to the method of Bloemen et al., Am J Respir Crit Care Med 153:521-529, 1996.

The ability of compounds of this invention to treat graft rejection can be demonstrated in a murine cardiac allograft rejection model according to the method of Isobe et al., Science 255: 1125-1127, 1992, in a murine thyroid gland kidney capsule model according to the method of Talento et al., Transplantation 55: 418-422, 1993, in a cynomolgus monkey renal allograft model according to the method of Cosimi et al., J Immunol 144: 4604-4612, 1990, in a rat nerve allograft model according to the method of Nakao et al., Muscle Nerve 18:93-102, 1995, in a murine skin allograft model according to the method of Gorczynski and Wojcik, J Immunol 152: 2011-2019, 1994, in a murine corneal allograft model according to the method of He et al., Opthalmol Vis Sci 35:3218-3225, 1994, or in a xenogeneic pancreatic islet cell transplantation model according to the method of Zeng et al., Transplantation 58:681-689, 1994.

In one embodiment of this invention, modulation of neutrophil activation, interaction with the vasculature, adhesion, diapedesis, and function within the vasculature or in tissues using PTPRG ICD or related is done to prevent or treat conditions involving recruitment and function of neutrophils. In this embodiment, conditions that can be prevented or treated include but are not limited to neutrophil-associated pulmonary diseases, including chronic obstructive pulmonary disease, acute lung injury, chronic bronchitis, pulmonary emphysema, alpha-1 anti-trypsin deficiency, cystic fibrosis, idiopathic pulmonary fibrosis, pneumonia, emphysemia, and adult respiratory distress syndrome, and also multiple sclerosis and other autoimmune disease, sepsis, myocardial infarction, stroke, ischemia-reperfusion injury, bacterial meningitis, acute pancreatitis, multiple organ failure, acute cellulitis, asthma, osteomyelitis, Crohn's disease, ulcerative cholitis, cystic fibrosis, rheumatoid arthritis, uveitis, periodontitis, psoriasis, severe burns, skin ulceration, pneumonia, trauma, severe early graft dysfunction, complications of hemodialysis, restenosis, acute dermatitis, glomerulonephritis, cerebral trauma, spinal cord injury, neuropathic pain, cerebral infarction, Alzheimer's disease, epilepsy, status epilepticus, viral encephalitis, influenza-associated encephalopathy, diabetic vascular complication, organ dysfunction after surgical operation, myocarditis, endocarditis and heart failure.

In some embodiments an effective dose of one of the PTP activating agents of the invention will be used to prevent or treat neurological diseases where neutrophil blockade is beneficial, for example in Alzheimer's disease (for example see US Patent Application WO2015051152A1 herein specifically incorporated by reference and Zenaro E et al 2015 Nature Medicine 21, 880-886), epilepsy (for example see U.S. Pat. No. 8,383,116 B2 and U.S. Pat. No. 7,682,613 B2 herein specifically incorporated by reference, and Fabene P F et al 2008 Nature Medicine 14(12):1377-1383), and meningitis (Kim J V et al 2009 Nature 457(7226):191-195). In some embodiments and effective dose of a PTP activating agent of the invention will be used to treat pulmonary fibrosis; cardiomyocyte death induced by myocardial infarction and reperfusion injury; prevention of ventilation induced diaphragm mechanical dysfunction; prevention of pulmonary ischemic-reperfusion damages, ischemic-reperfusion induced lung injury.

It is shown herein that JAK2 is a direct target for PTPRG. The pharmaceutical compositions described herein are useful in treatment or prevention of diseases in which JAK2 is dysregulated, including but not limited to Blackfan-Diamond anemia (Jelinek J et al. Pediatr Hematol Oncol 29: 207, 2007), myelodysplastic syndromes Quintas-Cardama A et al. Leuk res 37: 465, 2013), congenital diserythropoietic anemia type II (Russo R et al. Am J Hematol 89: E169, 2014; Gambale A expert Rev Hematol Dec. 12, 2015; Unal S et al. Pediatr TRanspl 18: E130, 2014; Iolascon A et al. Blood 122: 2162, 2013; Iolascon A et al haematlogica 97: 1786, 2012), beta-thalassemia, and polycythemia (McMullin M F et al. Br. J. Hematol doi 10.1111/bjh.13812 oct 22, 2015; Okabe M et al. Leuk Red November 10. Poo: S0145-2126 (15)30540, 2015; Stein B L et al. J Clin Oncol November 20; 33(33)3953-60, 2015; Falchi L et al Clin Lymphoma Myeloma Leuk June 15 Suppl S27-33, 2015).

Erythropoietin is the first-line therapy for anemia of chronic kidney disease, cancer chemotherapy, AIDS, and lower-risk myelodysplastic syndrome; however, it is costly, frequently elevates hypertension, and may affect cancer progression. The pharmaceutical compositions described herein can be used alone or in combination with EPO or other therapeutics for anemia.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g. intravascular (intravenous, intraarterial, intracapillary) administration, injection into the cerebrospinal fluid, intracavity or direct injection in the brain. Intrathecal administration may be carried out through the use of an Ommaya reservoir, in accordance with known techniques. (F. Balis et al., Am J. Pediatr. Hematol. Oncol. 11, 74, 76 (1989).

Where the therapeutic agents are locally administered in the brain, one method for administration of the therapeutic compositions of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass. Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the therapeutic composition to the brain and/or tumor mass. Such devices are described in U.S. Pat. No. 5,720,720, incorporated fully herein by reference.

The effective amount of a therapeutic composition to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing $LD_{50}$ animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g. some agents may be taken for extended periods of time on a daily or semi-daily basis, while more selective agents may be administered for more defined time courses, e.g. one, two three or more days, one or more weeks, one or more months, etc., taken daily, semi-daily, semi-weekly, weekly, etc.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

Screening Methods

The methods of the invention include screening compounds that mimic or increase phosphatase activity, e.g. by contacting a cell that expresses the PTP or PTP targets of interest, and determining the PTP activity. Such embodiments may include, for example, a step of determining activity in a biological setting, e.g. LFA-1 triggering in monocytes. In some embodiments, an assay is performed where the ICD, IPD, PTPx or wedge polypeptides are used as a control to determine whether a candidate compound activates phosphatase activity. In these embodiments the ICD, IPD, PTPx or wedge activating polypeptides are used to establish a target signature phosphoproteome that the screening compounds should mimic in the target cells. In some embodiments the structure of the ICD or wedge domain is utilized as a starting point for rational drug design. Drug screening identifies agents that mimic, agonize or antagonize wedge or ICD activity. A wide variety of assays may be used for this purpose, including labeled in vitro protein-protein binding assays, electrophoretic mobility shift assays, immunoassays for protein binding, and the like.

Knowledge of the 3-dimensional structure, derived from the provided wedge or ICD domains, leads to the rational design of small drugs that specifically mimic their activity.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of assay conditions, for example in conjunction with assay conditions where the agent is not present, conditions where a known PTP activator are present, conditions in which a known activity is expected, e.g. LFA-1 triggering, and the like. The change in parameter readout in response to the agent is measured, desirably normalized, and the resulting data may then be evaluated by comparison to reference data.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The compounds having the desired pharmacological activity may be administered in a physiologically acceptable carrier to a host for treatment of inflammation related disorders, etc. The agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

In other screening assays, a PTP activator of the invention is brought into contact with a cell for the purpose of determining the phosphor-proteome response. The cell may be optionally contacted with an additional agent of the classes described above for the purpose of determining the effect of that agent.

The changes in phosphorylation of proteins in the cell for any of the above screening assays can be determined by various methods known in the art.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling specific changes in phosphorylation on proteins of interest. Immunofluorescent moieties can be directed to bind not only to specific proteins but also specific conformations, cleavage products, or site modifications like phosphorylation.

The use of high affinity antibody binding and/or structural linkage during labeling provides dramatically reduced non-specific backgrounds, leading to clean signals that are easily detected. Such extremely high levels of specificity enable the simultaneous use of several different fluorescent labels, where each preferably emits at a unique color. Fluorescence technologies have matured to the point where an abundance of useful dyes are now commercially available. These are available from many sources, including Sigma Chemical Company (St. Louis Mo.) and Molecular Probes (Handbook of Fluorescent Probes and Research Chemicals, Seventh Edition, Molecular Probes, Eugene Oreg.). Other fluorescent sensors have been designed to report on biological activities or environmental changes, e.g. pH, calcium concentration, electrical potential, proximity to other probes, etc. Methods of interest include calcium flux, nucleotide incorporation, quantitative PAGE (proteomics), etc.

Depending upon the label chosen, parameters may be measured using other than fluorescent labels, using such assay techniques as metal labeling for mass cytometry, radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting.

Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected phosphorylation changes, or the average fluorescence intensity, the median fluorescence intensity, the variance in fluorescence intensity, or some relationship among these.

Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. Plug-flow flow cytometry that has the potential to automate the delivery of small samples from unpressurized sources at rates compatible with many screening and assay applications, may allow higher throughput, compatible with high throughput screening, Edwards et al. (1999) Cytometry 37:156-9.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989, 833 issued Nov. 23, 1999.

A phosphor-proteome signature pattern may be generated from a biological sample using any convenient protocol, for example as described below. The readout may be a mean, average, median or the variance or other statistically or mathematically-derived value associated with the measurement. A signature pattern may be evaluated on a number of points: to determine if there is a statistically significant change at any point in the data matrix; whether the change is an increase or decrease in the specific phosphorylation; whether the change is specific for one or more physiological states or factors, and the like.

Following obtainment of the signature pattern from the sample being assayed, the signature pattern is compared with a reference or control profile to make an evaluation regarding targets of the phosphatase, activity of a candidate factor, and the like. Typically a comparison is made with a sample or set of samples from a control profile.

In order to identify profiles that are indicative of responsiveness, a statistical test will provide a confidence level for a change in the expression, titers or concentration of markers between the test and control profiles to be considered significant, where the control profile may be for responsiveness or non-responsiveness. The raw data may be initially analyzed by measuring the values for each marker, usually in duplicate, triplicate, quadruplicate or in 5-10 replicate features per marker.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pairwise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. One approach is to consider a patient autoimmune disease dataset as a "learning sample" in a problem of "supervised learning". CART is a standard in applications to medicine (Singer (1999) Recursive Partitioning in the Health Sciences, Springer), which may be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that may be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

In a second analytical approach, variables chosen in the cross-sectional analysis are separately employed as predictors. Given the specific outcome, the random lengths of time each patient will be observed, and selection of proteomic and other features, a parametric approach to analyzing responsiveness may be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models may be used, especially since reductions of numbers of covariates to manageable size with the lasso will significantly simplify the analysis, allowing the possibility of an entirely nonparametric approach to survival.

These statistical tools are applicable to all manner of phosphorylation specificity data. A set of data that can be easily determined, and that is highly informative regarding detection of individuals with clinically significant responsiveness to therapy is provided.

Also provided are databases of signature patterns for responsiveness of target proteins to phosphatase activation. Such databases will typically comprise signature patterns of cells having responsive phenotypes, non-responsive phenotypes, etc., where such profiles are as described above.

The analysis and database storage may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information.

The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof may be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

Also provided are kits or articles of manufacture comprising the compositions described herein in suitable packaging. Suitable packaging for compositions (such as parenteral compositions) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples will be described to illustrate parts of the invention.

The invention may be better understood with reference to the accompanying examples.

Example 1

Identification and Functional Characterization of the PTPRG Wedge Domain

We show in this example that the PTPRG wedge domain (WD) can activate PTPRG tyrosine phosphatase activity. We hypothesized that interference by steric hindrance with the wedge domain (WD) could lead to PTPRG monomerization and/or catalytic domain separation, thus freeing the intrinsic tyrosine phosphatase activity by removing intermolecular D2 versus D1 domain inhibition. We performed bioinformatics analysis based on comparison with previously characterized WDs in protein tyrosine phosphatase, receptor type A (PTPRA; Bilwes, A M, et al., 1996, Nature 382: 555-559.), PTP Receptor type C (PTPRC or CD45; Majeti, R, et al., 1998. Science 279: 88-91), protein tyrosine phosphatase, receptor type, F (LAR; Xie Y et al., 2006, J Biol Chem 281: 16482-16492) and protein tyrosine phosphatase, receptor type M (PTPRM Xie Y et al., 2006, J Biol Chem 281: 16482-16492), performed with BLASTp and PTP-dedicated online resources, identified the PTPRG wedge domain as a juxtamembrane 26 aa sequence encompassing aa 831 to 856 (SEQ ID 1), with the last 11 aa (SEQ ID 2) belonging to the D1 phosphatase active domain.

Our analysis demonstrates that the PTPRG wedge domain displays a helix-turn-helix structure and a high solvent accessibility, as evidenced by residue analysis and hydropathy calculation and by Accessible Surface Area calculation with the online algorithm ASA View. Our analysis indicates the capability of this region to support protein interactions The WEDGE domain (SEQ ID NO:1) and crystallographic rendering of the intracellular region of PTPRG shows that, in keeping with the analysis of Accessible Surface Area, the identified WEDGE domain is exposed on the molecule surface in a manner allowing for protein-protein interactions. The crystallographic rendering shows a helix-turn-helix structural arrangement, often reported in protein-protein interactions.

A fusion P1-WD Trojan peptide (SEQ ID 3) was then generated using the Penetratin sequence (SEQ ID 4) to facilitate delivery of the WD into the cell (Dupont E et al, 2015 Methods Mol Biol. 1324:29-37; Madani F, 2011, J Biophys 2011: 414729).

Briefly, The P1-WD peptide sequence is as follows: SEQ ID 3: RQIKIWFQNRRMKWKK GKQFVKHIGELYSNNQHGFSEDFEEVQ encompassed the complete P1 (Penetratin) sequence (16 aa; RQIKIWFQNRRMKWKK; SEQ ID 4), an inserted glycine (G) to allow flexibility of the fusion peptide and the computationally identified PTPRG wedge domain sequence encompassing aa 831 to 856 of human PTPRG (SEQ ID 1, 26 aa; KQFVKHIGELYSNNQHGFSEDFEEVQ)

were synthesized. Underlined is the aa sequence shared with the D1 phosphatase active domain.

SEQ ID NO: 1: wedge domain = aa 831-856 =

KQFVKHIGELYSNNQHGFSEDFEEVQ

SEQ ID NO: 2: last 11 aa part of D1 =

HGFSEDFEEVQ monocytes but not neutrophils and reveals a double PTPRG band in the monocyte lysates, likely due to differential PTPRG post-translational modification, such as glycosylation.

The phosphatase activity in membrane fractions isolated from human monocytes and PMNs was assessed. Briefly, freshly isolated monocytes and PMNs were suspended in 100 mM PIPES, 12.5 mM EGTA, 300 mM KCl, 30 mM NaCl, 35 mM $MgCl_2$, pH 7.3 (relaxation buffer) in presence of proteases inhibitors. Cells were then sonicated twice (6 sec, 15% W) and centrifuged at 2000 rpm for 10 minutes. The supernatants were collected and centrifuged at 28000 rpm for 60 minutes. After centrifugation, the supernatants were discarded, and the membrane pellets were dissolved in 20 mM tris pH 7.4. Equal amount of membrane fractions were added to pNPP buffer containing 20 mM tris, 10 mM DTT and 2 mM pNPP. Following, DMSO and peptides were added. After 30 minutes of incubation, levels of de-phosphorylation, in presence or absence of orthovanadate, were measured at 405 nm by a plate reader. Values are absorbance at 405 nn shown as percent fold increase over the blank; mean values of three experiments are shown. *$p<0.001$ vs vehicle (DMSO).

TABLE 1

P1-WD Peptide Triggers a Specific, Dose-dependent Increase in Tyrosine Phosphatase Activity in Monocytes But Not PMNs

|  |  | DMSO | P1-WD (micromolar) | | | P1 | P1-WD scrambled |
|---|---|---|---|---|---|---|---|
|  |  |  | 50 | 100 | 200 |  |  |
| Monocytes | Mean | 7.25 | 34.62* | 86.70* | 109.00* | 16.00 | 21.67 |
|  | St. Dev | 1.63 | 2.74 | 4.61 | 12.52 | 4.58 | 7.64 |
| PMN | Mean | 0.75 | 5.15 | 8.54 | 12.89 | 5.08 | 6.67 |
|  | Std. Dev | 0.62 | 3.30 | 0.64 | 2.72 | 1.65 | 1.51 |

-continued

SEQ ID NO: 3: P1-WD =

RQIKIWFQNRRMKWKKGKQFVKHIGELYSNNQHGFSEDFEEVQ

SEQ ID NO: 4: P1 = Penetratin 1 =

RQIKIWFQNRRMKWKK

SEQ ID NO: 5: TAT-ICD

SEQ ID NO: 6: ICD, aa 797-1455

SEQ ID NO: 7: IPD, aa 846-1445

SEQ ID NO: 8 PTPx, aa 20-736

We first tested the biochemical activity of the fusion peptide by performing in vitro assays of phosphatase activity on purified membranes isolated from human primary monocytes compared to membranes isolated from human primary polymorphonuclear cells (PMNs). Human primary monocytes and polymorphonuclear (PMNs) cells were isolated from whole blood of healthy donors. Purity of monocyte preparation was evaluated by flow cytometry after staining with fluorescein isothiocyanate (FITC)-conjugated anti-CD14 antibody and was more than 95%. Isolated cells were kept at 37° C. in standard adhesion buffer (PBS, 1 mM $CaCl_2$, 1 mM $MgCl_2$, 10% FBS, pH 7.2) and used within 1 h. Western Blot analysis confirms presence of PTPRG in The P1-WD peptide elicited in a dose-dependent manner a consistent phosphatase activity in membrane isolated from monocytes (Table 1). In contrast, control P1 and P1-WD scrambled peptides were minimally effective. Orthovanadate treatment completely prevented phosphatase activity, demonstrating the triggering of a tyrosine phosphatase activity. Importantly, the P1-WD peptide did not elicit a consistent phosphatase activity in membrane isolated from PMNs (Table 1) showing that the wedge domain from PTPRG does not activate the highly related PTPRC in PMNs, demonstrating its specificity.

Example 2

Activation of PTPRG Inhibits LFA-1 Affinity Triggering and Mediated Adhesion Triggered by Chemoattractants in Human Primary Monocytes In this example we demonstrate that activated PTPRG acts as a negative regulator of signaling mechanisms controlling integrin activation and mediated adhesion in human primary monocytes. We investigated the functional effect of PTPRG activation on integrin activation and mediated adhesion by chemoattractants in human primary monocytes and PMNs in a static and flow adhesion assays. Briefly, human primary monocytes or polymorphonuclear cells were suspended at $5 \times 10^6$/ml in standard adhesion buffer. Adhesion assays were performed on 18-well glass slides coated with 1 mg/ml human fibrinogen or with 1 µg/ml human ICAM-1 in PBS; 20 µl of cell suspension were added to the coated wells and stimulated for 1 min at 37° C. with 5 µl of fMLP, 0.05 µM final concentration. After rapid washing, adherent cells were fixed in ice-cold 1.5% glutaraldehyde in PBS, and still images of adherent cells in 0.2 mm² fields were acquired al 20× phase contrast magnification, NA 0.40, with a charge-coupled device camera (ICD-42B; Ikegami) connected to an inverted microscope (IX50; Olympus). Image acquisition and computer-assisted enumeration of adherent cells were performed with ImageJ (National Institute of Health).

TABLE 2

P1-WD Peptide Inhibits LFA-1-mediated Adhesion Triggered by Chemoattractants in Human Primary Monocytes

|  |  | Fibrinogen | | ICAM-1 | |
| --- | --- | --- | --- | --- | --- |
|  |  | mean | SD | mean | SD |
| CTRL |  | 100 | 14 | 100 | 14 |
| P1-WD (micromolar) | 10 | 41 | 15 | 78 | 17 |
|  | 25 | 18 | 15 | 40 | 9 |
|  | 50 | 16 | 10 | 19 | 8 |
| P1 |  | 94 | 14 | 102 | 19 |
| P1-WD_scrambled |  | 92 | 10 | 93 | 18 |

Treatment of monocytes with the P1-WD peptide prevented in dose-dependent manner fMLP-triggered static adhesion to fibrinogen as well as to ICAM-1 (Table 2) thus suggesting blockade of Mac1 (CD11b/CD18), P150/95 (CD11c/CD18) and LFA-1 (CD11a/CD18) β2 integrins activation.

Flow-adhesion assays were also performed to test the ability of the P1-WD peptide to inhibit adhesion of human monocytes under flow conditions. Briefly, Human primary monocytes were suspended at 1×10⁶/ml in standard adhesion. Cell behavior in underflow conditions was analyzed with the BioFlux 200 system (Fluxion Biosciences). 48-well plate microfluidics were first co-coated overnight at room temperature with 2.5 µg/ml human E-selectin and 5 µg/ml human ICAM-1 in PBS. Immediately before use, microfluidic channels were washed with PBS and then coated with 10 nM fMLP in PBS for 3 h at room temperature. After extensive washing of microfluidics with adhesion buffer, cells were fluxed at 2 dyne/cm² wall shear stress and the behavior of interacting cells was digitally recorded with a fast CCD videocamera (25 frames/s). Single areas of 0.2 mm² were recorded for at least 120 s. Interactions of 40 ms or longer were considered significant and scored. Cells that remained firmly adherent for at least 1 s were considered fully arrested. Cells arrested for at least 1 s and then detached, or for 10 s and then remained adherent, were scored separately and plotted as independent groups. Interacting cells behaviors were automatically quantified with BeQuanti.

TABLE 3

P1-WD Peptide Inhibits LFA-1-triggered Adhesion by Chemoattractants in Human Monocytes in Flow Assays

|  | rolling | | arrest 1 sec | | arrest 10 sec | |
| --- | --- | --- | --- | --- | --- | --- |
|  | mean | SD | mean | SD | mean | SD |
| CTRL | 50 | 8 | 24 | 8 | 26 | 8 |
| P1-WD | 80 | 9 | 9 | 9 | 11 | 5 |
| P1 | 38 | 10 | 32 | 15 | 30 | 6 |
| P1-WD_scrambled | 44 | 12 | 26 | 14 | 30 | 7 |

The P1-WD peptide also prevented monocyte arrest on ICAM-1 in underflow adhesion assays (Table 3), a condition dependent of rapid LFA-1 triggering to high affinity state (10, 21, 22). Indeed, treatment with P1-WD led to a consistent reduction of arrested cells accompanied by a corresponding increase of rolling cells, as expected (Table 3).

The ability of P1-WD to inhibit triggering of LFA-1 to a high-affinity state was assessed using a specific reporter monoclonal antibody 327C, which detects the fully extended LFA-1 conformational epitope corresponding to heterodimer high affinity state. Briefly, freshly isolated human monocytes were suspended in standard adhesion buffer at 2×10⁶/ml were stimulated under stirring at 37° C. for 1 min with 50 nM fMLP in the presence of 10 □g/ml 327C mAb. After rapid washing, the cells were stained with FITC-conjugated secondary antibody and analyzed by cytofluorimetric quantification (Table 4). Data are mean fluorescence intensity measured by flow cytometry relative to the fMLP-stimulated control (CTRL) cells.

TABLE 4

P1-WD inhibits Triggering of LFA-1 to a High Affinity State

|  | mean | SD |
| --- | --- | --- |
| CTRL | 100 | 4 |
| P1-WD | 22 | 6 |
| P1 | 91 | 8 |
| P1-WD_scrambled | 89 | 7 |

Pretreatment with P1-WD led to a very consistent inhibition of LFA-1 triggering to high affinity state by fMLP (Table 4). In the assays, treatment with the P1 or P1-WD-scrambled peptides was completely ineffective, thus demonstrating the specificity and excluding toxic effects of the P1-WD peptide. Importantly, PMNs were completely unaffected by P1-WD treatment.

Example 3

Activation of PTPRG Using a the PTPRG Intracellular Phosphatase Domain (ICD) Fused to an Alternative Cell Penetrating System Based on TAT Inhibits LFA-1 Affinity Triggering and Mediated Adhesion by Chemoattractant Triggered Human Monocytes In this example we demonstrate that PTPRG ICD retains PTPRG catalytic activity and that when delivered to human monocytes using a cell penetrating technology it is a negative regulator of signaling mechanisms triggered by chemoattractants and can block integrin activation and adhesion in human monocytes. We further demonstrate a method to investigate the functional effects of increasing PTPRG activity in primary cells.

A fusion recombinant protein was generated (TAT-ICD; SEQ ID 5) encompassing the PTPRG intracellular domain (ICD; aa 797-1445; SEQ ID 6) fused to the Trojan 13 aa TAT sequence SEQ ID NO:5, residues 1-13, GRKKRRQRRRPPQ, used as a prototype cell penetrating peptide able to transport biologically active proteins into the cell (Madani F, 2011, J Biophys 2011: 414729). The ICD is includes the catalytic, intracellular phosphatase domain (IPD; SEQ ID 7, aa 846-1445).

We show that the TAT-ICD fusion protein retained tyrosine phosphatase activity, as verified in in vitro phosphatase assays (Table 5). Briefly, freshly isolated monocytes and PMNs were suspended in 100 mM PIPES, 12.5 mM EGTA, 300 mM KCl, 30 mM NaCl, 35 mM MgCl2, pH 7.3 (relaxation buffer) in presence of proteases inhibitors. Cells were then sonicated twice (6 sec, 15% \N) and centrifuged at 2000 rpm for 10 minutes. The supernatants were collected and centrifuged at 28000 rpm for 60 minutes and then the membrane pellets were dissolved in 20 mM tris pH 7.4. Equal amount of membrane fractions were added to pNPP buffer containing 20 mM tris, 10 mM DTT and 2 mM pNPP. Following, DMSO and 50 µM TAT control peptide or 50 µM TAT-ICD, in presence or absence of 200 µM Na3VO4 were added. After 30 minutes of incubation, levels of de-phosphorylation, in presence or absence of orthovanadate, were measured at 405 nm by a plate reader (Table 5). Shown is % fold increase over the pNPP buffer alone; mean values of 7 experiments in triplicate.

TABLE 5

TAT-ICD Fusion Protein Confirmed to have Tyrosine Phosphatase Activity in In Vitro Phosphatase Assay

|  | TAT peptide | TAT-ICD | TAT-ICD + $Na_3VO_4$ |
|---|---|---|---|
| Mean | 191.7 | 4661.0 | 191.7 |
| Std. Deviation | 58.9 | 762.1 | 58.9 |

We then investigated the functional effect of TAT-ICD on integrin activation and mediated adhesion by chemoattractants. Static adhesion assays were performed as described in Example 2. Monocyte treatment with TAT-ICD strongly prevented, in dose-dependent manner, static adhesion to fibrinogen as well as to ICAM-1 (Table 6). Data are mean number of adherent cells in 5 experiments in triplicate.

TABLE 6

TAT-ICD Fusion Protein Inhibits Adhesion Triggered by Chemoattractants in Human Primary Monocytes

|  | Fibrinogen | | ICAM-1 | |
|---|---|---|---|---|
|  | mean | SD | mean | SD |
| CTRL | 100 | 0 | 100 | 0 |
| TAT-ICD (µM) | | | | |
| 0.01 | 45.4 | 5 | 48 | 8 |
| 0.05 | 35.5 | 10 | 36 | 12 |
| 0.10 | 27.9 | 10 | 30 | 12 |
| 0.50 | 20.1 | 6 | 14 | 4 |
| 1 | 14.0 | 8 | 10 | 10 |
| TAT (µM) | | | | |
| 0.5 | 100 | 12 | 100 | 12 |
| 1 | 98 | 9 | 110 | 9 |

TAT-ICD also prevented monocyte arrest on ICAM-1 in underflow adhesion assays (Table 7), performed as described in Example 2 for Table 3. Briefly, human monocytes were treated with buffer (CTRL), 50 µM TAT peptides, or 0.5 µM TAT-ICD for 1 hour at 37° C. Data are percentages of rolling and arrested cells for the indicated times over total interacting cells; mean values of 4 experiments.

TABLE 7

TAT-ICD Fusion Protein Inhibits Adhesion Triggered by Chemoattractants in Human Primary Monocytes in Flow Assays

|  | rolling | | arrest 1 sec | | arrest 10 sec | |
|---|---|---|---|---|---|---|
|  | mean | SD | mean | SD | mean | SD |
| CTRL | 12 | 5 | 22 | 4 | 66 | 7 |
| TAT | 14 | 6 | 25 | 4 | 61 | 11 |
| TAT-ICD | 79 | 10 | 10 | 3 | 11 | 9 |

The ability of TAT-ICD to trigger the high affinity state of LFA-1 was tested as described in Example 2, Table 4 and the results are in Table 8. Human monocytes were treated with buffer (CTRL), 50 µM TAT peptides, or 0.5 µM TAT-ICD for 1 hour at 37° C. and stimulated with 50 nM fMLP for 60 seconds. Data are the percentages of fold-increase over control; mean values of 6 experiments

TABLE 8

TAT-ICD Fusion Protein Inhibits Triggering of LFA-1 to a High Affinity State

|  | CTRL | TAT | TAT-ICD |
|---|---|---|---|
| Mean | 100 | 85.3 | 24.3 |
| St. Dev. | 0 | 13.2 | 7.5 |

These data (Tables 5-8) show that PTPRG intracellular phosphatase domains (ICD), including both D1 and D2 domains fused, at the N-terminus, to the cell penetrating peptide TAT sequence retains specific tyrosine phosphatase activity and inhibits LFA-1 affinity triggered adhesion mediated by chemoattractants in static and flow adhesion assays and inhibits triggering of LFA-1 to a high affinity state. In the assays, treatment with the TAT control peptide was completely ineffective.

Example 4

Network Reconstruction and Modular Decomposition of PTPRG-Influenced Protein Tyrosine Phospho-Network Reveals the Influence of PTPRG Activity on Chemoattractant Signaling To identify PTPRG targets in the context of fMLP signaling, we employed a high throughput antibody array technology using the P1-WD approach and fMLP-potentiated signaling networks, since this directly correlates with integrin triggering and mediated rapid adhesion. To analyze the phosphoproteome we used the comprehensive high throughput service developed by Kinexus, CA, USA. The Kinexus antibody microarray includes about 500 pan-specific and over 350 phosphosite-specific antibodies per chip, in duplicate spots. The analysis covers a variety of selected cell signaling proteins regulating cell proliferation, stress, apoptosis, adhesion, secretion, motility and other biological processes. Monocytes were treated with 50 µM P1 or P1-WD peptides for 60 min. at 37° C. and then stimulated with 50 nM fMLP for 3 min. Cells were immediately lysed according to Kinexus protocol and the samples were sent to Kinexus for microarray analysis. Data were normalized to control cells and statistically filtered by Kinexus to identify the most significant best hits. The analysis was, then, focused on phosphotyrosine-specific antibodies. Network inference analysis was performed within Cytoscape 3.1 bioinformatics environment by using previously established interatomic datasets compiled from public data-bases. The compiled protein-protein interatomic data-set was manually curated to remove self-loops and duplicate edges; different protein IDs were normalized to HGNC standard IDs. The set triggering in P1-WD-treated vs P1-control treated monocytes. For some proteins (For some proteins (EGFR, INSR, KDR, KIT, PDGFRA, PTK2, PXN, SRC and ZAP70) multiple phosphotyrosine residues are detected. From left to right, columns are HGNC protein symbols (in alphabetic order), phosphosites (p-Sites), changes of phosphorylation (induced by P1-WD) and the putative functional effect, inferred from literature data-mining. EGFR and PTK2 are highlighted in gray since the functional effect could not be unambiguously inferred. The functional effect of P1-WD in the far right column indicates either inhibition (IN) or activation (ACT).

TABLE 9

Target Proteins Affected by PTPRG Activation

| HGNC protein symbols | p-Site | % | p-Site | % | P-Site | % | P-Site | % | Functional effect of P1-WD |
|---|---|---|---|---|---|---|---|---|---|
| ABL1 | Y412 | −40 | | | | | | | IN |
| BLNK | Y84 | 19 | | | | | | | ACT |
| BMX | Y40 | −7 | | | | | | | IN |
| BTK | Y223 | −58 | | | | | | | IN |
| CDK2 | Y15 | 282 | | | | | | | IN |
| CTTN | Y470 | 21 | | | | | | | IN |
| DAB1 | Y198 | −34 | | | | | | | IN |
| DOK2 | Y142 | 9 | | | | | | | ACT |
| EGFR | Y1068 | −13 | Y1148 | −16 | Y1173 | 68 | | | IN/IN/ACT |
| ERBB2 | Y1248 | 34 | | | | | | | ACT |
| GRIN2B | Y1474 | 29 | | | | | | | ACT |
| INSR | Y999 | 58 | Y1189/Y1190 | 27 | | | | | ACT/ACT |
| ITGB1 | Y783 | −11 | | | | | | | IN |
| JAK2 | Y1007/Y1008 | −33 | | | | | | | IN |
| KDR | Y1054 | −37 | Y1054 + Y1059 | 22 | | | | | IN |
| KIT | Y703 | −60 | Y730 | −47 | | | | | IN |
| LIMK1 | Y507 | −10 | | | | | | | IN |
| MET | Y1003 | −47 | | | | | | | IN |
| PDGFRA | Y742 | 133 | Y754 | 86 | | | | | ACT |
| PDGFRB | Y716 | −36 | | | | | | | IN |
| PRKCD | Y313 | 189 | | | | | | | ACT |
| PTK2 | Y397 | 30 | Y577 | −60 | Y576 | 65 | Y861 | −11 | ACT/IN/ACT/IN |
| PXN | Y118 | 144 | Y31 | 19 | | | | | ACT/ACT |
| SHC1 | Y349 + Y350 | −10 | | | | | | | IN |
| SRC | Y419 | −6 | Y530 | 94 | | | | | IN/IN |
| STAT1 | Y701 | 38 | | | | | | | ACT |
| STAT2 | Y690 | 61 | | | | | | | ACT |
| STAT3 | Y705 | 182 | | | | | | | ACT |
| STAT5A | Y694 | 50 | | | | | | | ACT |
| VCL | Y821 | −20 | | | | | | | IN |
| ZAP70 | Y292 | −46 | Y315 + Y319 | 12 | | | | | ACT/ACT | of 31 identified proteins whose tyrosine phosphorylation status was affected by PTPRG activity was used as bioinformatics probe allowing sub-network reconstruction. Directed node centrality indexes were computed with the Cytoscape plug-in Centiscape 2.1 (Scardoni G, et al., 2009, Bioinformatics 25: 2857-2859). Network modular decomposition was executed with the Cytoscape plug-in MCODE (Bader G, et al., 2003, BMC Bioinformatics 4: 2). Literature data mining was performed by multiple data base interrogation, mainly based on Phosphosite, PhosphoELM, PhosphoNet and KEA.

Data analysis identified 31 molecules whose phosphorylation was modified in a statistically significant manner (Table 9). Values in % columns are percentage increase or decrease of protein tyrosine phosphorylation upon fMLP- PTPRG activation by the P1-WD peptide affected the tyrosine phosphorylation of several signaling molecules. Data analysis identified 31 molecules whose phosphorylation was modified in a statistically significant manner (Table 9). Interestingly, 16 proteins showed reduced tyrosine phosphorylation, possibly indicating a direct PTPRG targeting activity. In contrast, 15 proteins showed an increased tyrosine phosphorylation. This may suggest an indirect and more complex effect, possibly mediated by PTPRG-sensitive, concurrent, signaling mechanisms, thus indicating that PTPRG, beside a de-phosphorylating activity on direct targets, may also generate non-linear effects mediated by more complex signaling cascades. Literature data-mining suggests that the functional activity of a sub-group of 16 proteins including ABL1, BMX, BTK, CDK2, CTTN, DAB1, ITGB1, JAK2, KDR, KIT, LIMK1, MET, PDGFRB, SHC1, SRC and VCL is inhibited by PTPRG activation. Among these, inhibition of ABL1, BMX, BTK, DAB1, ITGB1, JAK2, KDR, KIT, LIMK1, MET, PDGFRB, SHC1, VCL correlates with tyrosine de-phosphorylation. In contrast, SRC inhibition correlates with hyper-phosphorylation of the inhibitory tyr 530 residue and with de-phosphorylation of the activatory tyr 419. Moreover, CDK2 and CTTN inhibition correlates with a hyper-phosphorylation of the inhibitory tyr 15 and tyr 470, respectively. In contrast, a sub-group of 14 proteins including BLNK, DOK2, ERBB2, GRIN2B, INSR, PDGFRA, PRKCD, PXN, STAT1, STAT2, STAT3, STAT5A and ZAP70 appears to be activated by PTPRG activity. Among these, activation of BLNK, DOK2, ERBB2, GRIN2B, INSR, PDGFRA, PRKCD, PXN, STAT1, STAT2, STAT3 and STAT5A correlates with tyrosine hyper-phosphorylation. Moreover, activation of ZAP70 correlated with de-phosphorylation of the inhibitory tyr 292.

The directed node centrality index values were calculated for every PTPRG target identified by the Kinexus analysis (Table 10). Node centrality indexes categorize proteins by topological relevance, thus predicting functional significance. Centralities are calculated by applying algorithms computing directed networks, thus keeping in consideration the direction of signaling flow. SRC displays the highest scores for 8 among 10 computed centrality indexes and is highlighted in yellow.

Network inference analysis shows that the 31 identified proteins generate a single network connected component, with no isolated nodes, suggesting that PTPRG may affect the function of an integrated signaling macro-module controlling many cellular functions. Graph topological analysis performed by applying mathematical algorithms computing network node centrality indexes, categorizing proteins by topological relevance (Scardoni G., et al., 2009. Bioinformatics 25: 2857-2859; Jeong H., et al., 2001. Nature 411: 41-42; Gu, Z. et al., 2012. BMC Syst Biol 6: 56; Scardoni, G. et al., 2014. PLoS One 9: e88938; Raman, K., et al., 2014. Syst Synth Biol 8: 73-81) predicting functional significance (De Franceschi, L., et al., 2012, PLoS One 7: e31015) shows that SRC appears by far the most connected and central signaling protein in the network, followed by KIT, PTK2, ITGB1, STAT1, EGFR, PDGFRB, ABL1 and BTK (Table 10), suggesting that, in the context of chemoattractants signaling, Src Family Kinases (SFKs) are possibly main functional targets of PTPRG activity. Network modular decomposition allowed isolating two modules, prevalently including activated (Table 11; Module A) or inhibited proteins (Table 11; Module B).

TABLE 10

Node Centrality Indexes of the PTPRG-influenced Protein Tyrosine Phospho-network

| Protein symbol | In-degree | Out-degree | Betweenness | Bridging | Centroid | Closeness | Eccentricity | EigenVector | Radiality | Stress |
|---|---|---|---|---|---|---|---|---|---|---|
| ABL1 | 3 | 6 | 27.8 | 1.90 | −26 | 14.5 | 0.25 | −2.81E−16 | 0.0074 | 90 |
| BLNK | 1 | 3 | 8.4 | 5.63 | −26 | 13.3 | 0.33 | −2.61E−15 | 0.0073 | 20 |
| BMX | 3 | 2 | 2.8 | 1.33 | −26 | 9.9 | 0.25 | 1.51E−15 | 0.0071 | 5 |
| BTK | 4 | 3 | 28.5 | 4.26 | −26 | 10.8 | 0.25 | 1.08E−15 | 0.0072 | 52 |
| CDK2 | 0 | 1 | 0.0 | 0.00 | −27 | 9.9 | 0.20 | 2.55755644 | 0.0071 | 0 |
| CTTN | 7 | 1 | 22.4 | 4.32 | −26 | 12.2 | 0.33 | −2.30E−15 | 0.0073 | 34 |
| DAB1 | 1 | 1 | 0.0 | 0.00 | −26 | 10.4 | 0.25 | 5.48E−16 | 0.0072 | 0 |
| DOK2 | 1 | 0 | 0.0 | 0.00 | 0 | 0.0 | 0.00 | −0.567252332 | 0.0067 | 0 |
| ERBB2 | 1 | 6 | 0.5 | 0.17 | −26 | 15.3 | 0.33 | 0.567252332 | 0.0074 | 1 |
| GRIN2B | 0 | 0 | 0.0 | 0.00 | 0 | 0.0 | 0.00 | −1.348974499 | 0.0067 | 0 |
| INSR | 1 | 3 | 1.0 | 0.67 | −26 | 11.8 | 0.25 | 5.34E−16 | 0.0072 | 3 |
| ITGB1 | 4 | 9 | 60.8 | 2.43 | −26 | 17.0 | 0.33 | −8.33E−17 | 0.0075 | 128 |
| JAK2 | 5 | 10 | 27.7 | 1.18 | −26 | 15.8 | 0.25 | −4.73E−15 | 0.0075 | 80 |
| KDR | 1 | 4 | 0.0 | 0.00 | −26 | 13.8 | 0.33 | 0.17180628 | 0.0073 | 0 |
| KIT | 4 | 6 | 94.6 | 12.65 | −26 | 15.0 | 0.33 | 9.99E−16 | 0.0074 | 184 |
| LIMK1 | 0 | 0 | 0.0 | 0.00 | 0 | 0.0 | 0.00 | 0.393303886 | 0.0067 | 0 |
| MET | 2 | 6 | 4.4 | 1.00 | −26 | 14.8 | 0.33 | 1.78E−16 | 0.0074 | 26 |
| PDGFRA | 1 | 6 | 0.0 | 0.00 | −26 | 15.2 | 0.33 | 0.17180628 | 0.0074 | 0 |
| PDGFRB | 3 | 9 | 39.4 | 3.15 | −26 | 16.8 | 0.33 | −3.23E−15 | 0.0075 | 81 |
| PRKCD | 2 | 4 | 26.0 | 8.03 | −26 | 14.2 | 0.33 | −0.17180628 | 0.0074 | 38 |
| PTK2 | 13 | 9 | 63.3 | 1.18 | −26 | 16.7 | 0.33 | 1.15E−15 | 0.0075 | 172 |
| PXN | 7 | 5 | 14.0 | 0.51 | −26 | 14.3 | 0.33 | 4.08E−16 | 0.0074 | 62 |
| SHC1 | 15 | 2 | 25.5 | 0.78 | −26 | 12.8 | 0.33 | −3.47E−16 | 0.0073 | 87 |
| SRC | 15 | 18 | 357.1 | 2.20 | −26 | 22.0 | 0.50 | −1.34E−15 | 0.0078 | 605 |
| STAT1 | 9 | 4 | 54.7 | 2.71 | −26 | 11.5 | 0.25 | 5.71E−16 | 0.0072 | 111 |
| STAT2 | 2 | 1 | 0.0 | 0.00 | −26 | 8.0 | 0.20 | −2.25E−15 | 0.0070 | 0 |
| STAT3 | 12 | 2 | 8.7 | 0.44 | −26 | 8.5 | 0.20 | 1.95E−15 | 0.0071 | 21 |
| STAT5A | 9 | 1 | 16.9 | 1.75 | −26 | 9.7 | 0.25 | −7.36E−16 | 0.0071 | 46 |
| VCL | 3 | 2 | 0.0 | 0.00 | −26 | 12.8 | 0.33 | −1.63E−15 | 0.0073 | 0 |
| ZAP70 | 0 | 0 | 0.0 | 0.00 | 0 | 0.0 | 0.00 | −1.017281585 | 0.0067 | 0 |

TABLE 11

Topological clusters of interacting nodes obtained by network modular decomposition

| Module A: 4.6 Clustering Score | | Module B: 5.5 Clustering Score | | |
|---|---|---|---|---|
| Inhibited | Activated | Inhibited | Activated | Not Affected |
| STAT-1 | SHC1 | ERBB2 | VCL | PTK2 |
| PDGFRA | PSGFRB | PXN | ITGB1 | EGFR |
| STAT5A | | BLNK | JAK2 | |
| | | | KIT | |
| | | | BTK | |
| | | | ABL1 | |
| | | | SRC | |
| | | | MET | |

Thus, the two modules may potentially represent a more specific and structured context of functional influence of PTPRG on chemoattractant signaling in human monocytes. Notably, the graph edge directionality also highlights the signaling flow in the modules, thus facilitating the inference of protein reciprocal functional influence.

This example demonstrates that modulating PTPRG activity using agents of this invention broadly influences the phosphoproteome, key regulatory proteins and, thus, the function of cells. We demonstrate that PTPRG activation modulates the chemoattractant-triggered signaling network and that the protein kinases SRC, KIT, ABL1, ZAP70, BTK, CDK2, JAK2, KDR, PDGFRA, PDGFRB, PRKCD and PTK2 appear direct or indirect PTPRG targets, possibly resulting in inhibition (SRC, KIT, ABL1, BTK, CDK2, JAK2, KDR, PDGFRB) or activation (ZAP70, PDGFRA) of their functional activities.

Example 5

JAK2 Mediates LFA-1 Affinity Triggering and Mediated Adhesion by Chemoattractants in Human Primary Monocytes In this example we show that JAK2 mediates chemoattractant-triggered signal transduction leading to human primary monocytes integrin activation and adhesion, identifying JAKs as general upstream transducers controlling pro-adhesive chemoattractant signaling in human leukocytes.

JAK2 regulation by PTPRG as assessed through the high-throughput phospho-proteomics analysis evidenced that PTPRG activation (Example 4, Table 9 and 10) provides a useful example of the exploitation of this analysis system for identification of targets and unexpected indications/uses for known and novel agents that regulate the phoshoproteome. We previously demonstrated that JAKs regulate LFA-1 and VLA-4 activation by chemokines and mediated trafficking to secondary lymphoid organs by human primary T lymphocytes (Montresor, A. et al., 2013. J Cell Biol 203(6):1003-1019); however, the role of JAKs in integrin activation in primary monocytes is unknown. Furthermore, the capability of fMLP to trigger JAKs activation has never been observed. The results described in Example 4 unexpectedly implicate JAK2 de-phosphorylation by PTPRG as playing a role in the anti-adhesive role of PTPRG on monocytes. To test this system-generated hypothesis we first set out to define the role of JAK2 in fMLP-triggered rapid adhesion in monocytes. Time course experiments, either performed with ELISA assay or Western Blot. Briefly, purified human monocytes were treated with buffer (resting) or with 50 nM fMLP for the indicated times (Table 12), and the phosphorylation was assessed by p-Jak2 elisa and Western Blot analysis. The JAK2 activation was determined with Elisa Kit JAK2 (pYpY1007/1008) (Invitrogen). Briefly, cells were stimulated with agonist and lysed following manufacturer's protocol; levels of phospho-JAK2 were quantified (absorbance at 450 nm) with a micro-well plate reader (Victor™ X5 Multilabel Plate Reader, Perkin Elmer). The mean values of 3 experiments induplicate are shown in Table 12. For Western blot analysis, cells were lysed in ice-cold 1% Nonidet P-40 buffer, containing phosphatase inhibitors and complete protease inhibitor cocktail (Roche). Total cell lysates were quantified by Bradford assay (Bio-Rad). Equal amounts of total lysates or of isolated membranes (as described in Example 1) were subjected to 10% SDS-PAGE and then blotted. After incubation with anti-PTPRG, anti gp91$^{Phox}$, anti phospho-JAK2, anti JAK2 and HRP-linked secondary antibodies (GE Healthcare), immunoreactive bands were visualized by ECL detection (EMD Millipore). Intensities of band signals were quantified by densitometric analysis (Quantity One, Bio-Rad) by using ImageQuant Las4000. Data are mean value of three experiments; the relative ratio of the band intensity of phosphor-JAK2 was normalized to the level of JAK2 band intensities. Data in Table 12 shows that JAK2 is effectively phosphorylated and activated in monocytes stimulated by fMLP.

TABLE 12

JAK2 PTK is activated by fMLP Stimulation

| | ELISA | | WESTERN BLOT | |
|---|---|---|---|---|
| | Mean | St. Dev | Mean | St. Dev |
| Resting | 100.0 | 0.0 | 20.2 | 2.0 |
| 90" | 107.3 | 2.5 | 37.8 | 2.4 |
| 120" | 128.3 | 2.9 | 46.7 | 1.8 |
| 180" | 155.7 | 5.1 | 58.5 | 1.6 |

To evaluate whether JAK2 mediates fMLP-triggered rapid adhesion in human monocytes, we tested the capability of three JAK inhibitors, AG490, WHI-P154 and P1-TKIP peptide, to block adhesion triggering. Briefly, Monocytes were treated with buffer (resting and Control=CTRL), 100 µM AG490, 40 µM P1 or P1-TKIP peptides, or 200 µM WHI-P154 for 1 hour at 37° C. and stimulated with 50 nM fMLP for 180 sec. Cell lysates were probed with anti phospho-JAK2 and with anti JAK2. Western Blot immuoreactive band quantification; the relative ratio of the band intensity of phospho-JAK2 was normalized to the level of JAK2 band intensities; mean values of three experiments (Table 13). All the inhibitors completely prevented fMLP-induced tyrosine autophosphorylation and activation of JAK, whereas the P1 control peptide was ineffective (Table 12).

TABLE 13

JAK2 Inhibitors Prevent Chemoattractant-induced Tyrosine Phosphorylation and Activation of JAK

| | Resting | CTRL | AG490 | P1 | P1-TKIP | WHI-P154 |
|---|---|---|---|---|---|---|
| Mean | 18.8 | 207.7 | 9.2 | 111.4 | 9.2 | 4.9 |
| St. Dev. | 1.3 | 15.5 | 1.1 | 26.5 | 1.5 | 2.2 |

To evaluate whether JAK2 mediates chemoattractant-induced adhesion of human monocytes to beta-2 integrin substrates human monocytes were treated control buffer or P1 or with the three JAK inhibitors. Briefly, human monocytes were treated with buffer (CTRL=control), or 40 μM P1 or P1-TKIP peptides, 100 μM AG490 or 200 μM WHI-P154 for 1 hour at 37° C. and stimulated with 50 nM fMLP for 60 sec.; data are mean and standard deviation (SD) of 6 experiments in triplicate.

TABLE 14

JAK2 Inhibitors Block Chemoattractant-induced Adhesion of Human Monocytes to Both Fibrinogen and ICAM-1

|  | Fibrinogen | | ICAM-1 | |
| --- | --- | --- | --- | --- |
|  | mean | SD | mean | SD |
| CTRL | 100 | 0 | 100 | 15 |
| P1 | 110 | 15 | 101 | 17 |
| P1-TKIP | 23.5 | 12 | 37.2 | 10 |
| AG490 | 32.8 | 11 | 23.5 | 17 |
| WHI-P154 | 18 | 8 | 6.4 | 5 |

Importantly, the three JAK inhibitors blocked fMLP-induced adhesion to both fibrinogen and ICAM-1 (Table 14) thus implying a role for JAKs in β2-integrins activation. Further, JAK inhibition also prevented rapid arrest on ICAM-1 in underflow assays (Table 15). Briefly, Human monocytes were treated with buffer (CTRL=control), 100 μM AG490, 40 μM P1 or P1-TKIP peptides or 200 μM WHI-P154 for 1 hour at 37° C. Shown are percentages of rolling and arrested cells for the indicated times over total interacting cells; mean values of of 5 experiments; errors bars are SDs.

TABLE 15

JAK2 Inhibitors Control Chemoattractant-induced Adhesion of Human Monocytes in Flow-Based Assays

|  | rolling | | arrest 1 sec | | arrest 10 sec | |
| --- | --- | --- | --- | --- | --- | --- |
|  | mean | SD | mean | SD | mean | SD |
| CTRL | 40 | 7 | 34 | 4 | 26 | 7 |
| P1 | 44 | 8 | 26 | 3 | 30 | 9 |
| P1-TKIP | 67 | 9 | 20 | 5 | 13 | 5 |
| AG490 | 70 | 6 | 20 | 5 | 10 | 2 |
| WHI-P154 | 66 | 6 | 20 | 5 | 14 | 1 |

Finally, JAK inhibitors blocked LFA-1 triggering to high affinity state (Table 16). Briefly, LFA-1 high affinity state detection. Human monocytes were treated with buffer (CTRL=control), 40 μM P1 or P1-TKIP peptides, 100 μM AG490 or 200 μM WHI-P154 for 1 hour at 37° C. and stimulated with 50 nM fMLP for 60 sec. LFA-1 high affinity state conformer was detected by cytofluorimetric analysis with 327C antibody. Shown are percentages of fold increases over the control; mean values of 5 experiments.

TABLE 16

JAK2 inhibitors control LFA-1 high affinity state triggering by chemoattractant

|  | CTRL | P1 | P1-TKIP | AG490 | WHI-P154 |
| --- | --- | --- | --- | --- | --- |
| Mean | 100 | 90 | 47 | 66 | 58 |
| St. Dev. | 0 | 5 | 10 | 5 | 3 |

Example 6

JAK2 is a PTPRG Target

In this example we demonstrate that JAK2 is a direct PTPRG target and, together with example 5, demonstrate that the anti-adhesive effect of increasing PTPRG activity involves JAK2 tyrosine dephosphorylation. Briefly, PTPRG activation by the P1-WD peptide affected the tyrosine phosphorylation of several signaling molecules and high-throughput phospho-proteomics analysis of PTPRG activation revealed JAK2 as a potential target for further investigation (Example 4) leading to the discoveries detailed in Example 5 showing that JAK2 mediates LFA-1 affinity triggering and mediated adhesion by chemoattractants in human primary monocytes.

First, we show in ELISA assay that in monocytes treated with the P1-WD peptide (Table 17) or with the TAT-ICD (Table 18) and then stimulated with fMLP, JAK2 tyrosine phosphorylation is effectively reduced, thus indicating inhibition of the JAK2 tyrosine kinase activity by PTPRG activation. Briefly, p-JAK2 ELISA assay on human monocytes treated with buffer (CTRL=control), 50 μM P1-WD, P1 or P1-WD scrambled peptides (Table 17), or with buffer (CTRL=control), 0.5 uM TAT-ICD or 50 μM TAT peptide (Table 18) for 1 hour at 37° C. and stimulated with 50 nM fMLP for 90 sec. Shown are percentages of fold increases over the control; mean values of 3 experiments in triplicate.

TABLE 17

Activation of PTPRG using P1-WD Effectively Blocks JAK2 Tyrosine Kinase Activity Induced by Chemoattractants

|  | mean | SD |
| --- | --- | --- |
| CTRL | 100 | 0 |
| P1-WD | 51 | 4 |
| P1 | 95 | 2 |
| P1-WD, scrambled | 92 | 5 |

TABLE 18

Activation of PTPRG using TAT-ICD Effectively Blocks JAK2 Tyrosine Kinase Activity Induced by Chemoattractants

|  | Mean | St. Dev |
| --- | --- | --- |
| CTRL | 100 | 0 |
| TAT-ICD | 53 | 8 |
| TAT | 99 | 5 |

The results from the p-JAK2 ELISA assays show that monocytes treated with the P1-WD peptide (Table 17) or with the TAT-ICD (Table 18) and then stimulated with fMLP, JAK2 tyrosine phosphorylation is effectively reduced, thus indicating inhibition of the JAK2 tyrosine kinase activity by PTPRG activation.

The impact of TAT-ICD and P1-WD on JAK2 activation by chemoattractants was also evaluated by Western Blot analysis. Briefly, monocytes were treated with buffer (Resting, CTRL), 0.5 uM TAT-ICD, 50 μM TAT peptide, 50 μM P1-WD, P1 or P1-WD scrambled peptides for 1 hour at 37° C. and stimulated with 50 nM fMLP for 180 sec (the resting cells were not stimulated with fMLP). Total lysates were probed with anti phospho-JAK2 or with anti JAK. Western Blot immunoreactive bands were quantified and the relative ratio of the band intensity of phospho-JAK2 was normalized to the level of JAK2 band intensities; data are mean value and standard deviation of three experiments (Table 19).

TABLE 19

Activation of PTPRG using TAT-ICD or P1-WD Effectively Block JAK-2 Phosphorylation Induced by Chemoattractants

|  | Mean | St. Dev. |
|---|---|---|
| Resting (no fMLP) | 8 | 2 |
| CTRL | 50 | 4 |
| TAT | 40 | 4 |
| TAT-ICD | 15* | 7 |
| P1 | 49 | 5 |
| P1-WD Scrambled | 56 | 12 |
| P1-WD | 12* | 4 |

*$P < 0.001$ compared to stimulated, control sample

These data (Table 19) confirmed that TAT-ICD and P1-WD almost completely prevented fMLP induced tyrosine phosphorylation of JAK2 in human monocytes, whereas the control P1, P1-WD-scrambled and TAT peptides were completely ineffective.

Finally, we performed a protein-protein interaction assay based on a substrate trapping approach by using the phosphatase defective PTPRG D1028A mutant (Blanchetot C et al 2005 Methods 35: 44-53). Briefly, 30 µl of HIS-Select Nickel Affinity Gel (Sigma-Aldrich), previously washed three times with TBS and with Bacterial lysis buffer, were incubated for 3 hours at 4° C. with 3 mg of quantified supernatants expressing TAT-ICD-D1028A mutant or TAT-eGFP, under constant rotation. After three hours, the nickel affinity gel was washed 3 times with monocyte lysis buffer. Each reaction, containing immobilized TAT-ICD-D1028A or TAT-eGFP in 30 µl of HIS-Select Nickel Affinity Gel, was incubated with 500 µg of monocytic lysate treated with buffer (CTRL) or with 50 nM fMLP for three hours at 4° C. with constant mutation. After incubation, beads were washed at least 3 times in monocyte lysis buffer and in TBS. Proteins were eluted from the beads in SDS sample buffer and resolved by SDS-PAGE and Western Blot Analysis. Blots were probed with anti-JAK2 Mab to detect whether JAK2 was bound to the TAT-ICD-D128A mutant protein; data are mean values of 3 experiments; errors bars are SD (Table 20)

TABLE 20

JAK2 Binds to PTPRG: demonstrated using a Phosphatase-defective PTPRG Mutant

|  |  | Mean | Std Dev |
|---|---|---|---|
| TAT-ICD-D1028A | Resting | 22.3 | 3 |
|  | fMLP 50 nM | 46.1 | 5 |
| TAT-GFP | Resting | 4.4 | 1.6 |
|  | fMLP 50 nM | 1.5 | 0.3 |

These results (Table 20) showed a JAK2 direct interaction with TAT-ICD-D1028A, but not with the negative control TAT-eGFP. Interestingly, we also observed an increased JAK2 binding upon fMLP treatment, suggesting that the JAK2 tyrosine phosphorylation may increase the binding affinity for PTPRG.

Example 7

TAT-ICD and P1-WD Treatment Results in a Time- and Dose-Dependent Blockade of Survival and Cell Proliferation, Triggers Apoptosis of GBM Cells In this example we demonstrate that treatment of glioblastoma (GBM) cells with an effective dose of agents of this invention results in a time- and dose-dependent blockade of survival and proliferation and triggers apoptosis Briefly, U251 GBM cells, normal primary cortical murine neurons and a mixed culture of murine microglia and astrocytes were treated for 24, 48 and 72 hours with no treatment (control), delivery peptide (P1 or TAT) or increasing concentrations of P1-WD or TAT-ICD. Cell viability and survival was measured using the MTT assay, a colorimetric assay for assessing cell metabolic activity set up under conditions where the absorption reflects the number of viable cells present (Table 21 and 22) and expressed as relative absorption at 570 nM. Early apoptosis was measured using VYBRANT DyeCycle Violet stain (Molecular Probes), a DNA-selective, cell membrane-permeant dye that can distinguish the compacted state of the nuclear chromatin in apoptotic cells as determined by flow cytometry and presented as the percent of cells that are apoptotic (Table 23 and 24). The actual number of cells following treatment with TAT-ICD or TAT alone (Table 25) was determined using flow cytometry compared to an input of 5,000 cells at time zero. To confirm apoptosis the TUNEL labeling assay, which detects DNA strand breaks in apoptotic cells by fluorescence microscopy, was also used to examine U251 cells treated with the PTPRG WD. Briefly, the assay used an optimized terminal transferase (TdD) to label 3'OH ends in genomic DNA with TMR-dUTP, thus allowing the measurement and quantification of cell death by apoptosis. U251 cells were pretreated for 1, 3 and 6 hours with 50 µM P1-WD. Then cells were fixed and permeabilized, incubated with TUNEL reaction mixture for 1 h at RT, and then stained with DAPI (for nuclei detection) and with Alexa670-Phalloidin (to detect actin in cell membranes). After the staining steps, cells were visualized with a confocal microscope.

TABLE 21

TAT-ICD treatment reduces U251 GBM cell survival

| Time of | 24 hrs | | 48 hrs | | 72 hrs | |
|---|---|---|---|---|---|---|
| treatment | mean | SD | mean | SD | mean | SD |
| Control | 821 | 10 | 1943 | 20 | 2556 | 20 |
| TAT 50 uM | 825 | 20 | 1654 | 20 | 2068 | 20 |
| TAT-ICD (uM) 0.5 | 568 | 15 | 969 | 10 | 1630 | 10 |
| 1.0 | 353 | 12 | 526 | 15 | 830 | 10 |
| 2.0 | 244 | 6 | 236 | 16 | 279 | 20 |

TABLE 22

Dose-dependent decrease in survival of TP1-WD treated U251 GMB

| Time of | 24 hours | | 48 hours | | 72 hours | |
|---|---|---|---|---|---|---|
| treatment | mean | sd | mean | sd | mean | sd |
| control | 821 | 10 | 1943 | 20 | 2556 | 20 |
| P1: 50 uM | 600 | 20 | 1743 | 20 | 2294 | 15 |
| P1 WD: 10 uM | 656 | 20 | 1400 | 20 | 1593 | 20 |

TABLE 22-continued

Dose-dependent decrease in survival of TP1-WD treated U251 GMB

| Time of treatment | 24 hours | | 48 hours | | 72 hours | |
|---|---|---|---|---|---|---|
| | mean | sd | mean | sd | mean | sd |
| 25 uM | 469 | 11 | 820 | 25 | 1281 | 25 |
| 50 uM | 411 | 13 | 733 | 10 | 1060 | 10 |

The data in Tables 21 and 22 are relative absorption using the MTT assay and show a dose dependent decrease of the proliferation and/or survival of GMB cells treated with PTPRG ICD or WD whereas there is no impact of treatment with the delivery peptides alone, even at much higher concentrations.

TABLE 23

TAT-ICD9 treatment results in dose-dependent increases of early apoptosis on U251 GMB cells

| | | Time of treatment | | |
|---|---|---|---|---|
| | | 6 hr | 9 hr | 24 hr |
| CTRL | | 4.6 | 6.0 | 7.0 |
| TAT | 50 uM | 10.0 | 11.0 | 8.0 |
| TAT-ICD | 0.5 uM | 2.6 | 14.0 | 21.0 |
| | 1 uM | 6.0 | 17.0 | 25.0 |
| | 2 uM | 15.0 | 25.0 | 30.0 |

TABLE 24

Dose-dependent increase in early apoptosis of P1-WD treated U251 GMB cells

| | | Time of treatment | | |
|---|---|---|---|---|
| | | 6 h | 9 h | 24 h |
| Control | | 5 | 12 | 8 |
| P1 | 50 μM | 8 | 15 | 15 |
| P1-WD | 10 μM | 13 | 21 | 25 |
| | 25 μM | 21 | 30 | 30 |
| | 50 μM | 33 | 40 | 40 |

Data are the percent of apoptotic cells

The data in Tables 23 and 24 are the percent of apoptotic cells as measured using the VYBRANT assay and show a dose dependent increase in apoptosis of GMB cells treated with PTPRG ICD or WD whereas there is little to no impact of treatment with the delivery peptides alone, even at much higher concentrations.

TABLE 25

TAT-ICD treatment of GMC cells decreases cell number

| Time of treatment (hours) | Control | TAT 50 50 μM | TAT-ICD 0.5 μM | 1 μM | 2 μM |
|---|---|---|---|---|---|
| Input | 5000 | 5000 | 5000 | 5000 | 5000 |
| 6 | 5000 | 4700 | 4676 | 2688 | 3943 |
| 9 | 10000 | 7000 | 5400 | 5434 | 3016 |
| 24 | 10000 | 11385 | 6094 | 5300 | 4500 |

Data are the number of cells per standard volume of medium compared to an input number of 5000 cells.

The data presented in Tables 21-25 show that treatment of U251 GBM cells with either the wedge domain, leading to PTPRG monomerization, or the ICD (D1+D2 intracellular domains with intrinsic phosphatase activity) resulted in a dose- and time-dependent decrease in survival (viability and/or proliferation) and increased early apoptosis of U251 GBM cells. This finding was validated using the TUNEL in situ apoptosis cell death detection staining. U251 cells treated with P1-WD showed fragmented DNA as early as 3 hours after initiation of treatment, and increased further from 6-24 hours indicating apoptosis, whereas cells treated with a scrambled, inactive version of P1-WD or the delivery peptides P1 or TAT alone did not show fragmented DNA or cell loss.

In striking contrast, treatment of normal primary cortical neurons isolated from mouse pups treated with TAT alone or TAT-ICD for 24-72 hours (Table 26) are mean and sd of absorption using the MTT assay as described above.

TABLE 26

TAT-ICD treatment does not impact normal primary mouse neuron viability

| | | 24 hours | | 48 hours | | 72 hours | |
|---|---|---|---|---|---|---|---|
| | | mean | sd | mean | sd | mean | sd |
| Control | | 1116 | 20 | 1022 | 12 | 994 | 20 |
| TAT (uM) | 0.1 | 1150 | 30 | 1151 | 35 | 1151 | 30 |
| | 0.25 | 908 | 50 | 955 | 70 | 957 | 50 |
| | 0.5 | 1184 | 20 | 1148 | 35 | 1224 | 42 |
| TAT-ICD (uM) | 0.1 | 1115 | 15 | 989 | 12 | 1074 | 70 |
| | 0.25 | 928 | 40 | 923 | 3 | 1204 | 35 |
| | 0.5 | 1164 | 15 | 1109 | 10 | 1376 | 10 |

Data are absorbance in the MTT assay; mean +/− SD

TABLE 27

TAT-ICD does not impact viability or proliferation of bEnd3 endothelial cells

| | | Time of treatment | |
|---|---|---|---|
| | | 24 hours | 48 hours |
| CTRL | | 352 | 523 |
| TAT (uM) | 0.1 | 354 | 503 |
| | 0.25 | 338 | 540 |
| | 0.5 | 328 | 528 |
| TAT-ICD (uM) | 0.1 | 373 | 513 |
| | 0.25 | 378 | 579 |
| | 0.5 | 393 | 545 |

Data are mean absorbance in the MTT assay

TABLE 28

TAT-ICD does not impact viability or proliferation of COS7 cells

| | | Time of treatment | | |
|---|---|---|---|---|
| | | 24 hours | 48 hours | 72 hours |
| CTRL | | 700 | 1267 | 1500 |
| TAT (μM) | 0.1 | 649 | 1320 | 1495 |
| | 0.25 | 624 | 1250 | 1388 |
| | 0.5 | 650 | 1289 | 1341 |
| TAT-ICD (μM) | 0.1 | 674 | 1391 | 1481 |
| | 0.25 | 684 | 1289 | 1489 |
| | 0.5 | 694 | 1295 | 1461 |

Data are mean absorbance in the MTT assay

Table 27 and 28 show that treatment with TAT-ICD does not impact the viability or proliferation of bEnd3 cells, an endothelial polyoma middle T antigen transformed cell line (Table 27) or COS7, a kidney fibroblast cell line (Table 28).

Activation of PTPRG resulted in reduced survival and increased apoptosis in three additional glioblastoma-derived cell lines DBTRG, U87MG and T98G, using the MTT colorimetric assay to assess survival (data are relative absorption, mean+/−SD) and the VYBRANT Violet flow-cytometry assay to measure apoptosis (by flow cytometry; data expressed as the percent of apoptotic cells).

The DBTRG-O5MG (Denver Brain Tumor Research Group 05) cell line was established from tissue from a patient with glioblastoma multiforme who had been treated with local brain irradiation and multi drug chemotherapy (Kruse C A, et al. 1992 In vitro Cell Dev Biol, 28A(9-10): 609-14). U87 is a commonly studied and thoroughly characterized grade IV glioma cell line derived from malignant glioma (Clark M J, et al, 2010 Plos Genet. 6(1):e1000832.). T98G is a glioblastoma multiforme cell line extracted from a 61 years Caucasian male (Stein G H, 1979, J. Cell Physiol, 99(1):43-54). Proliferation and survival were assessed following TAT-ICD or control peptide (Table 29) or the P1-WD or control peptide treatment using the MTT assay as described above. Data are relative absorption; mean and standard deviation.

TABLE 29

Dose-dependent decrease in survival of TAT-ICD treated T98G GBM cells

| Time of treatment | | 24 hours | | 48 hours | | 72 hours | |
|---|---|---|---|---|---|---|---|
| | | mean | SD | mean | SD | mean | SD |
| CTRL | | 971 | 20 | 1305 | 20 | 1481 | 20 |
| TAT | 500 µM | 954 | 20 | 1237 | 10 | 1205 | 20 |
| TAT-ICD | 0.5 µM | 921 | 18 | 1301 | 15 | 1061 | 35 |
| | 1 µM | 745 | 15 | 947 | 20 | 935 | 30 |
| | 2 µM | 552 | 20 | 687 | 30 | 625 | 10 |

Data are absorbance in the MTT assay for the time-point indicated; mean +/− SD

TABLE 30

Decrease in survival of P1-WD-treated T98G GMB cells

| Time of treatment | | 24 hours | | 48 hours | | 72 hours | |
|---|---|---|---|---|---|---|---|
| | | mean | sd | mean | sd | mean | sd |
| Control | | 971 | 20 | 1305 | 3 | 1481 | 30 |
| P1 | 50 µM | 1113 | 20 | 1019 | 20 | 1111 | 35 |
| P1-WD | 10 µM | 629 | 25 | 854 | 2 | 985 | 20 |
| | 25 µM | 555 | 13 | 697 | 7 | 835 | 25 |
| | 50 µM | 540 | 20 | 744 | 15 | 842 | 10 |

Data are absorbance in the MTT assay; mean +/− SD

Treated with increasing doses of TAT-ICD and with the TAT control peptide for 24, 48 and 72 hours (Table 29) or with P1-WD or the P1 delivery peptide only (Table 30) show a time- and dose-dependent decrease in proliferation and survival of cells upon the treatment with the PTPRG WD or ICD, with little to no effect of the control peptides.

TABLE 31

TAT-ICD decreases survival of DBTRG GBM cells

| Time of treatment | | 24 hours | | 48 hours | | 72 hours | |
|---|---|---|---|---|---|---|---|
| | | mean | SD | mean | SD | mean | SD |
| Control | | 941 | 16 | 1274 | 12 | 1667 | 6 |
| TAT (µM) | 0.3 | 711 | 8 | 1031 | 20 | 1583 | 52 |
| | 0.5 | 826 | 6 | 1061 | 35 | 1591 | 14 |
| | 1.0 | 792 | 50 | 1005 | 2 | 1275 | 32 |
| TAT-ICD (µM) | 0.3 | 772 | 16 | 770 | 15 | 1243 | 13 |
| | 0.5 | 773 | 25 | 623 | 41 | 1022 | 4 |
| | 1.0 | 669 | 50 | 577 | 35 | 712 | 40 |

Data are relative absorption; mean and SD

TABLE 32

TAT-ICD induces early apoptosis in DBTRG GBM cells

| Time of treatment | Control | TAT 0.5 µM | TAT-ICD 0.5 µM |
|---|---|---|---|
| 1 h | 14 | 10 | 25 |
| 3 h | 16 | 10 | 40 |
| 6 h | 33 | 7 | 70 |

Data are the percent of apoptotic cells by flow cytometry

Treatment of DBTRG cell line with PTPRG ICD reduces proliferation and/or survival (Table 31) and increases apoptosis (Table 32) of DBTRG GMB cells.

TABLE 33

TAT-ICD treatment decreases survival of U87 GBM cells

| Time of treatment | | 24 hours | | 48 hours | | 72 hours | |
|---|---|---|---|---|---|---|---|
| | | Mean | SD | Mean | SD | Mean | SD |
| CTRL | | 1200 | 10 | 1200 | 45 | 1336 | 39 |
| TAT (µM) | 0.1 | 1200 | 7 | 1018 | 15 | 1343 | 6 |
| | 0.25 | 1195 | 35 | 950 | 40 | 1200 | 60 |
| | 0.5 | 1160 | 2 | 900 | 23 | 1235 | 13 |
| TAT-ICD (µM) | 0.1 | 1070 | 30 | 1167 | 4 | 813 | 40 |
| | 0.25 | 1069 | 20 | 1062 | 16 | 650 | 12 |
| | 0.5 | 1000 | 12 | 977 | 18 | 650 | 15 |

TABLE 34

TAT-ICD induces apoptosis of U87 GBM cells

| Time of treatment | Control | | TAT 0.5 µM | | TAT-ICD 0.5 µM | |
|---|---|---|---|---|---|---|
| | Mean | SD | Mean | SD | Mean | SD |
| 1 hour | 10 | 3 | 20 | 10 | 67 | 5 |
| 3 hours | 3 | 5 | 10 | 2 | 60 | 6 |
| 6 hours | 14 | 5 | 20 | 5 | 70 | 8 |

PTPRG ICD treatment results in a time- and dose-dependent decrease in proliferation and/or survival (Table 33) and increases apoptosis (Table 34) of U87 GMB cells.

Example 8

The Extracellular Domain of PTPRG (PTPx) Activates PTPRG Activity: Soluble PTPx Inhibits LFA-1 Mediated Adhesion by Chemoattractant Triggered Human Monocytes This example demonstrates that an effective dose of the external domain of PTPRG (PTPx) can block leukocyte activation and adhesion The external domain of PTPRG, PTPx (amino acids 20-736, SEQ ID NO 7), was produced with a histidine tag using a Human Cell-Free Protein Expression System by TAKARA and purified using Dynabeads using the his-tag. Human primary monocytes were isolated from buffy coats from healthy donors and pre-incubated for 30 minutes at room temperature with our without 0.075 micromolar PTPX. Standard adhesion assays on ICAM-1 coated glass slides. Cell suspensions were added to the coated wells for 1 minute, stimulated for 1 minute at 37° C. with 50 millimolar fMLP. Non-adherent cells were washed away and adherent cells were fixed in ice-cold 1.5% glutaraldehyde in PBS and adherent cells were counted using computer assisted automatic quantification. Data are from a representative experiment and are the mean and standard deviation of 24 measurements per condition (Table 35).

SEQ ID NO:7: PTPRG extracellular domain; PTPx; aa 20-736 actual sequence is at the end of the document,

TABLE 35

PTPx reduces chemoattractant-stimulated adhesion of human monocytes to ICAM-1

|  | No Agonist | | 50 nM fMLP | |
|---|---|---|---|---|
|  | Mean | SD | MEAN | SD |
| Control | 22.2 | 12.0 | 212.8 | 77.7 |
| PTPx | 3.4 | 2.1 | 32.7 | 27.2 |

Stimulation of monocytes with fMLP triggers an approximately 10-fold increase in adhesion to ICAM-1. Treatment of the neutrophils with PTPx blocked adhesion of both unstimulated (no agonist) and fMLP-stimulated adhesion compared to untreated neutrophils (Table 35). These results demonstrate that nextracellular domain, or components of the extracellular domain, are able to trigger PTPRG activation and reduction of leukocyte adhesion and that the extracellular domain is a viable pharmacological target.

Example 9

TAT-ICD Treatment Ameliorates β-Thalassemic Anemia

This example demonstrates that in vivo administration of an effective dose of PTPRG ICD using a delivery peptide improves erythropoiesis and ameliorates β-thalassemic anemia. We demonstrate: a) marked reduction in PTPRG activity in erythroblasts in Hbb$^{th3/+}$ mice compared to wild type mice; b) that administration of an effective dose of TAT-ICD to β-thalassemic mice significantly normalizes key hematological parameters and red cell indices (Table 37), including normalization of hemoglobin and mean corpuscular volume of circulating red cells, significant reduction/normalization of reticulocyte counts, increase/normalization of mean corpuscular volume in circulating reticulocytes, and amelioration of abnormal red cell morphology, c) a significant improvement in the alpha/beta globulin ratio (Table 38); d) reduction in abnormally high levels of reactive oxygen species in β-thalassemic red cells (Table 39); e) reduction in abnormally high levels of circulating erythroblasts (Table 40); f) normalization of the percent of bone marrow erythroid precursors (Table 41); and g) reduction in apoptosis of late-stage (orthochromatic) erythroblasts in bone marrow (Table 42).

β-thalassemia and β-thalassemic syndromes are characterized by mild to severe anemia due to the combination of ineffective erythropoiesis and severe red cell membrane oxidative damage. Ineffective erythropoiesis is sustained by a block in erythroid maturation process combined with increased apoptosis in late stage erythropoiesis.

Wild-type C57BL/6J mice and the mouse model for β-thalassemia (designated as Hbb$^{th3/+}$) were used for these studies. Flow cytometric analysis and sorting of mouse bone marrow and spleen precursors were performed using standard protocols using markers for CD44 and TER119 and cell size (forward scatter) to distinguish erythroid precursors at each distinct developmental stage. Forward scatter high-CD44+Ter119+ cells represents total erythroblasts (or erythroid mass in bone marrow or spleen). These erythroblasts can be further analyzed and sorted in subpopulations: population I: pro-erythroblasts; population II: basophilic erythroblasts; population III: polychromatic erythroblasts; population IV: orthochromatic erythroblasts, as described in Matte et al 2015, Antioxid. Redox Signal. 2015 23(16): 1284-1297. Population II, III and IV corresponding to basophilic erythroblasts, polychromatic erythroblasts and orthochromatic erythroblasts were sorted from bone marrow as previously described (Matte et al 2015 Antioxid. Redox Signal. 2015 23(16):1284-1297).

The tyrosine-phosphoproteome of the sorted polychromatic erythroblasts and orthochromatic erythroid precursors from both WT and Hbb$^{th3/+}$ mice were analyzed using tyrosine phosphor arrays by Kinexus, as described in example 4 above. As shown in Table 36, the tyrosine phosphorylation pattern was different in healthy WT control and Hbb$^{th3/+}$ polychromatic erythroblasts and orthochromatic erythroid precursors. Data in Table 36 are the globally normalized signal intensity, performed by Kinexus using standard procedures. The % CFC is the percent change of the thalassemic sample in normalized intensity from the wild-type control sample. For example, a % CFC value of 100% corresponds to a 2-fold increase in signal intensity with the treatment. A negative % CFC value indicates the degree of reduction in signal intensity from the selected control. Calculation=[(Globally Normalized Treated/Globally Normalized Control)*100]−100

TABLE 36

Altered tyrosine-phosphorylation pattern of intracellular signaling in sorted β-thalassemic erythroblasts and orthochromatic erythroid percursors compared to wild-type cells

| Target Protein | Full Name of Target Protein | Phospho Site (Human) | Globally Normalized/ WT cells | Globally Normalized/ Thalassemic cells | % CFC |
|---|---|---|---|---|---|
| PKR1 | Double stranded RNA dependent protein-serine kinase | Pan-specific | 428 | 2685 | 530 |

TABLE 36-continued

Altered tyrosine-phosphorylation pattern of intracellular signaling in sorted β-thalassemic erythroblasts and orthochromatic erythroid percursors compared to wild-type cells

| Target Protein | Full Name of Target Protein | Phopspho Site (Human) | Globally Normalized/ WT cells | Globally Normalized/ Thalassemic cells | % CFC |
|---|---|---|---|---|---|
| DDR1 | Epithelial discoidin domain-containing receptor 1 | Y796 + pY797 | 1525 | 2472 | 63 |
| GSK3a | Glycogen synthase-serine kinase 3 alpha | Y284 + Y285 | 1342 | 2198 | 65 |
| MST1 | Mammalian STE20-like protein-serine kinase 1 (KRS2) | Pan-specific | 801 | 1356 | 70 |
| CDK1 | Cyclin-dependent protein-serine kinase 1 | Y19 | 705 | 1346 | 92 |
| AK2 | Adenylate kinase 2 | Pan-specific | 830 | 1247 | 51 |
| Akt1 (PKBa) | RAC-alpha serine/threonine-protein kinase | Pan-specific | 3075 | 6581 | 115 |
| Chk1 | Checkpoint protein-serine kinase 1 | S345 | 2122 | 3224 | 53 |
| DUSP12 | Dual specificity protein phosphatase 12 | Pan-specific | 3834 | 6137 | 61 |
| Grp94 | Glucose regulated protein 94 (endoplasmin) | Pan-specific | 4850 | 7508 | 56 |
| JAK2 | Janus protein-tyrosine kinase 2 | Pan-specific | 6532 | 10178 | 57 |
| JNK1 | Jun N-terminus protein-serine kinase (stress-activated protein kinase (SAPK)) 1 | Pan-specific | 9738 | 15184 | 57 |
| Met | Hepatocyte growth factor (HGF) receptor-tyrosine kinase | Y1003 | 1396 | 2126 | 53 |
| PAK4 | p21-activated kinase 4 | S474 | 4503 | 9299 | 108 |
| PDGFRa | Platelet-derived growth factor receptor kinase alpha | Y754 | 2000 | 3820 | 92 |
| PRP4K | Protein-serine kinase PRP4 homolog | Y849 | 1817 | 3237 | 79 |
| SMC1 | Structural maintenance of chromosomes protein 1A | S957 | 3141 | 5015 | 60 |
| Src | Src proto-oncogene-encoded protein-tyrosine kinase | Pan-specific | 12806 | 19122 | 50 |
| Fos | Fos-c FBJ murine osteosarcoma oncoprotein-related transcription factor | Pan-specific | 863 | 1388 | 62 |
| PKR1 | Double stranded RNA dependent protein-serine kinase | Pan-specific | 1163 | 549 | −53 |

The data in Table 36 show that the tyrosine phosphorylation status of proteins in polychromatic erythroblasts and orthochromatic erythroid precursors are different between healthy wild-type and Hbb$^{th3/+}$ mice. Of particular interest is the discovery of increased tyrosine phosphorylation on the functional targets, JAK2, PDGFRa, and Src. We showed that JAK2, PDGFRa and Src are among the key direct or indirect targets of PGPRG, as described in Example 4, and that JAK2 is a direct PTPRG target, in Example 6. Together these data demonstrate that modulation of PTPRG activity may be a viable strategy to treat beta-thalassemia.

We next showed a marked reduction in PTPRG expression in erythroblasts in Hbb$^{th3/+}$ mice compared to wild type mice. Briefly, we compared PTPRG expression in sorted erythroblasts (forward scatter high-CD44+Ter119+ cells) from wild-type and Hbb$^{th3/+}$ mice using immunoblot analysis using standard methods. Quantitation of immunoblots normalized against GAPDH revealed a 10-fold reduction in PTPRG expression in Hbb$^{th3/+}$ mice compared to wild-type.

We next show that treatment of β-thalassemic mice with PTPRG ICD is an effective therapeutic. Wild-type and Hbb$^{3th/+}$ were treated with TAT-ICD at 5 mg/kg i.p once every other day for 3 weeks. Body weight was monitored as a measure of toxicity and no changes were observed during the treatment period. Hematological parameters, red blood cell indices and reticulocyte counts were determined using standard procedures. Table 37 summarizes the effect of treatment of WT and HBB mice with TAT-ICD9 on key hematological parameters and red cell indices.

TABLE 37

TAT-ICD treatment significantly normalizes key hematological parameters and red cell indices in β-thalassemia in mice

| | WT mice | | Hbb$^{th/+}$ mice | |
|---|---|---|---|---|
| | Vehicle n = 12 | TAT-ICD n = 3 | Vehicle n = 14 | TAT-ICD n = 4 |
| Hct (%) | 45.2 ± 0.8 | 46.3 ± 0.5 | 28.6 ± 0.3° | 34.8 ± 4.9* |
| Hb (g/dl) | 14.7 ± 0.5 | 14.9 ± 0.4 | 8.8 ± 0.2° | 10.1 ± 0.3* |
| MCV (fL) | 45.4 ± 0.5 | 50.1 ± 0.1* | 34.7 ± 0.5° | 393 ± 0.9* |
| MCH (pg) | 14.5 ± 0.2 | 15.0 ± 0.7 | 9.4 ± 0.03° | 10.2 ± 0.4* |
| CH (%) | 12.7 ± 0.4 | 13.6 ± 0.2 | 9.7 ± 0.8° | 10.4 ± 0.3 |
| RDW (%) | 12.5 ± 0.1 | 13.6 ± 0.3* | 33.2 ± 0.6° | 25.7 ± 1.0* |
| Retics (%) | 3.1 ± 0.3 | 4.3 ± 0.5* | 27.7 ± 3.3° | 18.2 ± 2.0* |
| | 298 ± 21 | 406 ± 76* | 2140 ± 356 | 1640 ± 177* |
| MCVr (fL) | 56.2 ± 1.0 | 55.0 ± 0.3 | 44.9 ± 1.1° | 49.2 ± 1.2* |
| CHr (pg) | 14.5 ± 0.2 | 14.0 ± 0.1 | 9.2 ± 0.8° | 12.0 ± 0.39* |
| WBC (cells/uL) | 7900 ± 120 | 6005 ± 980 | 14363 ± 2614 | 9125 ± 1021* |

TABLE 37-continued

TAT-ICD treatment significantly normalizes key hematological parameters and red cell indices in β-thalassemia in mice

|  | WT mice | | Hbb3$^{th/+}$ mice | |
| --- | --- | --- | --- | --- |
|  | Vehicle n = 12 | TAT-ICD n = 3 | Vehicle n = 14 | TAT-ICD n = 4 |
| Neutrophil (cells/uL) | 987 ± 229 | 1833 ± 461 | 1366 ± 598 | 1407 ± 597 |

Hct: hematocrit;
Hb: hemoglobin;
MCV: mean corpuscular volume;
MCH: mean corpuscular hemoglobin;
CH: hemoglobin concentration;
RDW: red cell distribution width;
Retics: reticulocytes;
MCVr: mean corpuscular volume reticulocytes;
MCHr: mean corpuscular hemoglobin reticulocytes;
CHr: reticulocyte hemoglobin concentration;
RDWr: red cell distribution width reticulocytes;
*P < 0.05 compared to untreated mice;
°P < 0.05 compared to wild-type mice The data in Table 37 show that treatment of β-thalassemic mice with TAT-ICD resulted in a significant increase/normalization in hemoglobin levels, mean corpuscular volume, mean corpuscular hemoglobin and a reduction in the red cell distribution width, all to levels closer to the levels in normal, wild-type mice. These changes are associated with a significant reduction in reticulocyte counts and an increase in mean corpuscular volume in reticulocytes, a key marker of improved quality of hemoglobinization in the treated Hbb$^{th3/+}$ mice, without major changes in the hemoglobin levels in treated wild-type mice. Together these data show that in vivo treatment with the ICD is an effective therapeutic option for β-thalassemia.

Red cell morphology was assessed by microscopic analysis of peripheral blood smears ICD treatment ameliorated red cell morphological abnormalities in the Hbb$^{th3/+}$ mice without any changes in the wild-type treated mice.

We also observed a significant improvement in the α/β globin ratio with treatment of beta-thalassemic mice, a key measure of successful treatment of beta-thalassemia. The mutations in the beta-globin gene in beta-thalassemia results in absent or reduced synthesis of beta-globin chains leading to unbalanced globin chain synthesis and unpaired alpha-chain that form highly toxic aggregates in erythroid progenitors and red blood cells, and can be measured as a decrease in soluble alpha globulin. We measured the amount of soluble vs insoluble globulin not bound to heme (Table 38) and observed a significant (P<0001; 2 tailed T test) decrease in the percent of soluble alpha-globin in the beta-thalassemic mice compared to wild type mice (Table 38). Treatment of the beta-thalassemic mice with PTPRG ICD resulted in a significant increase in the percent of soluble alpha globin (P<0.05; Table 38) and reduction in the levels of alpha-globin precipitation in thalassemic red cells.

TABLE 38

Treatment with ICD results in a significant improvement in the percent of soluble alpha globulin

|  | Vehicle-treated | | ICD-Treated | |
| --- | --- | --- | --- | --- |
|  | Mean | S.D. | Mean | S.D. |
| Wild-type | 98.4 | 1.0 | 97.9 |  |
| Hbb$^{th3/+}$ | 87.9* | 2.5 | 92.5* | 2.3 |

Data are the percent of * P < 0.05 Student T Test

Reactive oxygen species (ROS) are known to be increased in red blood cells in β-thalassemia and are thought to be important in the pathophysiology of the disease, leading to cumulative cell damage. The reactive oxygen species (ROS) levels from erythroid precursor populations was assessed using the General Oxidative Stress Indicator CM-H2DCFDA (Life Technologies, Carlsbad, Calif.) as described (Matte A. et al 2015 Antioxid. Redox Signal 23(16):1284-1297). As seen in Table 39, treatment of β-thalassemic mice with TAT-ICD resulted in a significant reduction in the levels of reactive oxygen species (ROS) in the red cells. Data are the mean ROS level.

TABLE 39

Significant reduction in levels of reactive oxygen species (ROS) in red cells in β-thalassemic mice treated with ICD.

|  | Untreated | | ICD-Treated | |
| --- | --- | --- | --- | --- |
|  | Mean | S.D. | Mean | St. Dev. |
| Wild-type | 3.32 | 0.22 | 2.79 | 0.28 |
| Hbb$^{th3/+}$ | 13.75* | 0.85 | 9.73* | 1.56 |

*P < 0.05 Student T Test, 2 tailed

The levels of circulating erythroblasts were also significantly reduced in ICD-treated β-thalassemic mice (FIG. 40) indicating effective treatment of ineffective erythropoiesis.

TABLE 40

ICD-treatment results in a significant reduction in circulating Erythroblasts in β-thalassemic mice

|  | Vehicle-treated | | ICD-Treated | |
| --- | --- | --- | --- | --- |
|  | Mean | S.D. | Mean | S.D. |
| Wild-type | 0 | 0 | 0 | 0 |
| Hbb$^{th3/+}$ | 32.0* | 2.9 | 10.8* | 3.8 |

*P < 0.00001 Student T Test, 2 tailed

Ineffective erythropoiesis in β-thalassemia is characterized by a block in cell maturation with accumulation of erythroid precursors and increased cell apoptosis in late phase erythropoiesis in the bone marrow. TAT-ICD treatment of Hbb$^{th3/+}$ mice resulted in a significant reduction of β-thalassemic erythroid precursors (fsc high CD44+ TER119+ cells in bone marrow, compared to vehicle-treated Hbbth3+ mice (TABLE 41).

TABLE 41

Normalization of the percent of bone marrow erythroid precursors in ICD-treated β-thalassemia mice

|  | Vehicle-treated | | ICD-Treated | |
| --- | --- | --- | --- | --- |
|  | Mean | S.D. | Mean | S.D. |
| Wild-type | 20.0 | 2.5 | 13.9 | 4.0 |
| Hbb$^{th3/+}$ | 35.4* | 4.3 | 23.8* | 4.4 |

*P < 0.0005 Student T Test, 2 tailed

The data in Table 41 show that β-thalassemia mice have a significantly increased percent of erythroid precursors in bone marrow compared with wild-type control and that treatment of these mice with PTPRG ICD results in a significant reduction in the percent of bone marrow erythroid precursors, essentially normalizing the levels to those in wild-type mice. We also observed a trend to reduction of extramedullar erythropoiesis in spleen, a site of extramedullary erythropoiesis, in TAT-ICD-treated mice even after the relatively short treatment period (3 weeks).

Further analysis of the percent of the bone marrow erythroid precursor populations I, II, III and IV as described above reveals a significant decrease in the percent of proerythroblasts (population I) in $Hbb^{th3/+}$ mice (3.6+/−0.9) compared to wild-type control (6.5+/−0.9; P<0.00001) an a significant increase in orthochromatic erythroblasts (population IV) in $Hbb^{th3/+}$ mice (63.0+/−4.4) compared to wild type mice (54.1+/−2.4; P<0.0001). Treatment of $Hbb^{th3/+}$ mice with PTPRG ICD results in a statistically significant increases in the percent of proerythroblasts (P<0.001) back to normal levels (5.9+/−0.6). In addition, ROS levels, which are increased in all four populations in Hbb mice compared to wild type mice are decreased PTPRG ICD-treated mice in all four populations, in agreement with the decrease in ROS levels in circulating red cells (Table 39).

One of the hallmarks of β-thalassemia is increased apoptosis of late-stage erythroblasts. Apoptosis of population IV (orthochromatic erythroblasts) was assessed using standard protocols using the Annexin-V PE apoptosis kit following manufacturer instructions. Data are the mean percent of apoptotic cells (Table 42).

TABLE 42

Significant reduction in apoptosis of bone marrow orthochromatic erythroblasts ICD-treated β-thalassemia mice

|  | Vehicle-treated | | ICD-Treated | |
|---|---|---|---|---|
|  | Mean | S.D. | Mean | S.D. |
| Wild-type | 4.46 | 0.38 | 4.20 | 0.64 |
| $Hbb^{th3/+}$ | 8.78* | 0.35 | 5.75* | 1.02 |

*P < 0.00005 Student T Test, 2 tailed

Table 42 shows a significant increase in the percentage of apoptotic cells in the $Hbb^{th3/+}$ orthochromatic erythroblasts compared to wild-type (P<0.00001; two-tailed T test). Treatment for 3 weeks with ICD did not alter apoptosis in the wild-type mice; however, a significant reduction in apoptosis of $Hbb^{th3/+}$ orthochromatic erythroblasts from bone marrow of TAT-ICD treated $Hbb^{th3/+}$ mice was achieved.

Example 10

Modulation of PTPRG Activity Inhibits Chemoattractant-Triggered Adhesion of Human T Lymphocytes and Neutrophils This example demonstrates that chemoattractant-triggered T cell and neutrophil adhesion can be blocked by contacting the cells with an effective dose of PTPRG ICD and that chemoattractant triggered T cell adhesion is blocked by contacting the cells with an effective dose of PTPRG WD Static adhesion assays were performed as described in Example 2. T lymphocytes and neutrophils were isolated from human peripheral blood using standard protocols (Montresor A. et al, 2013 JCB 203(6):1003-19). T-lymphocyte adhesion assays were performed by pre-incubating cells for 1 h at 37° C. with increasing doses of P1-WD or TAT-ICD. Cells were then spotted on the ICAM-1 or VCAM-1 coated microscope slides and integrin-mediated adhesion was stimulated with 200 nM SDF-1 for 3 minutes. Non-adherent cells were washed away and adherent cells were fixed in glutaraldehyde (1.5%) in PBS. The number of adherent cells was measured as described in Example 2 using image acquisition and computer assisted enumeration using Image J.

TABLE 43

PTPRG wedge domain (WD) and ICD inhibit chemokine-triggered adhesion of human T-lymphocytes to ICAM-1 and VCAM-1

|  | No Stimulation | SDF-1 stimulated Binding | | | |
|---|---|---|---|---|---|
| Binding to: | Control | Control | PTPRG P1-WD (micromolar) | | |
|  |  |  | 5 | 10 | 25 | 50 |
| ICAM-1 | 23 ± 7 | 419 ± 100 | ND | 325 ± 103 | 245° ± 117 | 115* ± 39 |
| VCAM-1 | 9 ± 3 | 95 ± 5 | 51* ± 15 | 47* ± 6 | 34* ± 14 | 12* ± 2 |
|  | Control | Control | PTPRG TAT-ICD (micromolar) | | |
|  |  |  | 0.01 | 0.05 | 0.1 | 0.5 |
| ICAM-1 | 29 ± 6 | 164 ± 47 | 87* ± 18 | 80* ± 26 | 74* ± 37 | 80* ± 24 |

Data are mean+/−S.D.;
ND means not done
T test, two tailed, compared to stimulated, control-treated samples
°P < 0.001
*P < 0.0001

The data in Table 43 show that treatment of freshly isolated human T-lymphocytes with PTPRG-WD results in a significant, dose-dependent blockade of chemokine-stimulated adhesion to both ICAM-1 and VCAM-1. PTPRG ICD treatment also resulted in a significant reduction in adhesion of chemokine-stimulated adhesion to ICAM-1 (lower section, table 43).

Chemokine-triggered adhesion of human neutrophils was measured similarly. Freshly isolated, non-activated human neutrophils incubated with buffer or increasing concentrations of TAT-ICD and then spotted onto ICAM-1-coated slides. Integrin-mediated adhesion was triggered using 50 nM fMLP and the adherent cells were fixed and enumerated as described for the lymphocytes above.

TABLE 44

PTPRG ICD inhibits chemokine-triggered adhesion of human neutrophils to ICAM-1

|  |  | Resting (no stimulation) | Stimulated (50 nM fMLP) |
|---|---|---|---|
| Control |  | 12 ± 5 | 1107 ± 256 |
| TAT-ICD | 0.5 | 12 ± 5 | 545* ± 39 |
| (micromolar) | 1.0 | 12 ± 5 | 508* ± 120 |

Data are mean +/− SD
*P < 0.0001 compared to stimulated control wells, T test, two tailed.

It is shown in Table 1 that the wedge domain (P1-WD) is able to trigger a specific, dose-dependent increase in tyrosine phosphatase activity in monocytes but not in human PMN's, which is in agreement with the low to no expression of PTPRG in PMNs. P1-WD was not able to block chemokine-induced adhesion of PMN. It is shown in Example 3 that a TAT-ICD fusion protein has tyrosine phosphatase activity in an in vitro phosphatase assays (Table 5).

It is shown in Table 44 PTPRG TAT-ICD blocks chemokine-induced adhesion to ICAM-1 in a cell with little to no intrinsic PTPRG expression or activity. These data demonstrate that the intrinsic PTPRG tyrosine phosphatase activity in the PGPRT ICD functions as a therapeutic to prevent or treat disease involving dysregulated tyrosine kinase activity and/or signaling mechanisms involving tyrosine phosphorylation and/or tyrosine kinase activity, even when there is little to no PTPRG activity.

A number of conditions were found where there is statistically significant, non-random overlap of PTPRG targets in monocytes, and genes known to be involved or dysregulated in that condition, including conditions where PTPRG expression and/or activity is known to be decreased. Included are renal cell carcinoma, hepatocellular carcinoma and others. There are a number of conditions where the targets of PTPRG are known to be dysregulated, for example JAK2, and also a number of conditions where no previous association between PTPRG was known. Both glioblastoma and beta-thalassemia, shown herein to respond to PTPRG activity manipulation, were identified.

Example 11

Identification of Conditions or Disease with Dysregulated PTPRG Targets

In this example we identify conditions or diseases where there is a statistically significant, non-random overlap of PTPRG targets identified in Example 4 and the genes known to be involved or dysregulated in those conditions or diseases thereby identifying potential therapeutic indications where manipulation of PTPRG maybe therapeutically desirable.

In example 4 we identified key targets in human monocytes that are affected upon activation of PTPRG using the PTPRG WD. These key targets included several important protein kinases and other signaling molecules. Gene sets, including all targets dephosphorylated at any site or all targets activated were cross-referenced with gene sets known to be related to and/or dysregulated in disease using Enrichr: (Chen E Y et al 2013 BMC Bioinformatics. 2013; 128, 14) to query the OMIM disease gene data set. Briefly, Enrichr is an integrative web-based software application that enables users to compare a custom gene set to curated online gene-set libraries, for example a gene sets enriched or related to diseases vs matched normal tissues.

The PTPRG target gene set (Table 9) was compared to "OMIM expanded gene set", a gene set library created from NCBI's OMIM (online Mendelian Inheritance in Man) morbid map (Hamosh A, et al 2000, Hum Mutat. 2000; 15(1):57-61) and adapted as described in Chen et al 2013. The adapted OMIM morbid map provides gene-phenotype (disease) relationships where a gene is known to be involved or dysregulated in a condition or disease based on mutation, pathogenic variants, supportive functional data, such as comparable phenotype in a model organism, in vitro or in vivo enzyme or gene activity experiments, mutation located in a conserved region, or functional pathway support.

The Fisher exact test is used to compute enrichment. This is a proportion test that assumes a binomial distribution and independence for probability of any gene belonging to any set. The second test is a correction to the Fisher exact test based on intuition. Enrichment is first computed using the Fisher exact test for many random gene sets in order to compute a mean rank and standard deviation from the expected rank for each term in the gene-set library. Then using a lookup table of expected ranks with their variances, a z-score is computed for deviation from this expected rank, this can be a new corrected score for ranking terms.

TABLE 45

Conditions and Diseases With Non-Random, Statistically Significant Overlap of Disease-associated genes with PTPRG Targets Identified in Example 4

| Condition/Disease | Gene Overlap | P-value | Z-score | Combined Score |
|---|---|---|---|---|
| hypoglycemia | INSR; STAT3; JAK2; PTK2 | 0.00043 | −3.11 | 14.41 |
| renal cell carcinoma | STAT3; JAK2; MET; PTK2 | 0.00045 | −3.05 | 14.17 |
| colon cancer | SRC; STAT3; JAK2; PTK2 | 0.00043 | −2.90 | 13.43 |
| hepatocellular carcinoma | STAT3; JAK2; MET; PTK2 | 0.00045 | −2.89 | 13.39 |
| autism | STAT3; JAK2; MET; PTK2 | 0.00070 | −2.60 | 12.08 |
| ovarian cancer | ERBB2; STAT3; JAK2; PTK2 | 0.00053 | −2.41 | 11.18 |
| adenocarcinoma | ERBB2; STAT3; JAK2; PTK2 | 0.00041 | −2.32 | 10.77 |

TABLE 45-continued

Conditions and Diseases With Non-Random, Statistically Significant Overlap of Disease-associated genes with PTPRG Targets Identified in Example 4

| Condition/Disease | Gene Overlap | P-value | Z-score | Combined Score |
|---|---|---|---|---|
| gastric cancer | ERBB2; STAT3; JAK2; PTK2 | 0.00049 | −2.26 | 10.47 |
| glioblastoma | ERBB2; STAT3; JAK2; PTK2 | 0.00041 | −2.18 | 10.12 |
| asperger syndrome | STAT3; JAK2; PTK2 | 0.00576 | −1.48 | 6.87 |
| Diabetes mellitus, type 2 | INSR; STAT3; JAK2; PTK2 | 0.00100 | −1.44 | 6.66 |
| cardiomyopathy, dilated | STAT3; JAK2; VCL; PTK2 | 0.00115 | −1.29 | 6.01 |
| restless legs syndrome | STAT3; JAK2; PTK2 | 0.00576 | −1.16 | 5.37 |
| cardiomyopathy | STAT3; JAK2; VCL; PTK2 | 0.00149 | −1.16 | 5.37 |
| nephronophthisis | STAT3; JAK2; PTK2 | 0.00576 | −1.02 | 4.74 |
| lipodystrophy | STAT3; JAK2; PTK2 | 0.00576 | −0.96 | 4.47 |
| meckel syndrome | STAT3; JAK2; PTK2 | 0.00576 | −0.95 | 4.41 |
| lymphedema | STAT3; JAK2; PTK2 | 0.00576 | −0.77 | 3.59 |
| pheochromocytoma | STAT3; JAK2; PTK2 | 0.00576 | −0.65 | 3.04 |
| central hypoventilation syndrome | STAT3; JAK2; PTK2 | 0.00576 | −0.60 | 2.79 |
| dermatitis | STAT3; JAK2; PTK2 | 0.00595 | −0.51 | 2.35 |
| lymphoproliferative syndrome | STAT3; JAK2; PTK2 | 0.00576 | −0.48 | 2.24 |
| homocystinuria | STAT3; JAK2; PTK2 | 0.00576 | −0.48 | 2.22 |
| coronary heart disease | STAT3; JAK2; PTK2 | 0.00634 | −0.39 | 1.83 |
| keratosis | STAT3; JAK2; PTK2 | 0.00576 | −0.34 | 1.58 |
| autoimmune disease | STAT3; JAK2; PTK2 | 0.00576 | −0.33 | 1.54 |
| lissencephaly | STAT3; JAK2; PTK2 | 0.00576 | −0.31 | 1.44 |
| osteoarthritis | STAT3; JAK2; PTK2 | 0.00615 | −0.28 | 1.28 |
| sarcoma | STAT3; JAK2; PTK2 | 0.00595 | −0.23 | 1.06 |
| leukemia | PDGFRB; KIT; JAK2 | 0.00469 | −0.22 | 1.01 |
| epiphyseal dysplasia, multiple | STAT3; JAK2; PTK2 | 0.00595 | −0.19 | 0.87 |
| ovarian failure | STAT3; JAK2; PTK2 | 0.00595 | −0.14 | 0.66 |
| dyslexia | STAT3; JAK2; PTK2 | 0.00595 | −0.14 | 0.63 |
| tuberculosis | STAT3; JAK2; PTK2 | 0.00634 | −0.12 | 0.54 |
| arthrogryposis | STAT3; JAK2; PTK2 | 0.00576 | −0.07 | 0.34 |
| seizures | STAT3; JAK2; PTK2 | 0.00615 | −0.04 | 0.21 |
| adenoma | STAT3; JAK2; PTK2 | 0.00521 | −0.04 | 0.21 |
| wilms tumor | STAT3; JAK2; PTK2 | 0.00595 | −0.04 | 0.19 |
| preeclampsia | STAT3; JAK2; PTK2 | 0.00576 | −0.03 | 0.12 |
| hermansky-pudlak syndrome | STAT3; JAK2; PTK2 | 0.00615 | −0.02 | 0.11 |
| rickets | STAT3; JAK2; PTK2 | 0.00615 | −0.02 | 0.10 |
| diamond-blackfan anemia | STAT3; JAK2; PTK2 | 0.00615 | −0.01 | 0.07 |
| spinal muscular atrophy | STAT3; JAK2; PTK2 | 0.00634 | −0.01 | 0.07 |
| amelogenesis imperfecta | STAT3; JAK2; PTK2 | 0.00595 | −0.01 | 0.04 |
| bone mineral density | STAT3; JAK2; PTK2 | 0.00696 | 0.00 | 0.01 |
| cholestasis | STAT3; JAK2; PTK2 | 0.00576 | 0.00 | −0.01 |
| brachydactyly | STAT3; JAK2; PTK2 | 0.00634 | 0.03 | −0.15 |
| cutis laxa | STAT3; JAK2; PTK2 | 0.00595 | 0.03 | −0.16 |
| holoprosencephaly | STAT3; JAK2; PTK2 | 0.00634 | 0.06 | −0.27 |
| multiple sclerosis | STAT3; JAK2; PTK2 | 0.00634 | 0.06 | −0.29 |
| hypothyroidism | STAT3; JAK2; PTK2 | 0.00634 | 0.07 | −0.35 |
| thrombocytopenia | STAT3; JAK2; PTK2 | 0.00655 | 0.08 | −0.36 |
| osteopetrosis | STAT3; JAK2; PTK2 | 0.00615 | 0.09 | −0.43 |
| squamous cell carcinoma | STAT3; JAK2; PTK2 | 0.00595 | 0.12 | −0.56 |
| nephropathy | STAT3; JAK2; PTK2 | 0.00655 | 0.13 | −0.59 |
| otosclerosis | STAT3; JAK2; PTK2 | 0.00576 | 0.13 | −0.60 |
| myasthenic syndrome | STAT3; JAK2; PTK2 | 0.00615 | 0.15 | −0.67 |
| hirschsprung disease | STAT3; JAK2; PTK2 | 0.00655 | 0.15 | −0.69 |
| cone dystrophy | STAT3; JAK2; PTK2 | 0.00634 | 0.16 | −0.76 |
| bare lymphocyte syndrome | STAT3; JAK2; PTK2 | 0.00576 | 0.18 | −0.81 |
| ectodermal dysplasia | STAT3; JAK2; PTK2 | 0.00675 | 0.18 | −0.84 |
| thalassemia | STAT3; JAK2; PTK2 | 0.00615 | 0.19 | −0.89 |
| alopecia | STAT3; JAK2; PTK2 | 0.00675 | 0.20 | −0.91 |
| usher syndrome | STAT3; JAK2; PTK2 | 0.00675 | 0.20 | −0.95 |
| celiac disease | STAT3; JAK2; PTK2 | 0.00740 | 0.21 | −0.97 |
| stature | STAT3; JAK2; PTK2 | 0.00981 | 0.22 | −0.98 |
| coronary artery disease | STAT3; JAK2; PTK2 | 0.00655 | 0.22 | −1.01 |
| nevus | STAT3; JAK2; PTK2 | 0.00595 | 0.22 | −1.02 |
| endometrial cancer | STAT3; JAK2; PTK2 | 0.00595 | 0.22 | −1.02 |
| fanconi anemia | STAT3; JAK2; PTK2 | 0.00718 | 0.22 | −1.04 |
| malignant hyperthermia | STAT3; JAK2; PTK2 | 0.00576 | 0.23 | −1.05 |
| major affective disorder | STAT3; JAK2; PTK2 | 0.00655 | 0.24 | −1.10 |
| migraine | STAT3; JAK2; PTK2 | 0.00785 | 0.25 | −1.16 |
| ehlers-danlos | STAT3; JAK2; PTK2 | 0.00675 | 0.26 | −1.23 |
| hypogonadism | STAT3; JAK2; PTK2 | 0.00718 | 0.26 | −1.23 |
| psoriasis | STAT3; JAK2; PTK2 | 0.00696 | 0.27 | −1.27 |
| xeroderma pigmentosum | STAT3; JAK2; PTK2 | 0.00655 | 0.28 | −1.28 |

TABLE 45-continued

Conditions and Diseases With Non-Random, Statistically Significant Overlap of Disease-associated genes with PTPRG Targets Identified in Example 4

| Condition/Disease | Gene Overlap | P-value | Z-score | Combined Score |
|---|---|---|---|---|
| osteoporosis | STAT3; JAK2; PTK2 | 0.00655 | 0.28 | −1.29 |
| thrombophilia | STAT3; JAK2; PTK2 | 0.00675 | 0.28 | −1.29 |
| ciliary dyskinesia | STAT3; JAK2; PTK2 | 0.00696 | 0.28 | −1.32 |
| leukodystrophy | STAT3; JAK2; PTK2 | 0.00615 | 0.29 | −1.32 |
| complex i | STAT3; JAK2; PTK2 | 0.00634 | 0.29 | −1.32 |
| fetal hemoglobin quantitative trait locus | STAT3; JAK2; PTK2 | 0.00576 | 0.29 | −1.33 |
| fibrosis | STAT3; JAK2; PTK2 | 0.00696 | 0.29 | −1.33 |
| joubert syndrome | STAT3; JAK2; PTK2 | 0.00615 | 0.29 | −1.34 |
| macular dystrophy | STAT3; JAK2; PTK2 | 0.00655 | 0.29 | −1.36 |
| microcephaly | STAT3; JAK2; PTK2 | 0.00740 | 0.29 | −1.37 |
| dementia | STAT3; JAK2; PTK2 | 0.00696 | 0.30 | −1.38 |
| albinism | STAT3; JAK2; PTK2 | 0.00634 | 0.30 | −1.39 |
| pancreatic cancer | STAT3; JAK2; PTK2 | 0.00675 | 0.31 | −1.42 |
| aids | STAT3; JAK2; PTK2 | 0.00595 | 0.31 | −1.42 |
| epidermolysis bullosa | STAT3; JAK2; PTK2 | 0.00718 | 0.31 | −1.43 |
| rheumatoid arthritis | STAT3; JAK2; PTK2 | 0.00718 | 0.32 | −1.47 |
| malaria | STAT3; JAK2; PTK2 | 0.00740 | 0.32 | −1.48 |
| hypercholesterolemia | STAT3; JAK2; PTK2 | 0.00634 | 0.33 | −1.52 |
| skin/hair/eye pigmentation | STAT3; JAK2; PTK2 | 0.00696 | 0.35 | −1.60 |
| hypotrichosis | STAT3; JAK2; PTK2 | 0.00655 | 0.35 | −1.62 |
| pseudohypoaldosteronism | STAT3; JAK2; PTK2 | 0.00595 | 0.36 | −1.66 |
| aneurysm | STAT3; JAK2; PTK2 | 0.00831 | 0.36 | −1.67 |
| arrhythmogenic right ventricular dysplasia | STAT3; JAK2; PTK2 | 0.00718 | 0.36 | −1.68 |
| leigh syndrome | STAT3; JAK2; PTK2 | 0.00740 | 0.37 | −1.70 |
| melanoma | STAT3; JAK2; PTK2 | 0.00718 | 0.37 | −1.70 |
| cholesterol level | STAT3; JAK2; PTK2 | 0.00762 | 0.37 | −1.71 |
| attention-deficit hyperactivity disorder | STAT3; JAK2; PTK2 | 0.00634 | 0.38 | −1.77 |
| cone-rod dystrophy | STAT3; JAK2; PTK2 | 0.00762 | 0.38 | −1.77 |
| glycogen storage disease | STAT3; JAK2; PTK2 | 0.00718 | 0.38 | −1.77 |
| coloboma | STAT3; JAK2; PTK2 | 0.00634 | 0.38 | −1.78 |
| ceroid-lipofuscinosis, neuronal | STAT3; JAK2; PTK2 | 0.00615 | 0.39 | −1.79 |
| inflammatory bowel disease | STAT3; JAK2; PTK2 | 0.00955 | 0.40 | −1.82 |
| hiv | STAT3; JAK2; PTK2 | 0.00634 | 0.39 | −1.82 |
| microphthalmia | STAT3; JAK2; PTK2 | 0.00855 | 0.40 | −1.84 |
| leber amaurosis | STAT3; JAK2; PTK2 | 0.00718 | 0.40 | −1.85 |
| myocardial infarction | STAT3; JAK2; PTK2 | 0.00785 | 0.40 | −1.86 |
| long qt syndrome | STAT3; JAK2; PTK2 | 0.00675 | 0.40 | −1.86 |
| waardenburg syndrome | STAT3; JAK2; PTK2 | 0.00615 | 0.41 | −1.88 |
| zellweger syndrome | STAT3; JAK2; PTK2 | 0.00696 | 0.41 | −1.89 |
| lung cancer | STAT3; JAK2; PTK2 | 0.00879 | 0.42 | −1.90 |
| anomalies | STAT3; JAK2; PTK2 | 0.00718 | 0.41 | −1.91 |
| convulsions | STAT3; JAK2; PTK2 | 0.00740 | 0.41 | −1.92 |
| glaucoma | STAT3; JAK2; PTK2 | 0.00785 | 0.42 | −1.94 |
| paget disease | STAT3; JAK2; PTK2 | 0.00576 | 0.43 | −2.01 |
| bardet-biedl syndrome | STAT3; JAK2; PTK2 | 0.00762 | 0.44 | −2.04 |
| amyloidosis | STAT3; JAK2; PTK2 | 0.00595 | 0.44 | −2.04 |
| thyroid carcinoma | STAT3; JAK2; PTK2 | 0.00785 | 0.44 | −2.04 |
| ichthyosis | STAT3; JAK2; PTK2 | 0.00808 | 0.44 | −2.05 |
| corneal dystrophy | STAT3; JAK2; PTK2 | 0.00740 | 0.44 | −2.06 |
| myopia | STAT3; JAK2; PTK2 | 0.00762 | 0.45 | −2.09 |
| alzheimer disease | STAT3; JAK2; PTK2 | 0.01034 | 0.47 | −2.09 |
| optic atrophy | STAT3; JAK2; PTK2 | 0.00615 | 0.45 | −2.10 |
| cdeficiency | STAT3; JAK2; PTK2 | 0.00718 | 0.46 | −2.11 |
| encephalopathy | STAT3; JAK2; PTK2 | 0.00740 | 0.46 | −2.12 |
| dystonia | STAT3; JAK2; PTK2 | 0.00808 | 0.46 | −2.14 |
| macular degeneration | STAT3; JAK2; PTK2 | 0.00831 | 0.47 | −2.16 |
| polydactyly | STAT3; JAK2; PTK2 | 0.00595 | 0.48 | −2.21 |
| lateral sclerosis | STAT3; JAK2; PTK2 | 0.00855 | 0.48 | −2.22 |
| chondrodysplasia | STAT3; JAK2; PTK2 | 0.00634 | 0.48 | −2.24 |
| infections | STAT3; JAK2; PTK2 | 0.00576 | 0.49 | −2.28 |
| disorder of glycosylation | STAT3; JAK2; PTK2 | 0.00855 | 0.50 | −2.31 |
| prostate cancer | STAT3; JAK2; PTK2 | 0.01145 | 0.53 | −2.32 |
| atrial fibrillation | STAT3; JAK2; PTK2 | 0.00615 | 0.50 | −2.33 |
| leukoencephalopathy | STAT3; JAK2; PTK2 | 0.00615 | 0.50 | −2.33 |
| hypertension | STAT3; JAK2; PTK2 | 0.01117 | 0.55 | −2.42 |
| cardiomyopathy, hypertrophic | STAT3; JAK2; PTK2 | 0.00785 | 0.52 | −2.43 |
| diabetes mellitus, type 1 | STAT3; JAK2; PTK2 | 0.01034 | 0.55 | −2.46 |
| body mass index | STAT3; JAK2; PTK2 | 0.00595 | 0.54 | −2.48 |

TABLE 45-continued

Conditions and Diseases With Non-Random, Statistically Significant Overlap of
Disease-associated genes with PTPRG Targets Identified in Example 4

| Condition/Disease | Gene Overlap | P-value | Z-score | Combined Score |
|---|---|---|---|---|
| lymphoma | STAT3; JAK2; PTK2 | 0.00929 | 0.55 | −2.48 |
| asthma | STAT3; JAK2; PTK2 | 0.00929 | 0.56 | −2.55 |
| orofacial cleft | STAT3; JAK2; PTK2 | 0.00855 | 0.55 | −2.55 |
| parkinson disease | STAT3; JAK2; PTK2 | 0.00929 | 0.56 | −2.57 |
| systemic lupus erythematosus | STAT3; JAK2; PTK2 | 0.01089 | 0.60 | −2.66 |
| breast cancer | STAT3; JAK2; PTK2 | 0.01089 | 0.60 | −2.68 |
| mucopolysaccharidosis | STAT3; JAK2; PTK2 | 0.00576 | 0.59 | −2.74 |
| charcot-marie-tooth disease | STAT3; JAK2; PTK2 | 0.01061 | 0.62 | −2.78 |
| colorectal cancer | STAT3; JAK2; PTK2 | 0.01264 | 0.64 | −2.78 |
| obesity | STAT3; JAK2; PTK2 | 0.01145 | 0.64 | −2.83 |
| neutropenia | STAT3; JAK2; PTK2 | 0.00595 | 0.61 | −2.83 |
| immunodeficiency | STAT3; JAK2; PTK2 | 0.01089 | 0.64 | −2.84 |
| spinocerebellar ataxia | STAT3; JAK2; PTK2 | 0.01357 | 0.67 | −2.87 |
| hemochromatosis | STAT3; JAK2; PTK2 | 0.00576 | 0.62 | −2.87 |
| spastic paraplegia | STAT3; JAK2; PTK2 | 0.01204 | 0.69 | −3.01 |
| schizophrenia | STAT3; JAK2; PTK2 | 0.01145 | 0.69 | −3.02 |
| neuropathy | STAT3; JAK2; PTK2 | 0.01294 | 0.70 | −3.03 |
| muscular dystrophy | STAT3; JAK2; PTK2 | 0.01204 | 0.71 | −3.12 |
| night blindness | STAT3; JAK2; PTK2 | 0.00595 | 0.68 | −3.15 |
| myopathy | STAT3; JAK2; PTK2 | 0.01555 | 0.78 | −3.23 |
| goiter | STAT3; JAK2; PTK2 | 0.00576 | 0.70 | −3.27 |
| cataract | STAT3; JAK2; PTK2 | 0.01697 | 0.82 | −3.34 |
| porphyria | STAT3; JAK2; PTK2 | 0.00595 | 0.74 | −3.41 |
| bartter syndrome | STAT3; JAK2; PTK2 | 0.00576 | 0.81 | −3.76 |
| diabetes | INSR | 0.29498 | 3.15 | −3.85 |
| refsum disease | STAT3; JAK2; PTK2 | 0.00576 | 0.87 | −4.02 |
| adrenoleukodystrophy | STAT3; JAK2; PTK2 | 0.00576 | 0.98 | −4.56 |
| kallmann syndrome | STAT3; JAK2; PTK2 | 0.00576 | 1.02 | −4.72 |
| episodic ataxia | STAT3; JAK2; PTK2 | 0.00576 | 1.10 | −5.13 |
| mitochondrial dna depletion syndrome | STAT3; JAK2; PTK2 | 0.00576 | 1.18 | −5.46 |
| dyskeratosis | STAT3; JAK2; PTK2 | 0.00576 | 1.30 | −6.04 |
| atopy | STAT3; JAK2; PTK2 | 0.00576 | 1.37 | −6.34 |
| vitreoretinopathy | STAT3; JAK2; PTK2 | 0.00576 | 1.38 | −6.42 |

A number of conditions were found where there is statistically significant, non-random overlap of PTPRG targets in monocytes, and genes known to be involved or dysregulated in that condition, including conditions where PTPRG expression and/or activity is known to be decreased such as renal cell carcinoma, hepatocellular carcinoma and others. There are a number of conditions where the targets of PTPRG are known to be dysregulated, for example JAK2, and also a number of conditions where no previous association between PTPRG was known. Both glioblastoma and beta-thalassemia, shown herein to respond to PTPRG activity manipulation, were identified.

What is claimed is:

1. A method of increasing protein tyrosine phosphatase receptor type gamma (PTPRG) activity in hematopoietic stem or progenitor cells of an individual suffering from β-thalassemia, the method comprising:
   contacting the hematopoietic stem or progenitor cells with an effective dose of a protein tyrosine phosphatase (PTP) activating agent selected from a PTP wedge domain (WD) polypeptide; a PTP intracellular domain (ICD) polypeptide; a PTP intracellular phosphatase domain (IPD) peptide; and a PTP soluble extracellular domain polypeptide (PTPx);
   wherein PTPRG activity in the cell is increased.

2. The method of claim 1, wherein the effective dose increases PTPRG activity to result in altered tyrosine phosphorylation of one or more target proteins.

3. The method of claim 1, wherein the PTP activating agent is a human polypeptide or a fusion polypeptide thereof, optionally fused to a permeant domain.

4. The method of claim 1, wherein endogenous PTPRG protein in the cell is activated.

5. The method of claim 1, wherein the PTP activating agent is a human PTPRG ICD or IPD polypeptide or fusion polypeptide thereof.

6. The method of claim 5, wherein the ICD or IPD provides phosphatase activity in the absence of endogenous PTPRG.

7. A method of increasing protein tyrosine phosphatase receptor type gamma (PTPRG) activity in hematopoietic stem or progenitor cells of an individual suffering from b-thalassemia, the method comprising:
   contacting the hematopoietic stem or progenitor cells with an effective dose of a protein tyrosine phosphatase (PTP) activating polypeptide, wherein the polypeptide comprises an isolated PTPRG peptide comprising the amino acid sequence set forth in any one of SEQ ID NO:1, SEQ ID NO:2, SEQ ID NO:6, SEQ ID NO:7 or SEQ ID NO:8
   wherein PTPRG activity in the cell is increased.

* * * * *

```
                        SEQUENCE LISTING

<160> NUMBER OF SEQ ID NOS: 8

<210> SEQ ID NO 1
<211> LENGTH: 26
<212> TYPE: PRT
<213> ORGANISM: Homo sapiens

<400> SEQUENCE: 1

Lys Gln Phe Val Lys His Ile Gly Glu Leu Tyr Ser Asn Asn Gln His
1               5                   10                  15

Gly Phe Ser Glu Asp Phe Glu Glu Val Gln
            20                  25

<210> SEQ ID NO 2
<211> LENGTH: 11
<212> TYPE: PRT
<213> ORGANISM: Homo sapiens

<400> SEQUENCE: 2
```

His Gly Phe Ser Glu Asp Phe Glu Glu Val Gln
1               5                   10

<210> SEQ ID NO 3
<211> LENGTH: 43
<212> TYPE: PRT
<213> ORGANISM: Homo sapiens

<400> SEQUENCE: 3

Arg Gln Ile Lys Ile Trp Phe Gln Asn Arg Arg Met Lys Trp Lys Lys
1               5                   10                  15

Gly Lys Gln Phe Val Lys His Ile Gly Glu Leu Tyr Ser Asn Asn Gln
            20                  25                  30

His Gly Phe Ser Glu Asp Phe Glu Glu Val Gln
        35                  40

<210> SEQ ID NO 4
<211> LENGTH: 16
<212> TYPE: PRT
<213> ORGANISM: Homo sapiens

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 662
<212> TYPE: PRT
<213> ORGANISM: Homo sapiens

<400> SEQUENCE: 5

Gly Arg Lys Lys Arg Arg Gln Arg Arg Pro Pro Gln Thr Ala His
1               5                   10                  15

Phe Tyr Val Glu Asp Ser Ser Pro Arg Val Val Pro Asn Glu Ser
            20                  25                  30

Ile Pro Ile Ile Pro Ile Pro Asp Asp Met Glu Ala Ile Pro Val Lys
            35                  40                  45

Gln Phe Val Lys His Ile Gly Glu Leu Tyr Ser Asn Asn Gln His Gly
    50                  55                  60

Phe Ser Glu Asp Phe Glu Glu Val Gln Arg Cys Thr Ala Asp Met Asn
65                  70                  75                  80

Ile Thr Ala Glu His Ser Asn His Pro Glu Asn Lys His Lys Asn Arg
                85                  90                  95

Tyr Ile Asn Ile Leu Ala Tyr Asp His Ser Arg Val Lys Leu Arg Pro
            100                 105                 110

Leu Pro Gly Lys Asp Ser Lys His Ser Asp Tyr Ile Asn Ala Asn Tyr
        115                 120                 125

Val Asp Gly Tyr Asn Lys Ala Lys Ala Tyr Ile Ala Thr Gln Gly Pro
    130                 135                 140

Leu Lys Ser Thr Phe Glu Asp Phe Trp Arg Met Ile Trp Glu Gln Asn
145                 150                 155                 160

Thr Gly Ile Ile Val Met Ile Thr Asn Leu Val Glu Lys Gly Arg Arg
                165                 170                 175

Lys Cys Asp Gln Tyr Trp Pro Thr Glu Asn Ser Glu Glu Tyr Gly Asn
            180                 185                 190

Ile Ile Val Thr Leu Lys Ser Thr Lys Ile His Ala Cys Tyr Thr Val
        195                 200                 205

-continued

Arg Arg Phe Ser Ile Arg Asn Thr Lys Val Lys Lys Gly Gln Lys Gly
210                 215                 220

Asn Pro Lys Gly Arg Gln Asn Glu Arg Val Val Ile Gln Tyr His Tyr
225                 230                 235                 240

Thr Gln Trp Pro Asp Met Gly Val Pro Glu Tyr Ala Leu Pro Val Leu
            245                 250                 255

Thr Phe Val Arg Arg Ser Ser Ala Ala Arg Met Pro Glu Thr Gly Pro
        260                 265                 270

Val Leu Val His Cys Ser Ala Gly Val Gly Arg Thr Gly Thr Tyr Ile
        275                 280                 285

Val Ile Asp Ser Met Leu Gln Gln Ile Lys Asp Lys Ser Thr Val Asn
290                 295                 300

Val Leu Gly Phe Leu Lys His Ile Arg Thr Gln Arg Asn Tyr Leu Val
305                 310                 315                 320

Gln Thr Glu Glu Gln Tyr Ile Phe Ile His Asp Ala Leu Leu Glu Ala
                325                 330                 335

Ile Leu Gly Lys Glu Thr Glu Val Ser Ser Asn Gln Leu His Ser Tyr
            340                 345                 350

Val Asn Ser Ile Leu Ile Pro Gly Val Gly Gly Lys Thr Arg Leu Glu
355                 360                 365

Lys Gln Phe Lys Leu Val Thr Gln Cys Asn Ala Lys Tyr Val Glu Cys
370                 375                 380

Phe Ser Ala Gln Lys Glu Cys Asn Lys Glu Lys Asn Arg Asn Ser Ser
385                 390                 395                 400

Val Val Pro Ser Glu Arg Ala Arg Val Gly Leu Ala Pro Leu Pro Gly
                405                 410                 415

Met Lys Gly Thr Asp Tyr Ile Asn Ala Ser Tyr Ile Met Gly Tyr Tyr
            420                 425                 430

Arg Ser Asn Glu Phe Ile Ile Thr Gln His Pro Leu Pro His Thr Thr
        435                 440                 445

Lys Asp Phe Trp Arg Met Ile Trp Asp His Asn Ala Gln Ile Ile Val
450                 455                 460

Met Leu Pro Asp Asn Gln Ser Leu Ala Glu Asp Glu Phe Val Tyr Trp
465                 470                 475                 480

Pro Ser Arg Glu Glu Ser Met Asn Cys Glu Ala Phe Thr Val Thr Leu
                485                 490                 495

Ile Ser Lys Asp Arg Leu Cys Leu Ser Asn Glu Glu Gln Ile Ile Ile
            500                 505                 510

His Asp Phe Ile Leu Glu Ala Thr Gln Asp Asp Tyr Val Leu Glu Val
        515                 520                 525

Arg His Phe Gln Cys Pro Lys Trp Pro Asn Pro Asp Ala Pro Ile Ser
530                 535                 540

Ser Thr Phe Glu Leu Ile Asn Val Ile Lys Glu Glu Ala Leu Thr Arg
545                 550                 555                 560

Asp Gly Pro Thr Ile Val His Asp Glu Tyr Gly Ala Val Ser Ala Gly
                565                 570                 575

Met Leu Cys Ala Leu Thr Thr Leu Ser Gln Gln Leu Glu Asn Glu Asn
            580                 585                 590

Ala Val Asp Val Phe Gln Val Ala Lys Met Ile Asn Leu Met Arg Pro
        595                 600                 605

Gly Val Phe Thr Asp Ile Glu Gln Tyr Gln Phe Ile Tyr Lys Ala Met
610                 615                 620

Leu Ser Leu Val Ser Thr Lys Glu Asn Gly Asn Gly Pro Met Thr Val

```
                625                 630                 635                 640

Asp Lys Asn Gly Ala Val Leu Ile Ala Asp Glu Ser Asp Pro Ala Glu
                        645                 650                 655

Ser Met Glu Ser Leu Val
                660

<210> SEQ ID NO 6
<211> LENGTH: 649
<212> TYPE: PRT
<213> ORGANISM: Homo sapiens

<400> SEQUENCE: 6

Thr Ala His Phe Tyr Val Glu Asp Ser Ser Pro Arg Val Val Pro
1               5                   10                  15

Asn Glu Ser Ile Pro Ile Ile Pro Asp Asp Met Glu Ala Ile
                20              25                  30

Pro Val Lys Gln Phe Val Lys His Ile Gly Glu Leu Tyr Ser Asn Asn
                35                  40                  45

Gln His Gly Phe Ser Glu Asp Phe Glu Val Gln Arg Cys Thr Ala
        50                  55                  60

Asp Met Asn Ile Thr Ala Glu His Ser Asn His Pro Glu Asn Lys His
65                  70                  75                  80

Lys Asn Arg Tyr Ile Asn Ile Leu Ala Tyr Asp His Ser Arg Val Lys
                        85                  90                  95

Leu Arg Pro Leu Pro Gly Lys Asp Ser Lys His Ser Asp Tyr Ile Asn
                100                 105                 110

Ala Asn Tyr Val Asp Gly Tyr Asn Lys Ala Lys Ala Tyr Ile Ala Thr
                115                 120                 125

Gln Gly Pro Leu Lys Ser Thr Phe Glu Asp Phe Trp Arg Met Ile Trp
            130                 135                 140

Glu Gln Asn Thr Gly Ile Ile Val Met Ile Thr Asn Leu Val Glu Lys
145                 150                 155                 160

Gly Arg Arg Lys Cys Asp Gln Tyr Trp Pro Thr Glu Asn Ser Glu Glu
                        165                 170                 175

Tyr Gly Asn Ile Ile Val Thr Leu Lys Ser Thr Lys Ile His Ala Cys
                180                 185                 190

Tyr Thr Val Arg Arg Phe Ser Ile Arg Asn Thr Lys Val Lys Lys Gly
            195                 200                 205

Gln Lys Gly Asn Pro Lys Gly Arg Gln Asn Glu Arg Val Val Ile Gln
        210                 215                 220

Tyr His Tyr Thr Gln Trp Pro Asp Met Gly Val Pro Glu Tyr Ala Leu
225                 230                 235                 240

Pro Val Leu Thr Phe Val Arg Arg Ser Ser Ala Ala Arg Met Pro Glu
                        245                 250                 255

Thr Gly Pro Val Leu Val His Cys Ser Ala Gly Val Gly Arg Thr Gly
                260                 265                 270

Thr Tyr Ile Val Ile Asp Ser Met Leu Gln Gln Ile Lys Asp Lys Ser
            275                 280                 285

Thr Val Asn Val Leu Gly Phe Leu Lys His Ile Arg Thr Gln Arg Asn
        290                 295                 300

Tyr Leu Val Gln Thr Glu Glu Gln Tyr Ile Phe Ile His Asp Ala Leu
305                 310                 315                 320

Leu Glu Ala Ile Leu Gly Lys Glu Thr Glu Val Ser Ser Asn Gln Leu
                        325                 330                 335
```

-continued

```
His Ser Tyr Val Asn Ser Ile Leu Ile Pro Gly Val Gly Lys Thr
            340                 345                 350

Arg Leu Glu Lys Gln Phe Lys Leu Val Thr Gln Cys Asn Ala Lys Tyr
        355                 360                 365

Val Glu Cys Phe Ser Ala Gln Lys Glu Cys Asn Lys Glu Lys Asn Arg
370                 375                 380

Asn Ser Ser Val Val Pro Ser Glu Arg Ala Arg Val Gly Leu Ala Pro
385                 390                 395                 400

Leu Pro Gly Met Lys Gly Thr Asp Tyr Ile Asn Ala Ser Tyr Ile Met
                405                 410                 415

Gly Tyr Tyr Arg Ser Asn Glu Phe Ile Ile Thr Gln His Pro Leu Pro
            420                 425                 430

His Thr Thr Lys Asp Phe Trp Arg Met Ile Trp Asp His Asn Ala Gln
        435                 440                 445

Ile Ile Val Met Leu Pro Asp Asn Gln Ser Leu Ala Glu Asp Glu Phe
    450                 455                 460

Val Tyr Trp Pro Ser Arg Glu Glu Ser Met Asn Cys Glu Ala Phe Thr
465                 470                 475                 480

Val Thr Leu Ile Ser Lys Asp Arg Leu Cys Leu Ser Asn Glu Glu Gln
                485                 490                 495

Ile Ile Ile His Asp Phe Ile Leu Glu Ala Thr Gln Asp Asp Tyr Val
            500                 505                 510

Leu Glu Val Arg His Phe Gln Cys Pro Lys Trp Pro Asn Pro Asp Ala
        515                 520                 525

Pro Ile Ser Ser Thr Phe Glu Leu Ile Asn Val Ile Lys Glu Glu Ala
530                 535                 540

Leu Thr Arg Asp Gly Pro Thr Ile Val His Asp Glu Tyr Gly Ala Val
545                 550                 555                 560

Ser Ala Gly Met Leu Cys Ala Leu Thr Thr Leu Ser Gln Gln Leu Glu
                565                 570                 575

Asn Glu Asn Ala Val Asp Val Phe Gln Val Ala Lys Met Ile Asn Leu
            580                 585                 590

Met Arg Pro Gly Val Phe Thr Asp Ile Glu Gln Tyr Gln Phe Ile Tyr
        595                 600                 605

Lys Ala Met Leu Ser Leu Val Ser Thr Lys Glu Asn Gly Asn Gly Pro
    610                 615                 620

Met Thr Val Asp Lys Asn Gly Ala Val Leu Ile Ala Asp Glu Ser Asp
625                 630                 635                 640

Pro Ala Glu Ser Met Glu Ser Leu Val
                645

<210> SEQ ID NO 7
<211> LENGTH: 600
<212> TYPE: PRT
<213> ORGANISM: Homo sapiens

<400> SEQUENCE: 7

His Gly Phe Ser Glu Asp Phe Glu Glu Val Gln Arg Cys Thr Ala Asp
1               5                   10                  15

Met Asn Ile Thr Ala Glu His Ser Asn His Pro Glu Asn Lys His Lys
            20                  25                  30

Asn Arg Tyr Ile Asn Ile Leu Ala Tyr Asp His Ser Arg Val Lys Leu
        35                  40                  45

Arg Pro Leu Pro Gly Lys Asp Ser Lys His Ser Asp Tyr Ile Asn Ala
    50                  55                  60
```

```
Asn Tyr Val Asp Gly Tyr Asn Lys Ala Lys Ala Tyr Ile Ala Thr Gln
 65                  70                  75                  80

Gly Pro Leu Lys Ser Thr Phe Glu Asp Phe Trp Arg Met Ile Trp Glu
                 85                  90                  95

Gln Asn Thr Gly Ile Ile Val Met Ile Thr Asn Leu Val Glu Lys Gly
            100                 105                 110

Arg Arg Lys Cys Asp Gln Tyr Trp Pro Thr Glu Asn Ser Glu Glu Tyr
            115                 120                 125

Gly Asn Ile Ile Val Thr Leu Lys Ser Thr Lys Ile His Ala Cys Tyr
130                 135                 140

Thr Val Arg Arg Phe Ser Ile Arg Asn Thr Lys Val Lys Lys Gly Gln
145                 150                 155                 160

Lys Gly Asn Pro Lys Gly Arg Gln Asn Glu Arg Val Val Ile Gln Tyr
                165                 170                 175

His Tyr Thr Gln Trp Pro Asp Met Gly Val Pro Glu Tyr Ala Leu Pro
            180                 185                 190

Val Leu Thr Phe Val Arg Arg Ser Ala Ala Arg Met Pro Glu Thr
                195                 200                 205

Gly Pro Val Leu Val His Cys Ser Ala Gly Val Gly Arg Thr Gly Thr
            210                 215                 220

Tyr Ile Val Ile Asp Ser Met Leu Gln Gln Ile Lys Asp Lys Ser Thr
225                 230                 235                 240

Val Asn Val Leu Gly Phe Leu Lys His Ile Arg Thr Gln Arg Asn Tyr
                245                 250                 255

Leu Val Gln Thr Glu Glu Gln Tyr Ile Phe Ile His Asp Ala Leu Leu
            260                 265                 270

Glu Ala Ile Leu Gly Lys Glu Thr Glu Val Ser Ser Asn Gln Leu His
            275                 280                 285

Ser Tyr Val Asn Ser Ile Leu Ile Pro Gly Val Gly Gly Lys Thr Arg
290                 295                 300

Leu Glu Lys Gln Phe Lys Leu Val Thr Gln Cys Asn Ala Lys Tyr Val
305                 310                 315                 320

Glu Cys Phe Ser Ala Gln Lys Glu Cys Asn Lys Glu Lys Asn Arg Asn
                325                 330                 335

Ser Ser Val Val Pro Ser Glu Arg Ala Arg Val Gly Leu Ala Pro Leu
            340                 345                 350

Pro Gly Met Lys Gly Thr Asp Tyr Ile Asn Ala Ser Tyr Ile Met Gly
            355                 360                 365

Tyr Tyr Arg Ser Asn Glu Phe Ile Ile Thr Gln His Pro Leu Pro His
            370                 375                 380

Thr Thr Lys Asp Phe Trp Arg Met Ile Trp Asp His Asn Ala Gln Ile
385                 390                 395                 400

Ile Val Met Leu Pro Asp Asn Gln Ser Leu Ala Glu Asp Glu Phe Val
                405                 410                 415

Tyr Trp Pro Ser Arg Glu Glu Ser Met Asn Cys Glu Ala Phe Thr Val
                420                 425                 430

Thr Leu Ile Ser Lys Asp Arg Leu Cys Leu Ser Asn Glu Glu Gln Ile
            435                 440                 445

Ile Ile His Asp Phe Ile Leu Glu Ala Thr Gln Asp Asp Tyr Val Leu
            450                 455                 460

Glu Val Arg His Phe Gln Cys Pro Lys Trp Pro Asn Pro Asp Ala Pro
465                 470                 475                 480
```

```
Ile Ser Ser Thr Phe Glu Leu Ile Asn Val Ile Lys Glu Glu Ala Leu
                485                 490                 495

Thr Arg Asp Gly Pro Thr Ile Val His Asp Glu Tyr Gly Ala Val Ser
            500                 505                 510

Ala Gly Met Leu Cys Ala Leu Thr Thr Leu Ser Gln Gln Leu Glu Asn
            515                 520                 525

Glu Asn Ala Val Asp Val Phe Gln Val Ala Lys Met Ile Asn Leu Met
        530                 535                 540

Arg Pro Gly Val Phe Thr Asp Ile Glu Gln Tyr Gln Phe Ile Tyr Lys
545                 550                 555                 560

Ala Met Leu Ser Leu Val Ser Thr Lys Glu Asn Gly Asn Gly Pro Met
                565                 570                 575

Thr Val Asp Lys Asn Gly Ala Val Leu Ile Ala Asp Glu Ser Asp Pro
            580                 585                 590

Ala Glu Ser Met Glu Ser Leu Val
            595                 600

<210> SEQ ID NO 8
<211> LENGTH: 717
<212> TYPE: PRT
<213> ORGANISM: Homo sapiens

<400> SEQUENCE: 8

Val Leu His Tyr Val Val Cys Phe Pro Ala Leu Thr Glu Gly Tyr Val
1               5                   10                  15

Gly Ala Leu His Glu Asn Arg His Gly Ser Ala Val Gln Ile Arg Arg
            20                  25                  30

Arg Lys Ala Ser Gly Asp Pro Tyr Trp Ala Tyr Ser Gly Ala Tyr Gly
        35                  40                  45

Pro Glu His Trp Val Thr Ser Ser Val Ser Cys Gly Arg His Gln
    50                  55                  60

Ser Pro Ile Asp Ile Leu Asp Gln Tyr Ala Arg Val Gly Glu Glu Tyr
65                  70                  75                  80

Gln Glu Leu Gln Leu Asp Gly Phe Asp Asn Glu Ser Ser Asn Lys Thr
                85                  90                  95

Trp Met Lys Asn Thr Gly Lys Thr Val Ala Ile Leu Leu Lys Asp Asp
                100                 105                 110

Tyr Phe Val Ser Gly Ala Gly Leu Pro Gly Arg Phe Lys Ala Glu Lys
            115                 120                 125

Val Glu Phe His Trp Gly His Ser Asn Gly Ser Ala Gly Ser Glu His
        130                 135                 140

Ser Ile Asn Gly Arg Arg Phe Pro Val Glu Met Gln Ile Phe Phe Tyr
145                 150                 155                 160

Asn Pro Asp Asp Phe Asp Ser Phe Gln Thr Ala Ile Ser Glu Asn Arg
                165                 170                 175

Ile Ile Gly Ala Met Ala Ile Phe Phe Gln Val Ser Pro Arg Asp Asn
            180                 185                 190

Ser Ala Leu Asp Pro Ile Ile His Gly Leu Lys Gly Val Val His His
        195                 200                 205

Glu Lys Glu Thr Phe Leu Asp Pro Phe Val Leu Arg Asp Leu Leu Pro
    210                 215                 220

Ala Ser Leu Gly Ser Tyr Tyr Arg Tyr Thr Gly Ser Leu Thr Thr Pro
225                 230                 235                 240

Pro Cys Ser Glu Ile Val Glu Trp Ile Val Phe Arg Arg Pro Val Pro
                245                 250                 255
```

```
Ile Ser Tyr His Gln Leu Glu Ala Phe Tyr Ser Ile Phe Thr Thr Glu
            260                 265                 270

Gln Gln Asp His Val Lys Ser Glu Tyr Leu Arg Asn Asn Phe Arg
            275                 280                 285

Pro Gln Gln Arg Leu His Asp Arg Val Val Ser Lys Ser Ala Val Arg
290                 295                 300

Asp Ser Trp Asn His Asp Met Thr Asp Phe Leu Glu Asn Pro Leu Gly
305                 310                 315                 320

Thr Glu Ala Ser Lys Val Cys Ser Ser Pro Ile His Met Lys Val
            325                 330                 335

Gln Pro Leu Asn Gln Thr Ala Leu Gln Val Ser Trp Ser Gln Pro Glu
            340                 345                 350

Thr Ile Tyr His Pro Pro Ile Met Asn Tyr Met Ile Ser Tyr Ser Trp
            355                 360                 365

Thr Lys Asn Glu Asp Glu Lys Glu Lys Thr Phe Thr Lys Asp Ser Asp
            370                 375                 380

Lys Asp Leu Lys Ala Thr Ile Ser His Val Ser Pro Asp Ser Leu Tyr
385                 390                 395                 400

Leu Phe Arg Val Gln Ala Val Cys Arg Asn Asp Met Arg Ser Asp Phe
                405                 410                 415

Ser Gln Thr Met Leu Phe Gln Ala Asn Thr Thr Arg Ile Phe Gln Gly
            420                 425                 430

Thr Arg Ile Val Lys Thr Gly Val Pro Thr Ala Ser Pro Ala Ser Ser
            435                 440                 445

Ala Asp Met Ala Pro Ile Ser Ser Gly Ser Ser Thr Trp Thr Ser Ser
450                 455                 460

Gly Ile Pro Phe Ser Phe Val Ser Met Ala Thr Gly Met Gly Pro Ser
465                 470                 475                 480

Ser Ser Gly Ser Gln Ala Thr Val Ala Ser Val Val Thr Ser Thr Leu
            485                 490                 495

Leu Ala Gly Leu Gly Phe Gly Gly Gly Ile Ser Ser Phe Pro Ser
            500                 505                 510

Thr Val Trp Pro Thr Arg Leu Pro Thr Ala Ala Ser Ala Ser Lys Gln
            515                 520                 525

Ala Ala Arg Pro Val Leu Ala Thr Thr Glu Ala Leu Ala Ser Pro Gly
530                 535                 540

Pro Asp Gly Asp Ser Ser Pro Thr Lys Asp Gly Glu Gly Thr Glu Glu
545                 550                 555                 560

Gly Glu Lys Asp Glu Lys Ser Glu Ser Glu Asp Gly Glu Arg Glu His
                565                 570                 575

Glu Glu Asp Gly Glu Lys Asp Ser Glu Lys Lys Glu Lys Ser Gly Val
            580                 585                 590

Thr His Ala Ala Glu Glu Arg Asn Gln Thr Glu Pro Ser Pro Thr Pro
            595                 600                 605

Ser Ser Pro Asn Arg Thr Ala Glu Gly Gly His Gln Thr Ile Pro Gly
            610                 615                 620

His Glu Gln Asp His Thr Ala Val Pro Thr Asp Gln Thr Gly Gly Arg
625                 630                 635                 640

Arg Asp Ala Gly Pro Gly Leu Asp Pro Asp Met Val Thr Ser Thr Gln
                645                 650                 655

Val Pro Pro Thr Ala Thr Glu Glu Gln Tyr Ala Gly Ser Asp Pro Lys
            660                 665                 670
```

-continued

```
Arg Pro Glu Met Pro Ser Lys Lys Pro Met Ser Arg Gly Asp Arg Phe
        675                 680                 685

Ser Glu Asp Ser Arg Phe Ile Thr Val Asn Pro Ala Glu Lys Asn Thr
        690                 695                 700

Ser Gly Met Ile Ser Arg Pro Ala Pro Gly Arg Met Glu
705                 710                 715
```